US012766153B2

(12) United States Patent
Bulun et al.

(10) Patent No.: US 12,766,153 B2
(45) Date of Patent: Oct. 20, 2026

(54) METHODS AND COMPOSITIONS FOR TREATING AND/OR PREVENTING HERNIAS

(71) Applicant: Northwestern University, Evanston, IL (US)

(72) Inventors: Serdar E. Bulun, Evanston, IL (US); Hong Zhao, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 18/978,320

(22) Filed: Dec. 12, 2024

(65) Prior Publication Data

US 2025/0186461 A1 Jun. 12, 2025

Related U.S. Application Data

(60) Provisional application No. 63/609,158, filed on Dec. 12, 2023.

(51) Int. Cl.

| | |
|---|---|
| ***A61K 31/575*** | (2006.01) |
| ***A61K 31/567*** | (2006.01) |
| ***A61K 31/57*** | (2006.01) |
| ***A61P 21/00*** | (2006.01) |

(52) U.S. Cl.

CPC .......... *A61K 31/575* (2013.01); *A61K 31/567* (2013.01); *A61K 31/57* (2013.01); *A61P 21/00* (2018.01)

(58) Field of Classification Search

CPC ........................ A61P 21/00; A61K 31/56-575

See application file for complete search history.

(56) References Cited

U.S. PATENT DOCUMENTS

2007/0213306 A1* 9/2007 Hausknecht .............. A61P 7/06 514/169

OTHER PUBLICATIONS

"How to Prevent and Treat Hernias" by The Surgical Clinic (retrieved from https://thesurgicalclinics.com/ on Dec. 9, 2025) (Year: 2025).*

Aasbo V, Thuen A, Raeder J. Improved long-lasting postoperative analgesia, recovery function and patient satisfaction after inguinal hernia repair with inguinal field block compared with general anesthesia. Acta anaesthesiologica Scandinavica. 2002;46(6):674-8. PubMed PMID: 12059890.

Aasvang E, Kehlet H. Chronic postoperative pain: the case of inguinal herniorrhaphy. British journal of anaesthesia. 2005;95(1):69-76. doi: 10.1093/bja/aei019. PubMed PMID: 15531621.

Aiman J, Brenner PF, MacDonald PC. Androgen and estrogen production in elderly men with gynecomastia and testicular atrophy after mumps orchitis. The Journal of clinical endocrinology and metabolism. 1980;50(2):380-6. Epub Feb. 1, 1980. doi: 10.1210/jcem-50-2-380. PubMed PMID: 7354122.

(Continued)

*Primary Examiner* — Theodore R. Howell

(74) *Attorney, Agent, or Firm* — Quarles & Brady LLP

(57) ABSTRACT

Methods and compositions for treating and/or preventing hernias in subjects in need thereof. The methods of treatment can include administering to the subject one or more therapeutic agents that modulate the activity of progesterone and/or the progesterone receptor in the subject.

17 Claims, 19 Drawing Sheets

(56) References Cited

OTHER PUBLICATIONS

Al-Khyatt W, Tufarelli C, Khan R, Iftikhar SY. Selective oestrogen receptor antagonists inhibit oesophageal cancer cell proliferation in vitro. BMC Cancer. 2018;18(1):121. doi: 10.1186/s12885-018-4030-5. PubMed PMID: 29390981; PMCID: 5796348.
Andraus W, Pinheiro RS, Lai Q, Haddad LBP, Nacif LS, D'Albuquerque LAC, Lerut J. Abdominal wall hernia in cirrhotic patients: emergency surgery results in higher morbidity and mortality. BMC Surg. 2015;15:65. doi: 10.1186/s12893-015-0052-y. PubMed PMID: 25990110; PMCID: 4443633.
Bay_Nielsen M, Kehlet H, Strand L, Malmstrom J, Andersen FH, Wara P, Juul P, Callesen T, Danish Hernia Database C. Quality assessment of 26,304 herniorrhaphies in Denmark: a prospective nationwide study. Lancet. 2001;358(9288):1124-8. doi: 10.1016/S0140-6736(01)06251-1. PubMed PMID: 11597665.
Beachler DC, de Luise C, Jamal-Allial A, Yin R, Taylor DH, Suzuki A, Lewis JH, Freston JW, Lanes S. Real-world safety of palbociclib in breast cancer patients in the United States: a new user cohort study. BMC Cancer. 2021;21(1):97. Epub Jan. 27, 2021. doi: 10.1186/s12885-021-07790-z. PubMed PMID: 33494720; PMCID: PMC7831235.
Belghiti J, Durand F. Abdominal wall hernias in the setting of cirrhosis. Semin Liver Dis. 1997;17(3):219-26. doi: 10.1055/s-2007-1007199. PubMed PMID: 9308126.
Brisken C, Scabia V. 90 Years of Progesterone: Progesterone receptor signaling in the normal breast and its implications for cancer. Journal of molecular endocrinology. 2020;65(1):T81-T94. Epub Jun. 9, 2020. doi: 10.1530/JME-20-0091. PubMed PMID: 32508307.
Brooks DC, Coon VJ, Ercan CM, Xu X, Dong H, Levine JE, Bulun SE, Zhao H. Brain Aromatase and the Regulation of Sexual Activity in Male Mice. Endocrinology. 2020;161(10). Epub Sep. 11, 2020. doi: 10.1210/endocr/bqaa137. PubMed PMID: 32910181; PMCID: PMC7485274.
Brown SH, Banuelos K, Ward SR, Lieber RL. Architectural and morphological assessment of rat abdominal wall muscles: comparison for use as a human model. J Anat. 2010;217(3):196-202. doi: 10.1111/j.1469-7580.2010.01271.x. PubMed PMID: 20646108; PMCID: 2919595.
Brown SH, Ward SR, Cook MS, Lieber RL. Architectural analysis of human abdominal wall muscles: implications for mechanical function. Spine (Phila Pa 1976). 2011;36(5):355-62. doi: 10.1097/BRS.0b013e3181d12ed7. PubMed PMID: 21325932; PMCID: 3017737.
Bulun SE, Lin Z, Imir G, Amin S, Demura M, Yilmaz B, Martin R, Utsunomiya H, Thung S, Gurates B, Tamura M, Langoi D, Deb S. Regulation of aromatase expression in estrogen-responsive breast and uterine disease: from bench to treatment. Pharmacological reviews. 2005;57(3):359-83. doi: 10.1124/pr.57.3.6. PubMed PMID: 16109840.
Bulun SE, Price TM, Aitken J, Mahendroo MS, Simpson ER. A link between breast cancer and local estrogen biosynthesis suggested by quantification of breast adipose tissue aromatase cytochrome P450 transcripts using competitive polymerase chain reaction after reverse transcription. The Journal of clinical endocrinology and metabolism. 1993;77(6):1622-8. Epub Dec. 1, 1993. PubMed PMID: 8117355.
Bulun SE, Sharda G, Rink J, Sharma S, Simpson ER. Distribution of aromatase P450 transcripts and adipose fibroblasts in the human breast. The Journal of clinical endocrinology and metabolism. 1996;81(3):1273-7. Epub Mar. 1, 1996. PubMed PMID: 8772611.
Bulun SE, Simpson ER. Competitive reverse transcription-polymerase chain reaction analysis indicates that levels of aromatase cytochrome P450 transcripts in adipose tissue of buttocks, thighs, and abdomen of women increase with advancing age. The Journal of clinical endocrinology and metabolism. 1994;78(2):428-32. Epub Feb. 1, 1994. doi: 10.1210/jcem.78.2.8106632. PubMed PMID: 8106632.
Bulun SE. Aromatase deficiency and estrogen resistance: from molecular genetics to clinic. Seminars in reproductive medicine. 2000;18(1):31-9. PubMed PMID: 11305285.
Burrows H. The occurrence of scrotal hernia in mice under treatment with oestrin. British Journal of Surgery. 1934;21:6.
Chapman MA, Meza R, Lieber RL. Skeletal muscle fibroblasts in health and disease. Differentiation. 2016;92(3):108-15. doi: 10.1016/j.diff.2016.05.007. PubMed PMID: 27282924; PMCID: 5079803.
Chapman MA, Mukund K, Subramaniam S, Brenner D, Lieber RL. Three distinct cell populations express extracellular matrix proteins and increase in number during skeletal muscle fibrosis. Am J Physiol Cell Physiol. 2017;312(2):C131-C43. doi: 10.1152/ajpcell.00226.2016. PubMed PMID: 27881411; PMCID: 5336596.
Chappell PE, Lydon JP, Conneely OM, O'Malley BW, Levine JE. Endocrine defects in mice carrying a null mutation for the progesterone receptor gene. Endocrinology. 1997;138(10):4147-52. Epub Oct. 10, 1997. doi: 10.1210/endo.138.10.5456. PubMed PMID: 9322923.
Chen D, Reierstad S, Fang F, Bulun SE. JunD and JunB integrate prostaglandin E2 activation of breast cancer-associated proximal aromatase promoters. Mol Endocrinol. 2011;25(5):767-75. doi: 10.1210/me.2010-0368. PubMed PMID: 21393445; PMCID: 3082330.
Chen D, Reierstad S, Lin Z, Lu M, Brooks C, Li N, Innes J, Bulun SE. Prostaglandin E(2) induces breast cancer related aromatase promoters via activation of p38 and c-Jun NH(2)-terminal kinase in adipose fibroblasts. Cancer research. 2007;67(18):8914-22. Epub Sep. 19, 2007. doi: 10.1158/0008-5472.CAN-06-4751. PubMed PMID: 17875734.
Chen D, Zhao H, Coon JSt, Ono M, Pearson EK, Bulun SE. Weight gain increases human aromatase expression in mammary gland. Mol Cell Endocrinol. 2012;355(1):114-20. Epub Feb. 22, 2012. doi: 10.1016/j.mce.2012.01.027. PubMed PMID: 22342815; PMCID: 3312968.
Critchley HOD, Chodankar RR. 90 Years of Progesterone: Selective progesterone receptor modulators in gynaecological therapies. Journal of molecular endocrinology. 2020;65(1):T15-T33. Epub Jul. 1, 2020. doi: 10.1530/JME-19-0238. PubMed PMID: 32599565; PMCID: PMC7354704.
De Ronde W, de Jong FH. Aromatase inhibitors in men: effects and therapeutic options. Reprod Biol Endocrinol. 2011;9:93. Epub Jun. 23, 2011. doi: 10.1186/1477-7827-9-93. PubMed PMID: 21693046; PMCID: PMC3143915.
Deb S, Jianfeng Z, Amin SA, Gonca IA, Bertan YM, Zihong L, Bulun SE. A novel role of sodium butyrate in the regulation of cancer-associated aromatase promoters I.3 and II by disrupting a transcriptional complex in breast adipose fibroblasts. J Biol Chem. 2006;281(5):2585-97. PubMed PMID: 16303757.
DeMayo FJ, Lydon JP. 90 Years of Progesterone: New insights into progesterone receptor signaling in the endometrium required for embryo implantation. Journal of molecular endocrinology. 2020;65(1):T1-T14. Epub Dec. 7, 2019. doi: 10.1530/JME-19-0212. PubMed PMID: 31809260; PMCID: PMC7261627.
Dimitrov NV, Colucci P, Nagpal S. Some aspects of the endocrine profile and management of hormone-dependent male breast cancer. Oncologist. 2007;12(7):798-807. Epub Aug. 4, 2007. doi: 10.1634/theoncologist.12-7-798. PubMed PMID: 17673611.
Dryad Digital Repository. Brain Aromatase is Essential for Regulation of Sexual Activity in Male Mice [Internet]. Available from: https://doi.org/10.5061/dryad.5mkkwh72t.
Duttke SH, Chang MW, Heinz S, Benner C. Identification and dynamic quantification of regulatory elements using total RNA. Genome research. 2019;29(11):1836-46. Epub Oct. 28, 2019. doi: 10.1101/gr.253492.119. PubMed PMID: 31649059; PMCID: PMC6836739.
Dyson MT, Roqueiro D, Monsivais D, Ercan CM, Pavone ME, Brooks DC, Kakinuma T, Ono M, Jafari N, Dai Y, Bulun SE. Genome-wide DNA methylation analysis predicts an epigenetic switch for GATA factor expression in endometriosis. PLoS genetics. 2014;10(3):e1004158. doi: 10.1371/journal.pgen. 1004158. PubMed PMID: 24603652; PMCID: 3945170.
Fatima LA, Campello RS, Santos RS, Freitas HS, Frank AP, Machado UF, Clegg DJ. Estrogen receptor 1 (ESR1) regulates

(56) References Cited

OTHER PUBLICATIONS

VEGFA in adipose tissue. Sci Rep. 2017;7(1):16716. doi: 10.1038/s41598-017-16686-7. PubMed PMID: 29196658; PMCID: 5711936.
Fernandez-Valdivia R, Jeong J, Mukherjee A, Soyal SM, Li J, Ying Y, Demayo FJ, Lydon JP. A mouse model to dissect progesterone signaling in the female reproductive tract and mammary gland. Genesis. 2010;48(2):106-13. Epub Dec. 24, 2009. doi: 10.1002/dvg.20586. PubMed PMID: 20029965; PMCID: PMC2819579.
Gao S, Dai Y, Rehman J. A Bayesian inference transcription factor activity model for the analysis of single-cell transcriptomes. Genome research. 2021;31(7):1296-311. Epub Jul. 2, 2021. doi: 10.1101/gr.265595.120. PubMed PMID: 34193535; PMCID: PMC8256867.
Gao S, Rehman J, Dai Y. Assessing comparative importance of DNA sequence and epigenetic modifications on gene expression using a deep convolutional neural network. Comput Struct Biotechnol J. 2022;20:3814-23. Epub Jul. 28, 2022. doi: 10.1016/j.csbj.2022.07.014. PubMed PMID: 35891778; PMCID: PMC9307602.
Gardner WU. Sexual dimorphism of the pelvis of the mouse, the effect of estrogenic hormones upon the pelvis and upon the development of scrotal hernias. American Journal of Anatomy. 1936;59:25.
Gianetta E, de Cian F, Cuneo S, Friedman D, Vitale B, Marinari G, Baschieri G, Camerini G. Hernia repair in elderly patients. Br J Surg. 1997;84(7):983-5. PubMed PMID: 9240142.
Gilbert AI. Hernia repair in the aged and infirmed. J Fla Med Assoc. 1988;75(11):742-4. PubMed PMID: 3204359.
Gillies AR, Bushong EA, Deerinck TJ, Ellisman MH, Lieber RL. Three-dimensional reconstruction of skeletal muscle extracellular matrix ultrastructure. Microsc Microanal. 2014;20(6):1835-40. doi: 10.1017/S1431927614013300. PubMed PMID: 25275291; PMCID: 4267978.
Gillies AR, Chapman MA, Bushong EA, Deerinck TJ, Ellisman MH, Lieber RL. High resolution three-dimensional reconstruction of fibrotic skeletal muscle extracellular matrix. J Physiol. 2017;595(4):1159-71. doi: 10.1113/JP273376. PubMed PMID: 27859324; PMCID: 5309386.
Gillies AR, Lieber RL. Structure and function of the skeletal muscle extracellular matrix. Muscle Nerve. 2011;44(3):318-31. doi: 10.1002/mus.22094. PubMed PMID: 21949456; PMCID: 3177172.
Goad J, Rudolph J, Zandigohar M, Tae M, Dai Y, Wei JJ, Bulun SE, Chakravarti D, Rajkovic A. Single-cell sequencing reveals novel cellular heterogeneity in uterine leiomyomas. Hum Reprod. 2022;37(10):2334-49. Epub Aug. 25, 2022. doi: 10.1093/humrep/deac183. PubMed PMID: 36001050; PMCID: PMC9802286.
Grant RA. Estimation of Hydroxyproline by the Autoanalyser. Journal of clinical pathology. 1964;17:685-6. PubMed PMID: 14227441; PMCID: 480859.
Guan J, Zhou W, Hafner M, Blake RA, Chalouni C, Chen IP, De Bruyn T, Giltnane JM, Hartman SJ, Heidersbach A, Houtman R, Ingalla E, Kategaya L, Kleinheinz T, Li J, Martin SE, Modrusan Z, Nannini M, Oeh J, Ubhayakar S, Wang X, Wertz IE, Young A, Yu M, Sampath D, Hager JH, Friedman LS, Daemen A, Metcalfe C. Therapeutic Ligands Antagonize Estrogen Receptor Function by Impairing Its Mobility. Cell. 2019;178(4):949-63 e18. Epub Jul. 30, 2019. doi: 10.1016/j.cell.2019.06.026. PubMed PMID: 31353221.
Gunnarsson U, Degerman M, Davidsson A, Heuman R. Is elective hernia repair worthwhile in old patients? Eur J Surg. 1999;165(4):326-32. doi: 10.1080/110241599750006857. PubMed PMID: 10365833.
Hamilton KJ, Arao Y, Korach KS. Estrogen hormone physiology: reproductive findings from estrogen receptor mutant mice. Reprod Biol. 2014;14(1):3-8. Epub Mar. 13, 2014. doi: 10.1016/j.repbio.2013.12.002. PubMed PMID: 24607249; PMCID: PMC4777324.
Hao Y, Hao S, Andersen-Nissen E, Mauck WM, 3rd, Zheng S, Butler A, Lee MJ, Wilk AJ, Darby C, Zager M, Hoffman P, Stoeckius M, Papalexi E, Mimitou EP, Jain J, Srivastava A, Stuart T, Fleming LM, Yeung B, Rogers AJ, McElrath JM, Blish CA, Gottardo R, Smibert P, Satija R. Integrated analysis of multimodal single-cell data. Cell. 2021; 184(13):3573-87 e29. Epub Jun. 2, 2021. doi: 10.1016/j.cell.2021.04.048. PubMed PMID: 34062119; PMCID: PMC8238499.
Harrington WR, Sheng S, Barnett DH, Petz LN, Katzenellenbogen JA, Katzenellenbogen BS. Activities of estrogen receptor alpha- and beta-selective ligands at diverse estrogen responsive gene sites mediating transactivation or transrepression. Mol Cell Endocrinol. 2003;206(1-2):13-22. PubMed PMID: 12943986.
Hazary S, Gardner WU. Influence of sex hormones on abdominal musculature and the formation of inguinal and scrotal hernias in mice. Anat Rec. 1960; 136:437-43. PubMed PMID: 14400391.
Welboren WJ, van Driel MA, Janssen-Megens EM, van Heeringen SJ, Sweep FC, Span PN, Stunnenberg HG. ChIP—Seq of ERalpha and RNA polymerase II defines genes differentially responding to ligands. EMBO J. 2009;28(10):1418-28. doi: 10.1038/emboj.2009.88. PubMed PMID: 19339991; PMCID: 2688537.
Xu J, Liu S, Yin P, Bulun S, Dai Y. MeDEStrand: an improved method to infer genome-wide absolute methylation levels from DNA enrichment data. BMC Bioinformatics. 2018;19(1):540. Epub Dec. 24, 2018. doi: 10.1186/s12859-018-2574-7. PubMed PMID: 30577750; PMCID: PMC6303941.
Yadav S, Giridhar KV, Leone JP, Leon-Ferre RA, Ruddy KJ. A practical guide to endocrine therapy in the management of estrogen receptor-positive male breast cancer. Breast Cancer Manag. 2021;10(3). doi: ARTN BMT59 10.2217/bmt-2021-0001. PubMed PMID: WOS:000693205600001.
Yan F, Powell DR, Curtis DJ, Wong NC. From reads to insight: a hitchhiker's guide to ATAC-seq data analysis. Genome Biol. 2020;21(1):22. Epub Feb. 6, 2020. doi: 10.1186/s13059-020-1929-3. PubMed PMID: 32014034; PMCID: PMC6996192.
Yang B, Jiang ZP, Li YR, Zong Z, Chen S. Long-term outcome for open preperitoneal mesh repair of recurrent inguinal hernia. International journal of surgery. 2015;19:134-6. doi: 10.1016/j.ijsu.2015.05.029. PubMed PMID: 26021274.
Yang CF, Chiang MC, Gray DC, Prabhakaran M, Alvarado M, Juntti SA, Unger EK, Wells JA, Shah NM. Sexually dimorphic neurons in the ventromedial hypothalamus govern mating in both sexes and aggression in males. Cell. 2013;153(4):896-909. Epub May 15, 2013. doi: 10.1016/j.cell.2013.04.017. PubMed PMID: 23663785; PMCID: PMC3767768.
Yang T, Bayless DW, Wei Y, Landayan D, Marcelo IM, Wang Y, DeNardo LA, Luo L, Druckmann S, Shah NM. Hypothalamic neurons that mirror aggression. Cell. 2023;186(6):1195-211 e19. Epub Feb. 17, 2023. doi: 10.1016/j.cell.2023.01.022. PubMed PMID: 36796363; PMCID: PMC10081867.
Yang T, Yang CF, Chizari MD, Maheswaranathan N, Burke KJ, Jr., Borius M, Inoue S, Chiang MC, Bender KJ, Ganguli S, Shah NM. Social Control of Hypothalamus-Mediated Male Aggression. Neuron. 2017;95(4):955-70 e4. Epub Aug. 2, 2017. doi: 10.1016/j.neuron.2017.06.046. PubMed PMID: 28757304; PMCID: PMC5648542.
Yilmaz BD, Sison CAM, Yildiz S, Miyazaki K, Coon VJ, Yin P, Bulun SE. Genome-wide estrogen receptor-alpha binding and action in human endometrial stromal cells. F S Sci. 2020;1(1):59-66. Epub Aug. 1, 2020. doi: 10.1016/j.xfss.2020.06.002. PubMed PMID: 35559740.
Yin P, Roqueiro D, Huang L, Owen JK, Xie A, Navarro A, Monsivais D, Coon JSt, Kim JJ, Dai Y, Bulun SE. Genome-wide progesterone receptor binding: cell type-specific and shared mechanisms in T47D breast cancer cells and primary leiomyoma cells. PloS one. 2012;7(1): e29021. Epub Jan. 25, 2012. doi: 10.1371/journal.pone.0029021. PubMed PMID: 22272226; PMCID: 3260146.
Zhang W, Schmull S, Du M, Liu J, Lu Z, Zhu H, Xue S, Lian F. Estrogen Receptor alpha and beta in Mouse: Adipose-Derived Stem Cell Proliferation, Migration, and Brown Adipogenesis In Vitro. Cell Physiol Biochem. 2016;38(6):2285-99. doi: 10.1159/000445583. PubMed PMID: 27197672.
Zhao H, Cui Y, Dupont J, Sun H, Hennighausen L, Yakar S. Overexpression of the tumor suppressor gene phosphatase and tensin homologue partially inhibits wnt-1-induced mammary tumorigenesis. Cancer research. 2005;65(15):6864-73. Epub Aug. 3, 2005. doi: 10.1158/0008-5472.CAN-05-0181. PubMed PMID: 16061670.
Zhao H, Innes J, Brooks DC, Reierstad S, Yilmaz MB, Lin Z, Bulun SE. A novel promoter controls Cyp19a1 gene expression in mouse

(56) References Cited

OTHER PUBLICATIONS adipose tissue. Reprod Biol Endocrinol. 2009;7:37. Epub Apr. 28, 2009. doi: 10.1186/1477-7827-7-37. PubMed PMID: 19393092; PMCID: 2684739.
Zhao H, Pearson EK, Brooks DC, Coon JSt, Chen D, Demura M, Zhang M, Clevenger CV, Xu X, Veenstra TD, Chatterton RT, DeMayo FJ, Bulun SE. A humanized pattern of aromatase expression is associated with mammary hyperplasia in mice. Endocrinology. 2012;153(6):2701-13. Epub Apr. 18, 2012. doi: 10.1210/en.2011-1761. PubMed PMID: 22508516; PMCID: 3359608.
Zhao H, Zhou L, Li L, Coon VJ, Chatterton RT, Brooks DC, Jiang E, Liu L, Xu X, Dong Z, DeMayo FJ, Stulberg JJ, Tourtellotte WG, Bulun SE. Shift from androgen to estrogen action causes abdominal muscle fibrosis, atrophy, and inguinal hernia in a transgenic male mouse model. Proc Natl Acad Sci U S A. 2018;115(44):E10427-E36. doi: 10.1073/pnas.1807765115. PubMed PMID: 30327348; PMCID: 6217386.
Zhou J, Gurates B, Yang S, Sebastian S, Bulun SE. Malignant breast epithelial cells stimulate aromatase expression via promoter II in human adipose fibroblasts: an epithelial-stromal interaction in breast tumors mediated by CCAAT/enhancer binding protein beta. Cancer research. 2001;61(5):2328-34. PubMed PMID: 11280806.
Potluri T, et al. Estrogen receptor-$\alpha$ ablation reverses muscle fibrosis and inguinal hernias. J Clin Invest. 2025. 2025;135(6):e179137.
You T, et al. Role of progesterone action in inguinal hernia formation via skeletal muscle fibrosis and atrophy. JCI Insight. 2025;10(14):e193208.
Hellspong G, Gunnarsson U, Dahlstrand U, Sandblom G. Diabetes as a risk factor in patients undergoing groin hernia surgery. Langenbecks Arch Surg. 2017;402(2):219-25. doi: 10.1007/s00423-016-1519-8. PubMed PMID: 27928640.
Hemsell DL, Grodin JM, Brenner PF, Siiteri PK, MacDonald PC. Plasma precursors of estrogen. II. Correlation of the extent of conversion of plasma androstenedione to estrone with age. The Journal of clinical endocrinology and metabolism. 1974;38(3):476-9. Epub Mar. 1, 1974. doi: 10.1210/jcem-38-3-476. PubMed PMID: 4815174.
Henderson VW. Progesterone and human cognition. Climacteric. 2018;21(4):333-40. Epub Jun. 2, 2018. doi: 10.1080/13697137.2018.1476484. PubMed PMID: 29852783; PMCID: PMC6309195.
HerniaSurge G. International guidelines for groin hernia management. Hernia : the journal of hernias and abdominal wall surgery. 2018;22(1):1-165. doi: 10.1007/s10029-017-1668-x. PubMed PMID: 29330835; PMCID: 5809582.
Ishikawa H, Ishi K, Serna VA, Kakazu R, Bulun SE, Kurita T. Progesterone is essential for maintenance and growth of uterine leiomyoma. Endocrinology. 2010;151(6):2433-42. doi: 10.1210/en.2009-1225. PubMed PMID: 20375184; PMCID: 2875812.
Islam MS, Afrin S, Jones SI, Segars J. Selective Progesterone Receptor Modulators-Mechanisms and Therapeutic Utility. Endocr Rev. 2020;41(5). Epub May 5, 2020. doi: 10.1210/endrev/bnaa012. PubMed PMID: 32365199; PMCID: PMC8659360.
Jenkins JT, O'Dwyer PJ. Inguinal hernias. BMJ. 2008;336(7638):269-72: doi: 10.1136/bmj.39450.428275.AD. PubMed PMID: 18244999; PMCID: 2223000.
Ji Y, Rankin C, Grunberg S, Sherrod AE, Ahmadi J, Townsend JJ, Feun LG, Fredericks RK, Russell CA, Kabbinavar FF, Stelzer KJ, Schott A, Verschraegen C. Double-Blind Phase III Randomized Trial of the Antiprogestin Agent Mifepristone in the Treatment of Unresectable Meningioma: SWOG S9005. Journal of clinical oncology : official journal of the American Society of Clinical Oncology. 2015;33(34):4093-8. Epub Nov. 4, 2015. doi: 10.1200/JCO.2015.61.6490. PubMed PMID: 26527781; PMCID: PMC4669593 online at www.jco.org.
Kalluri R. The biology and function of fibroblasts in cancer. Nat Rev Cancer. 2016;16(9):582-98. doi: 10.1038/nrc.2016.73. PubMed PMID: 27550820.
Kim JJ, Kurita T, Bulun SE. Progesterone action in endometrial cancer, endometriosis, uterine fibroids, and breast cancer. Endocr Rev. 2013;34(1):130-62. doi: 10.1210/er.2012-1043. PubMed PMID: 23303565; PMCID: 3565104.
Kingsnorth A, LeBlanc K. Hernias: inguinal and incisional. Lancet. 2003;362(9395):1561-71. doi: 10.1016/S0140-6736(03)14746-0. PubMed PMID: 14615114.
Lamb CA, Helguero LA, Giulianelli S, Soldati R, Vanzulli SI, Molinolo A, Lanari C. Antisense oligonucleotides targeting the progesterone receptor inhibit hormone-independent breast cancer growth in mice. Breast cancer research : BCR. 2005;7(6): R1111-21. Epub Feb. 7, 2006. doi: 10.1186/bcr1345. PubMed PMID: 16457691; PMCID: PMC1410760.
Langmead B, Trapnell C, Pop M, Salzberg SL. Ultrafast and memory-efficient alignment of short DNA sequences to the human genome. Genome Biol. 2009;10(3):R25. Epub Mar. 6, 2009. doi: 10.1186/GB-2009-10-3-r25. PubMed PMID: 19261174; PMCID: PMC2690996.
Lee O, Bosland MC, Wang M, Shidfar A, Hosseini O, Xuei X, Patel P, Schipma MJ, Helenowski I, Kim JJ, Clare SE, Khan SA. Selective progesterone receptor blockade prevents BRCA1-associated mouse mammary tumors through modulation of epithelial and stromal genes. Cancer Lett. 2021;520:255-66. Epub Jul. 31, 2021. doi: 10.1016/j.canlet.2021.07.034. PubMed PMID: 34329741.
Lewis JH, Cottu PH, Lehr M, Dick E, Shearer T, Rencher W, Bexon AS, Campone M, Varga A, Italiano A. Onapristone Extended Release: Safety Evaluation from Phase I-II Studies with an Emphasis on Hepatotoxicity. Drug Saf. 2020;43(10):1045-55. Epub Jul. 1, 2020. doi: 10.1007/s40264-020-00964-x. PubMed PMID: 32594454; PMCID: PMC7497701.
Lieber RL, Ward SR. Cellular mechanisms of tissue fibrosis. 4. Structural and functional consequences of skeletal muscle fibrosis. Am J Physiol Cell Physiol. 2013;305(3):C241-52. doi: 10.1152/ajpcell.00173.2013. PubMed PMID: 23761627; PMCID: 3742845.
Lin Z, Yin P, Reierstad S, O'Halloran M, Coon VJ, Pearson EK, Mutlu GM, Bulun SE. Adenosine A1 receptor, a target and regulator of estrogen receptoralpha action, mediates the proliferative effects of estradiol in breast cancer. Oncogene. 2010;29(8):1114-22. Epub Nov. 26, 2009. doi: 10.1038/onc.2009.409. PubMed PMID: 19935720; PMCID: 2829108.
Liu S, Yin P, Kujawa SA, Coon JSt, Okeigwe I, Bulun SE. Progesterone receptor integrates the effects of mutated MED12 and altered DNA methylation to stimulate RANKL expression and stem cell proliferation in uterine leiomyoma. Oncogene. 2019;38(15):2722-35. Epub Dec. 13, 2018. doi: 10.1038/s41388-018-0612-6. PubMed PMID: 30538295; PMCID: PMC6461478.
Liu S, Yin P, Xu J, Dotts AJ, Kujawa SA, Coon VJ, Zhao H, Dai Y, Bulun SE. Progesterone receptor-DNA methylation crosstalk regulates depletion of uterine leiomyoma stem cells: A potential therapeutic target. Stem Cell Reports. 2021;16(9):2099-106. Epub Aug. 14, 2021. doi: 10.1016/j.stemcr.2021.07.013. PubMed PMID: 34388365; PMCID: PMC8452515.
Liu S, Yin P, Xu J, Dotts AJ, Kujawa SA, Coon VJ, Zhao H, Shilatifard A, Dai Y, Bulun SE. Targeting DNA Methylation Depletes Uterine Leiomyoma Stem Cell-enriched Population by Stimulating Their Differentiation. Endocrinology. 2020;161(10). Epub Aug. 20, 2020. doi: 10.1210/endocr/bqaa143. PubMed PMID: 32812024; PMCID: PMC7497820.
Longcope C, Pratt JH, Schneider SH, Fineberg SE. Aromatization of androgens by muscle and adipose tissue in vivo. The Journal of clinical endocrinology and metabolism. 1978;46(1):146-52. Epub Jan. 1, 1978. doi: 10.1210/jcem-46-1-146. PubMed PMID: 752017.
Longcope C, Pratt JH, Schneider SH, Fineberg SE. The in vivo metabolism of androgens by muscle and adipose tissue of normal men. Steroids. 1976;28(4):521-33. Epub Oct. 1, 1976. doi: 10.1016/0039-128x(76)90021-0. PubMed PMID: 1006722.
Lydon JP, DeMayo FJ, Funk CR, Mani SK, Hughes AR, Montgomery CA, Jr., Shyamala G, Conneely OM, O'Malley BW. Mice lacking progesterone receptor exhibit pleiotropic reproductive abnormalities. Genes Dev. 1995;9 (18):2266-78. Epub Sep. 15, 1995. doi: 10.1101/gad.9.18.2266. PubMed PMID: 7557380.
MacDonald PC, Rombaut RP, Siiteri PK. Plasma precursors of estrogen. I. Extent of conversion of plasma delta-4-androstenedione

(56) References Cited

OTHER PUBLICATIONS to estrone in normal males and nonpregnant normal, castrate and adrenalectomized females. The Journal of clinical endocrinology and metabolism. 1967;27(8): 1103-11. Epub Aug. 1, 1967. doi: 10.1210/jcem-27-8-1103. PubMed PMID: 6035658.

Mao Y, Chen L, Li J, Shangguan AJ, Kujawa S, Zhao H. A network analysis revealed the essential and common downstream proteins related to inguinal hernia. PloS one. 2020;15(1):e0226885. Epub Jan. 8, 2020. doi: 10.1371/journal.pone.0226885. PubMed PMID: 31910207; PMCID: PMC6946160.

Matthews RD, Anthony T, Kim LT, Wang J, Fitzgibbons RJ, Jr., Giobbie-Hurder A, Reda DJ, Itani KM, Neumayer LA, Veterans Affairs Cooperative 456 Studies Program I. Factors associated with postoperative complications and hernia recurrence for patients undergoing inguinal hernia repair: a report from the VA Cooperative Hernia Study Group. Am J Surg. 2007;194(5):611-7. doi: 10.1016/j.amjsurg.2007.07.018. PubMed PMID: 17936422.

Matthews RD, Neumayer L. Inguinal hernia in the 21st century: an evidence-based review. Curr Probl Surg. 2008;45(4):261-312. doi: 10.1067/j.cpsurg.2008.01.002. PubMed PMID: 18358264.

Mehrad M, Trejo Bittar HE, Yousem SA. Sex steroid receptor expression in idiopathic pulmonary fibrosis. Hum Pathol. 2017;66:200-5. Epub Mar. 17, 2017. doi: 10.1016/j.humpath.2017.02.012. PubMed PMID: 28300574.

Miner JN, Tyree C, Hu J, Berger E, Marschke K, Nakane M, Coghlan MJ, Clemm D, Lane B, Rosen J. A nonsteroidal glucocorticoid receptor antagonist. Mol Endocrinol. 2003;17(1):117-27. Epub Jan. 4, 2003. doi: 10.1210/me.2002-0010. PubMed PMID: 12511611.

Mohammed H, Russell IA, Stark R, Rueda OM, Hickey TE, Tarulli GA, Serandour AA, Birrell SN, Bruna A, Saadi A, Menon S, Hadfield J, Pugh M, Raj GV, Brown GD, D'Santos C, Robinson JL, Silva G, Launchbury R, Perou CM, Stingl J, Caldas C, Tilley WD, Carroll JS. Progesterone receptor modulates ERalpha action in breast cancer. Nature. 2015;523(7560):313-7. doi: 10.1038/nature14583. PubMed PMID: 26153859; PMCID: 4650274.

Nair HB, Santhamma B, Dileep KV, Binkley P, Acosta K, Zhang KYJ, Schenken R, Nickisch K. EC313—a tissue selective SPRM reduces the growth and proliferation of uterine fibroids in a human uterine fibroid tissue xenograft model. Sci Rep. 2019;9(1):17279. Epub Nov. 23, 2019. doi: 10.1038/s41598-019-53467-w. PubMed PMID: 31754172; PMCID: PMC6872653 salaried full time employees of Evestra, Inc. R.S., P.B., K.Y.J.Z. and K.V.D. declare no competing interests.

Nieman LK. Selective progesterone receptor modulators and reproductive health. Curr Opin Endocrinol Diabetes Obes. 2022;29(4):406-12. Epub Jul. 2, 2022. doi: 10.1097/MED.0000000000000753. PubMed PMID: 35776850.

Nilsson ME, Vandenput L, Tivesten A, Norlen AK, Lagerquist MK, Windahl SH, Borjesson AE, Farman HH, Poutanen M, Benrick A, Maliqueo M, Stener-Victorin E, Ryberg H, Ohlsson C. Measurement of a Comprehensive Sex Steroid Profile in Rodent Serum by High-Sensitive Gas Chromatography-Tandem Mass Spectrometry. Endocrinology. 2015;156(7):2492-502. Epub Apr. 10, 2015. doi: 10.1210/en.2014-1890. PubMed PMID: 25856427.

Ohlsson C, Langenskiold M, Smidfelt K, Poutanen M, Ryberg H, Norlen AK, Nordanstig J, Bergstrom G, Tivesten A. Low Progesterone and Low Estradiol Levels Associate With Abdominal Aortic Aneurysms in Men. The Journal of clinical endocrinology and metabolism. 2022;107(4):e1413-e25. Epub Dec. 6, 2021. doi: 10.1210/clinem/dgab867. PubMed PMID: 34865072; PMCID: PMC8947245.

Ono M, Yin P, Navarro A, Moravek MB, Coon JSt, Druschitz SA, Serna VA, Qiang W, Brooks DC, Malpani SS, Ma J, Ercan CM, Mittal N, Monsivais D, Dyson MT, Yemelyanov A, Maruyama T, Chakravarti D, Kim JJ, Kurita T, Gottardi CJ, Bulun SE. Paracrine activation of WNT/beta-catenin pathway in uterine leiomyoma stem cells promotes tumor growth. Proc Natl Acad Sci U S A. 2013;110(42):17053-8. doi: 10.1073/pnas.1313650110. PubMed PMID: 24082114; PMCID: 3801037.

Osborne CK, Wakeling A, Nicholson RI. Fulvestrant: an oestrogen receptor antagonist with a novel mechanism of action. Br J Cancer. 2004;90 Suppl 1:S2-6. doi: 10.1038/sj.bjc.6601629. PubMed PMID: 15094757; PMCID: 2750773.

Potluri T, Taylor MJ, Stulberg JJ, Lieber RL, Zhao H, Bulun SE. An estrogen-sensitive fibroblast population drives abdominal muscle fibrosis in an inguinal hernia mouse model. JCI Insight. 2022;7(9). Epub Apr. 20, 2022. doi: 10.1172/jci.insight.152011. PubMed PMID: 35439171; PMCID: PMC9090253.

Primatesta P, Goldacre MJ. Inguinal hernia repair: incidence of elective and emergency surgery, readmission and mortality. International journal of epidemiology. 1996;25(4): 835-9. PubMed PMID: 8921464.

Rochira V, Carani C. Aromatase deficiency in men: a clinical perspective. Nat Rev Endocrinol. 2009;5(10):559-68. Epub Aug. 27, 2009. doi: 10.1038/nrendo.2009.176. PubMed PMID: 19707181.

Ross-Innes CS, Stark R, Teschendorff AE, Holmes KA, Ali HR, Dunning MJ, Brown GD, Gojis O, Ellis IO, Green AR, Ali S, Chin SF, Palmieri C, Caldas C, Carroll JS. Differential oestrogen receptor binding is associated with clinical outcome in breast cancer. Nature. 2012;481(7381):389-93. Epub Jan. 6, 2012. doi: 10.1038/nature10730. PubMed PMID: 22217937; PMCID: PMC3272464.

Rutkow IM. Demographic and socioeconomic aspects of hernia repair in the United States in 2003. Surg Clin North Am. 2003;83(5):1045-51, v-vi. doi: 10.1016/S0039-6109(03)00132-4. PubMed PMID: 14533902.

Scabia V, Ayyanan A, De Martino F, Agnoletto A, Battista L, Laszlo C, Treboux A, Zaman K, Stravodimou A, Jallut D, Fiche M, Bucher P, Ambrosini G, Sflomos G, Brisken C. Estrogen receptor positive breast cancers have patient specific hormone sensitivities and rely on progesterone receptor. Nat Commun. 2022;13(1):3127. Epub Jun. 7, 2022. doi: 10.1038/s41467-022-30898-0. PubMed PMID: 35668111; PMCID: PMC9170711.

Schneider JS, Stone MK, Wynne-Edwards KE, Horton TH, Lydon J, O'Malley B, Levine JE. Progesterone receptors mediate male aggression toward infants. Proc Natl Acad Sci U S A. 2003;100(5):2951-6. Epub Feb. 26, 2003. doi: 10.1073/pnas.0130100100. PubMed PMID: 12601162; PMCID: PMC151447.

Shimizu Y, Yarborough CP, Elger W, Chwalisz K, Osawa Y. Inhibition of aromatase activity in human placental microsomes by 13-retro-antiprogestins. Steroids. 1995;60(2):234-8. Epub Feb. 1, 1995. doi: 10.1016/0039-128x(94)00043-c. PubMed PMID: 7618191.

Smith EP, Boyd J, Frank GR, Takahashi H, Cohen RM, Specker B, Williams TC, Lubahn DB, Korach KS. Estrogen resistance caused by a mutation in the estrogen-receptor gene in a man. The New England journal of medicine. 1994;331(16):1056-61. Epub Oct. 20, 1994. doi: 10.1056/NEJM199410203311604. PubMed PMID: 8090165.

Stout EP, La Clair JJ, Snell TW, Shearer TL, Kubanek J. Conservation of progesterone hormone function in invertebrate reproduction. Proc Natl Acad Sci U S A. 2010;107(26):11859-64. Epub Jun. 16, 2010. doi: 10.1073/pnas.1006074107. PubMed PMID: 20547846; PMCID: PMC2900687.

Vafashoar F, Mousavizadeh K, Poormoghim H, Haghighi A, Pashangzadeh S, Mojtabavi N. Progesterone Aggravates Lung Fibrosis in a Mouse Model of Systemic Sclerosis. Front Immunol. 2021;12:742227. Epub Dec. 17, 2021. doi: 10.3389/fimmu.2021.742227. PubMed PMID: 34912332; PMCID: PMC8667310.

Vanzulli S, Efeyan A, Benavides F, Helguero LA, Peters G, Shen J, Conti CJ, Lanari C, Molinolo A. p21, p27 and p53 in estrogen and antiprogestin-induced tumor regression of experimental mouse mammary ductal carcinomas. Carcinogenesis. 2002;23(5):749-58. Epub May 23, 2002. doi: 10.1093/carcin/23.5.749. PubMed PMID: 12016147.

Wallenstein S, Zucker CL, Fleiss JL. Some statistical methods useful in circulation research. Circ Res. 1980;47(1):1-9. Epub Jul. 1, 1980. PubMed PMID: 7379260.

Wang S, Sun H, Ma J, Zang C, Wang C, Wang J, Tang Q, Meyer CA, Zhang Y, Liu XS. Target analysis by integration of transcriptome and ChIP-seq data with BETA. Nat Protoc. 2013;8(12):2502-15. Epub Nov. 23, 2013. doi: 10.1038/nprot.2013.150. PubMed PMID: 24263090; PMCID: PMC4135175.

* cited by examiner

METHODS AND COMPOSITIONS FOR TREATING AND/OR PREVENTING HERNIAS

CROSS-REFERENCED TO RELATED PATENT APPLICATIONS

This application claims the benefit of priority under 35 U.S.C. § 119(e) to U.S. Provisional Application No. 63/609,158, filed Dec. 12, 2023. The contents of which are incorporated herein by reference in their entireties.

STATEMENT REGARDING FEDERALLY SPONSORED RESEARCH

This invention was made with government support under DK121529 awarded by The National Institutes of Health. The government has certain rights in the invention.

BACKGROUND OF THE INVENTION

More than 1 in 4 elderly men will have an inguinal hernia during their lifetime. Inguinal hernia repair is the most common general surgical procedure performed in the US today (800,000/year). Annual health care costs directly attributable to inguinal hernia exceed $2.5 billion in the US. Surgery is currently the only available treatment; however, recurrent hernias in elderly men or men with severe diabetes or liver failure present a challenge for surgeons due to the high rate of complications such as wound infection and long-term pain.

BRIEF SUMMARY OF THE INVENTION

In one aspect, a method for treating and/or preventing a hernia in a subject in need thereof is provided. The method can include administering to the subject one or more therapeutic agents that modulate the activity of progesterone and/or progesterone receptor in the subject.

In another aspect, a method for treating and/or preventing a hernia in a subject in need thereof is provided. The method can include administering to the subject one or more progesterone antagonists and/or selective progesterone receptor modulators (SPRMs), where the subject has or is at risk of developing a hernia.

BRIEF DESCRIPTION OF THE DRAWINGS

Non-limiting embodiments of the present invention will be described by way of example with reference to the accompanying figures.

FIG. 7A shows the WT mice treated with E2, P4, and RU486. P4+E2 induced large hernia formation in all WT mice (n=10). E2, P4 and/or RU486 treatment in WT mice started from 9-10 weeks old for 12 weeks. E2: Estradiol, P4: Progesterone, RU486 (Mifepristone): Progesterone antagonist or antiprogestin. $*p<0.05$. $**p<0.0001$. FIG. 7B shows the Arom$^{hum}$ mice treated with RU486 (left) and UPA (right) for hernia prevention. RU486 or UPA prevented hernia formation in Arom$^{hum}$ mice. Hernia size in RU486 or UPA-treated Arom$^{hum}$ mice during a 12-week treatment started from 3.5 weeks of age (before hernia formation). RU486 (Mifepristone) and UPA (Ulipristal acetate) are progesterone antagonists or antiprogestins. n=10. $p<0.0001$. FIG. 7C shows that inguinal hernia (arrows) is absent in RU486-treated Arom$^{hum}$ mice. FIG. 7D shows the Masson's trichrome staining showing that RU486 prevents LAM fibrosis, excessive ECM deposition or myocyte atrophy (arrows) in LAM tissue of Arom$^{hum}$ mice. FIG. 7E shows that much fewer fibroblasts with PGR IHC staining (arrows and inserts) are seen in LAM tissues of Arom$^{hum}$ mice treated with RU486 vs. placebo (n=10). $**p<0.0001$.

DETAILED DESCRIPTION OF THE INVENTION

Figure 1A:
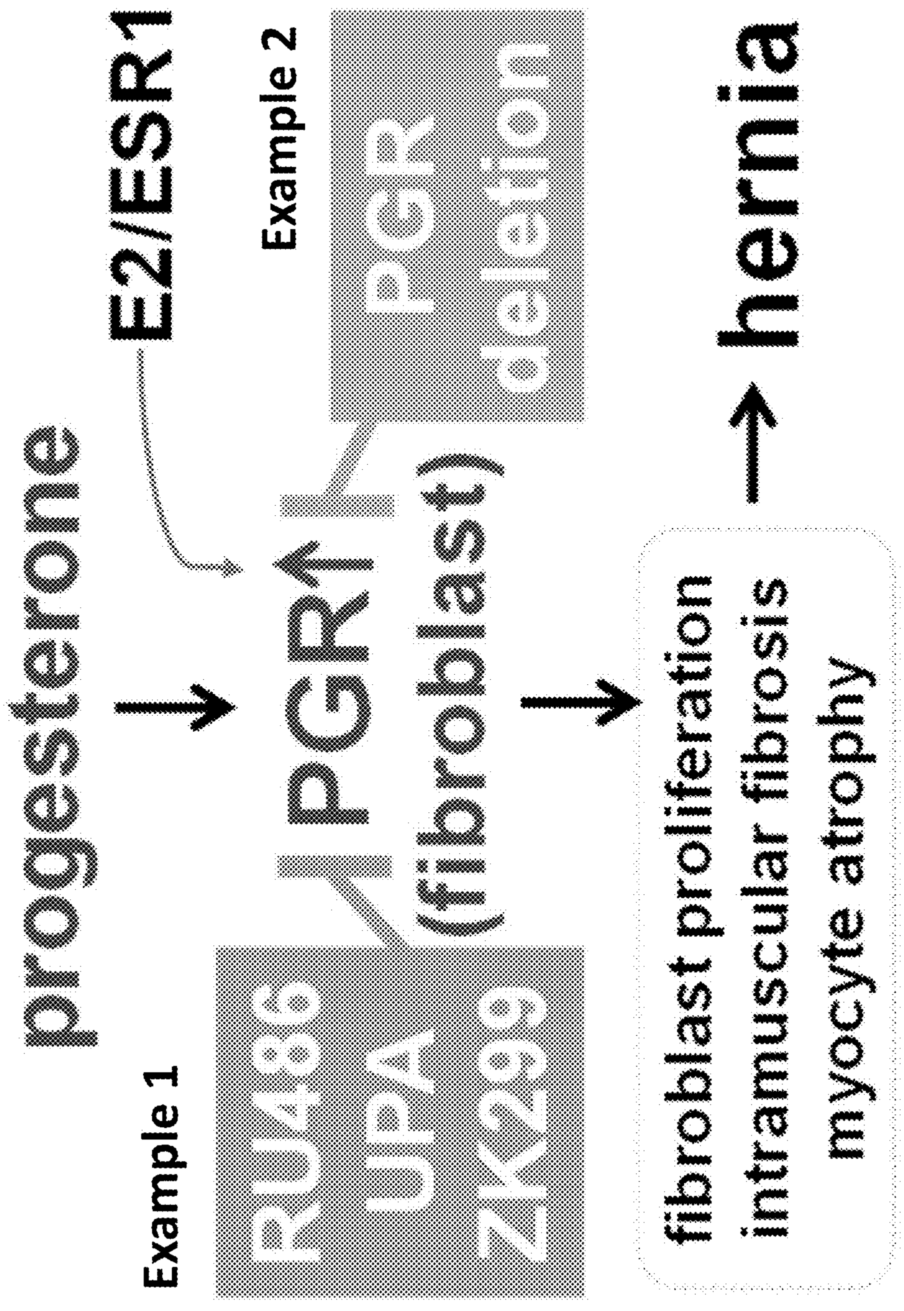
FIG. 1A schematically depicts the roles of progesterone and E2/ESR1-induced PGR in lower abdominal muscle (LAM) fibroblast proliferation, fibrosis, and hernia formation. E2: Estradiol. ESR1: Estrogen receptor α. PGR: Progesterone receptor. RU486 (Mifepristone), UPA (Ulipristal acetate), and ZK299 (Onapristone) are progesterone antagonists or antiprogestins.

Inguinal hernia is highly prevalent, occurring in more than 1 in 4 elderly men, and inguinal hernia repair is among the most frequently performed surgeries in the US. The presently disclosed technology provides methods and composition for the treatment or prevention of hernias in subjects in need thereof. The disclosed compounds and methods may be utilized to prevent skeletal muscle fibrosis and/or hernia, such as inguinal hernia, in subjects in need. Moreover, the compounds and methods may be used to halt further hernia progression.

The progesterone receptor, the key mediator of estrogen/estrogen receptor-α (ESR1) action, is exclusively expressed in lower abdominal muscle (LAM) fibroblasts in mice that express human aromatase enzyme (Arom$^{hum}$ mice) and in human hernia tissues. As discussed herein, various progesterone/progesterone receptor antagonists and/or selective progesterone receptor modulators (SPRMs) can prevent hernia development and maintain normal LAM anatomy in estrogen-rich Arom$^{hum}$ mice. Various progesterone antagonists and/or SPRMs can halt the progression of small/medium-sized hernias in these high estrogen-producing mice, in aspects. In various aspects, the progesterone antagonists and/or SPRMs can be present in the therapeutic compositions disclosed herein.

In various aspects, the methods and compositions disclosed herein can be used to treat and/or prevent hernias in a subject in need thereof. In one or more aspects, the methods can include administering to a subject a therapeutic composition that modulates the activity of progesterone and/or the progesterone receptor in the subject.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, a "subject" may be interchangeable with "patient" or "individual" and means an animal, which may be a human or non-human animal, in need of treatment, for example, treatment by include administering a therapeutic amount of one or more therapeutic agents that modulate the production and/or activity of progesterone and/or the progesterone receptor in a subject.

A "subject in need of treatment or prevention of a hernia" or "a subject in need" may include a subject having or at risk for developing a hernia. In particular, a subject in need of treatment or prevention of a hernia may include a subject having or at risk for developing a hernia selected from one or more of an inguinal hernia, a femoral hernia, an umbilical hernia, a hiatal hernia, diastasis recti, and/or an incisional hernia.

The subject in need may be an elderly man. As used herein, an "elderly man" is a human subject assigned male at birth and at least 62 years old. Suitably, the elderly male may have an age between 62 and 100 years old or any age therebetween. Administration to elderly men above the age of 100 years old is also contemplated. Elderly men have increased aromatase and thus increased estrogen formation in their lower abdominal skeletal muscle tissue. Because long-term treatment of men with the compounds, such as progesterone antagonists such as mifepristone, is well tolerated. The disclosed compounds and methods may provide interventional strategies to prevent or halt hernia development or provide an adjuvant treatment option in this high-risk population.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art. In the disclosed methods, a subject in need thereof may be administered an effective amount of a therapeutic agent for treating and/or preventing a hernia in the subject.

The disclosed therapeutic agents may be effective for modulating the production and/or activity of progesterone and/or the progesterone receptor in a subject. As disclosed herein, the term "modulation" may include increasing production (and/or concentration) and/or activity of the progesterone and/or the progesterone receptor in a subject, or conversely, decreasing production and/or activity of progesterone and/or the progesterone receptor in a subject. For example, modulation of activity of progesterone and/or the progesterone receptor in a subject may include blocking or reducing the ability for progesterone to bind to the progesterone receptor, thereby altering the activity of the progesterone receptor. Modulation of production and/or activity of progesterone and/or the progesterone receptor in a subject may include administering one or more progesterone antagonists, SPRMs, and/or antiprogestins to the subject.

The therapeutic agents utilized in the methods disclosed herein may be formulated as pharmaceutical compositions that include: (a) a therapeutically effective amount of one or more of the therapeutic agents as disclosed herein; and (b) one or more pharmaceutically acceptable carriers, excipients, or diluents.

The disclosed subject matter relates to methods and compositions for modulating the activity of progesterone and/or the progesterone receptor in a subject in need. In various aspects, the subject can have a hernia or is at risk of developing a hernia. In one or more aspects, the hernia can be one or more of an inguinal hernia, a femoral hernia, an umbilical hernia, a hiatal hernia, an incisional hernia, or diastasis recti. In certain non-limiting aspects, the hernia can be an inguinal hernia.

In certain aspects, the compositions for modulating the activity of progesterone and/or the progesterone receptor in a subject in need can include a therapeutic agent. In various aspects, the therapeutic agent can include one or more progesterone antagonists, SPRMs, and/or antiprogestins. In certain aspects, example progesterone antagonists can include, but are not limited to, one or more of mifepristone, ulipristal acetate, onapristone, and asoprisnil.

In various aspects, the therapeutic agent and/or composition can be administered to the subject locally, topically, orally, systemically, via injection, or any other suitable route. In certain aspects, the therapeutic agent and/or composition can be administered to the subject at a site of a hernia and/or at a site at risk of developing a hernia.

In one or more aspects, the subject may have undergone surgery for hernia repair or the subject is preparing to undergo surgery for hernia repair and the therapeutic agent and/or composition is administered to the subject before, during, or after the surgery.

In various aspects, the subject may have undergone surgery for hernia repair or the subject is preparing to undergo surgery for hernia repair and the therapeutic agent and/or composition can be present in an implantable material that is implanted in the subject at the site of the hernia or at a site at risk of developing into a hernia. In one non limiting aspect, the implantable material can be a hernia repair material, such as a mesh material.

The following Examples are illustrative and should not be interpreted to limit the scope of the claimed subject matter.

EXAMPLES

More than 1 in 4 elderly men will have an inguinal hernia during their lifetime[1-3]. Inguinal hernia repair is the most common general surgical procedure performed in the US today (800,000/year)[2, 4-6]. Annual health care costs directly attributable to inguinal hernia exceed $2.5 billion in the US[7]. Surgery is currently the only available treatment; however, recurrent hernias in elderly men or men with severe diabetes or liver failure present a challenge for surgeons due to the high rate of complications such as wound infection and long-term pain[8-14]. Their strikingly high prevalence, combined with poor surgical outcomes for those with recurrent hernias, reveals a significant need for alternative therapeutic strategies in high-risk populations. The mechanisms of inguinal hernia development in elderly men are not clearly understood and possibly multifactorial[15-18], thus complicating the discovery of novel preventive or therapeutic strategies. Until 2018[19], there were no clinically relevant animal models of inguinal hernia for mechanistic investigation or drug development.

Aromatase is the key enzyme for estrogen biosynthesis via conversion of testosterone to estradiol (E2) in males[20, 21]. E2 binds to estrogen receptor-α (ERα/ESR1 encoded by the Esr1 gene) that is uniquely and highly expressed in lower abdominal muscle (LAM) fibroblasts (FIG. 1B). Compared with other muscle groups, LAM tissue fibroblasts uniquely express high levels of estrogen receptor-α (ESR1). LAM tissue, where hernias occur (FIG. 2), is composed of layers of oblique and transverse skeletal muscle made of myofibers (myocytes) and surrounding stromal tissue (endomysium, perimysium, and epimysium) composed of a mixture of well-organized fibroblasts and extracellular matrix (ECM)[22]. Aromatase is expressed in the skeletal muscle in humans, but not mice. To understand the functional significance of E2 in LAM, humanized aromatase (Arom$^{hum}$) male mice that express the human aromatase gene in skeletal muscle were generated; these mice show LAM fibroblast proliferation, fibrosis, and muscle weakness characterized by progressive replacement of atrophic myocytes with ESR1-rich fibroblasts, eventually causing mechanical weakening and formation of large inguinal hernias[19, 22]. Thus, local production of E2 via aromatase activity in a particularly E2-sensitive LAM tissue leads to pathological changes and inguinal hernia formation, similar to inguinal hernias that develop in a subset of elderly men (FIG. 2B, 2C)[19,22]. These findings are consistent with earlier literature (1934-1960) reporting that exogenous estrogen caused inguinal hernias accompanied by the atrophy of LAM fibers in about half of the adult wild-type (WT) mice[23-25]. It was further found that administration of an aromatase inhibitor or E2/ESR1 antagonists or selective ablation of ESR1 in fibroblasts prevents or reverses LAM tissue fibrosis and hernias and restores normal muscle histology in Arom$^{hum}$ mice (FIG. 3)[19]. However, side effects associated with anti-E2/ESR1 treatments (e.g., sexual dysfunction or osteoporosis) obviate their long-term use in men[26-32]. Thus, it was imperative to define the specific and major downstream effectors of the E2/ESR1 signaling, which may have high translational potential. We used single-cell (sc)RNA-seq analysis of Arom$^{hum}$ LAM tissues and found that progesterone (P4) receptor (PGR, encoded by the Pgr gene), a major E2/ESR1 downstream gene, was exclusively expressed in the LAM ESR1-rich fibroblasts of Arom$^{hum}$ mice[22]. P4, the only native PGR ligand, is present at steady-state levels in the mouse circulation and in LAM tissue (FIG. 6)[33].

Figure 1B:
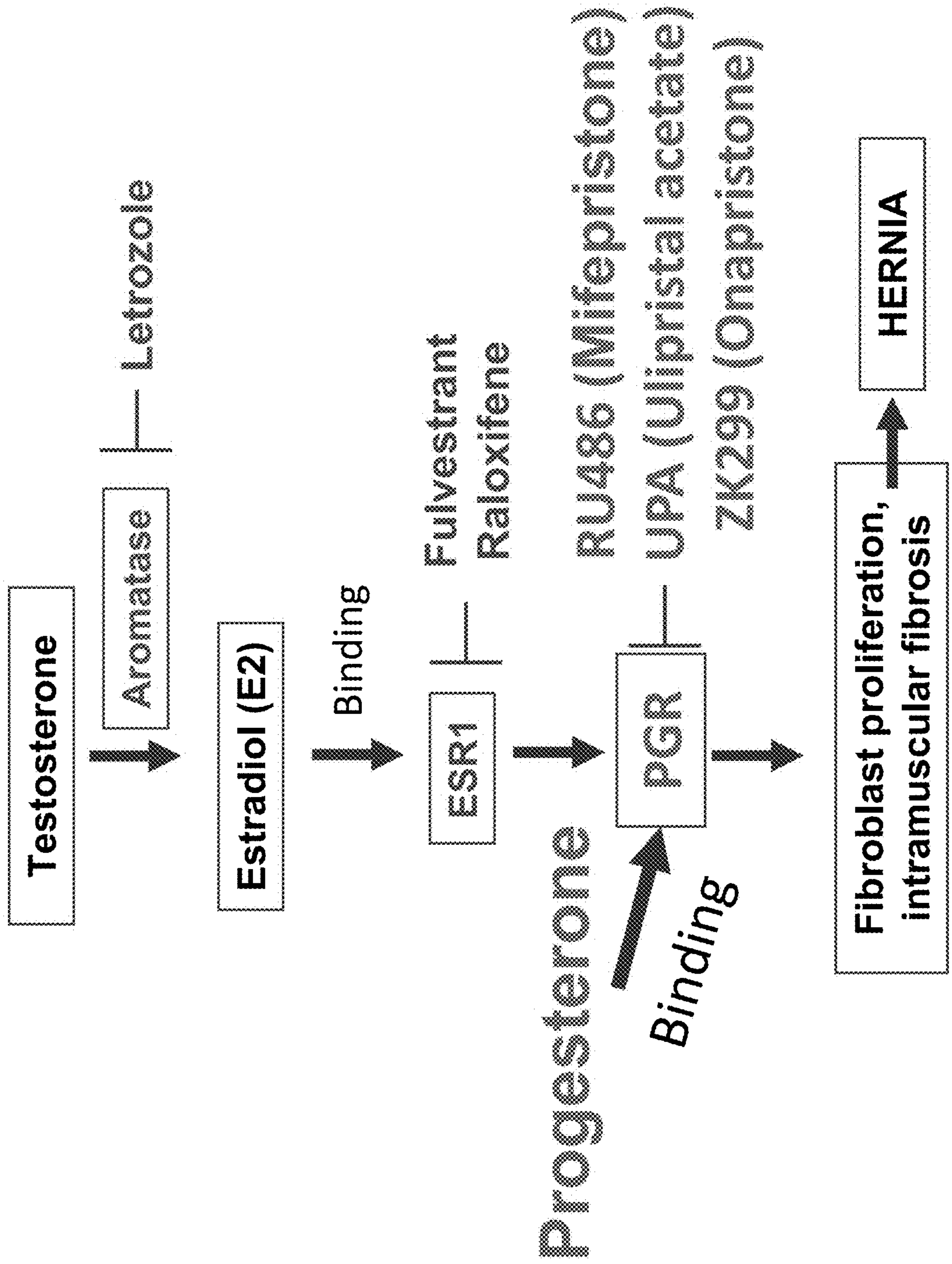
FIG. 1B schematically depicts the roles of various sex steroid hormones and hormone receptors in hernia formation, and includes the actions of various antagonists and/or antiprogestins. ESR1: Estrogen receptor α. PGR: Progesterone receptor. Letrozole is an aromatase enzyme inhibitor. Fulvestrant and raloxifene are E2/ESR1 antagonists. RU486 (Mifepristone), UPA (Ulipristal acetate), and ZK299 (Onapristone) are progesterone antagonists or antiprogestin.

It is hypothesized that enhanced P4/PGR signaling in highly P4-sensitive LAM tissues drives LAM fibroblast proliferation, fibrosis, and myocyte atrophy and that blocking P4/PGR signaling by treating Arom$^{hum}$ mice with a variety of PGR-selective P4 antagonists will prevent LAM fibrosis and hernia formation (FIG. 1A). Although P4 has indispensable physiological and pathological roles in the female uterus and breast[34-36], the only suggested role of P4/PGR reported in males is in the brain, where it may mildly modulate sexual and aggressive behaviors[37-39]. Thus, our studies may reveal a previously unknown role of P4/PGR in males. Since P4 antagonists are unlikely to cause the serious side effects of antiestrogens in males, there is a significant opportunity for discovering novel preventive and therapeutic pharmacological approaches for recurrent inguinal hernias in elderly men through modulation of PGR signaling in LAM tissue.

Figure 2:
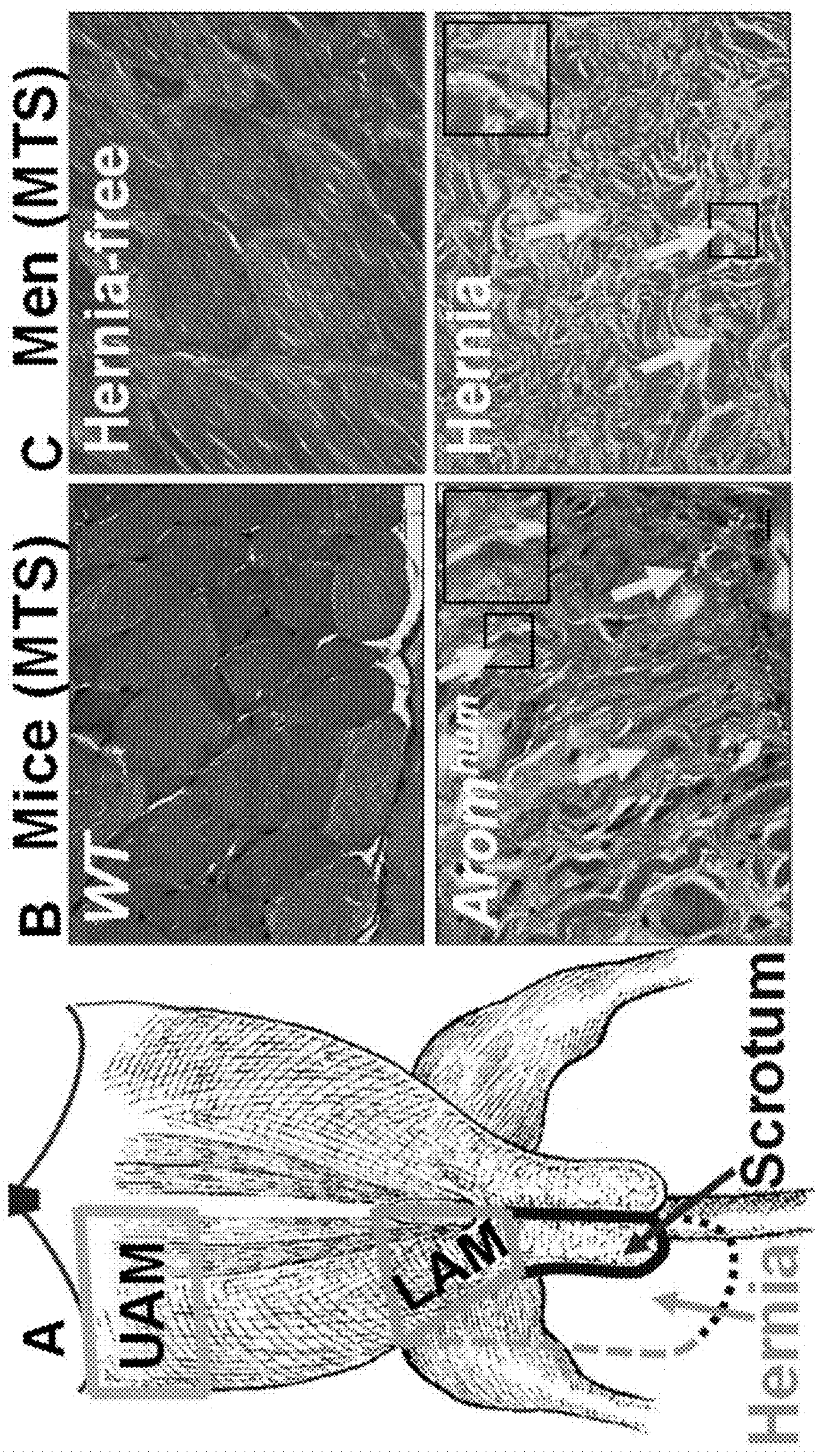
FIG. 2 shows LAM fibrosis and muscle atrophy in Arom$^{hum}$ mice and men with inguinal hernias. (A) Schematic of mouse abdominal muscle anatomy. Solid line in the middle indicates normal LAM tissue in Wild-type (WT) mice. Dashed line indicates fibrotic LAM tissue that comprises the hernia wall contiguous with the scrotum (solid line at the bottom) of Arom$^{hum}$ mice. UAM: Upper abdominal muscle. (B, C) Masson's trichrome staining (MTS) shows LAM fibrosis and atrophied muscle (arrows) in Arom$^{hum}$ mice (n=15) and in elderly men (50-77 years) with inguinal hernias (n=6). Arom$^{hum}$ mice: Mice transgenically expressing human aromatase enzyme.

PGR is a key target gene of E2/ESR1 in the uterus and breast. Thus, there is precedent for E2/ESR1 induction of PGR expression in LAM fibroblasts of male Arom$^{hum}$ mice, although the role of PGR in skeletal muscle was previously unknown. It was reported that E2 plus P4 but not E2 alone induces endometrial stromal cell proliferation and differentiation in the uterus[40]. In addition, P4/PGR also induces fibrosis in pathologic uterine fibroids[41]. PGR is also expressed in fibrotic lungs in humans[42] and P4 treatment enhances bleomycin-induced lung fibrosis in mice[43]. These Examples will explore a novel causal link between PGR, LAM fibrosis, and hernia formation. The primary role of E2/ESR1 in LAM is to induce PGR expression; the fibrotic mechanism is primarily mediated by PGR located in the LAM fibroblasts and activated by P4 present in the circulation. From a translational perspective, administration of a P4 antagonist such as RU486 to men with or at risk for developing a hernia is more feasible compared with antiestrogens or aromatase inhibitors, which would have significant side effects including infertility, sexual dysfunction, and osteoporosis[26-31]. There are no known side effects of anti-progesterones in men. Pgr knockout male mice show normal fertility, whereas Esr1 or aromatase knockout male mice have severely decreased sexual activity and infertility associated with sperm defects[32, 44, 45]. The only possible phenotype found in whole-body or hypothalamic neuron-specific Pgr knockout male mice was mildly reduced sexual and aggressive activity[38, 39, 46]. Thus, the side-effect profile of P4 antagonists in males is highly favorable. In fact, administration of RU486 to men for 2 years to treat unresectable meningiomas was well tolerated[47]. The timing of aromatase/estrogen excess and ESR1/PGR expression in LAM tissue and hernia development in male Arom$^{hum}$ mice and elderly men are expected to be different. Arom$^{hum}$ mice start developing hernia at puberty due to increased LAM E2 converted by aromatase from testosterone that starts to rise at puberty onset. By comparison, it takes decades in men to reach a similar hormonal profile and develop hernias. The underlying steroid-dependent mechanism in Arom$^{hum}$ mice and elderly men, however, is identical. Histologically, skeletal muscle fibrosis and hernias look very similar in both species (FIG. 2).

PGR plays indispensable physiologic roles in preparing the uterus for pregnancy establishment and maintenance and breast development in females[48, 49] and pathologic roles in promoting the growth of mesenchymal or epithelial tumors such as uterine fibroids and breast cancer[41, 50]; its physiologic and pathologic roles in males are largely unknown[35]. These Examples are conceptually innovative, in that it will explore a unique and clearly defined pathologic role of P4/PGR action in males. Mechanistically and technically, unique mouse models will be used combined with several cutting-edge approaches, including fibroblast-selective PGR knockout and multiomic analyses of primary cells using paired single-nucleus (sn)RNA-seq and snATAC-seq, to test a novel hypothesis that LAM PGR, highly expressed in fibroblasts, is essential for LAM fibrosis, muscle atrophy, and hernia formation in Arom$^{hum}$ mice. Additionally, we will translate our findings from animal work to humans.

Figure 6:
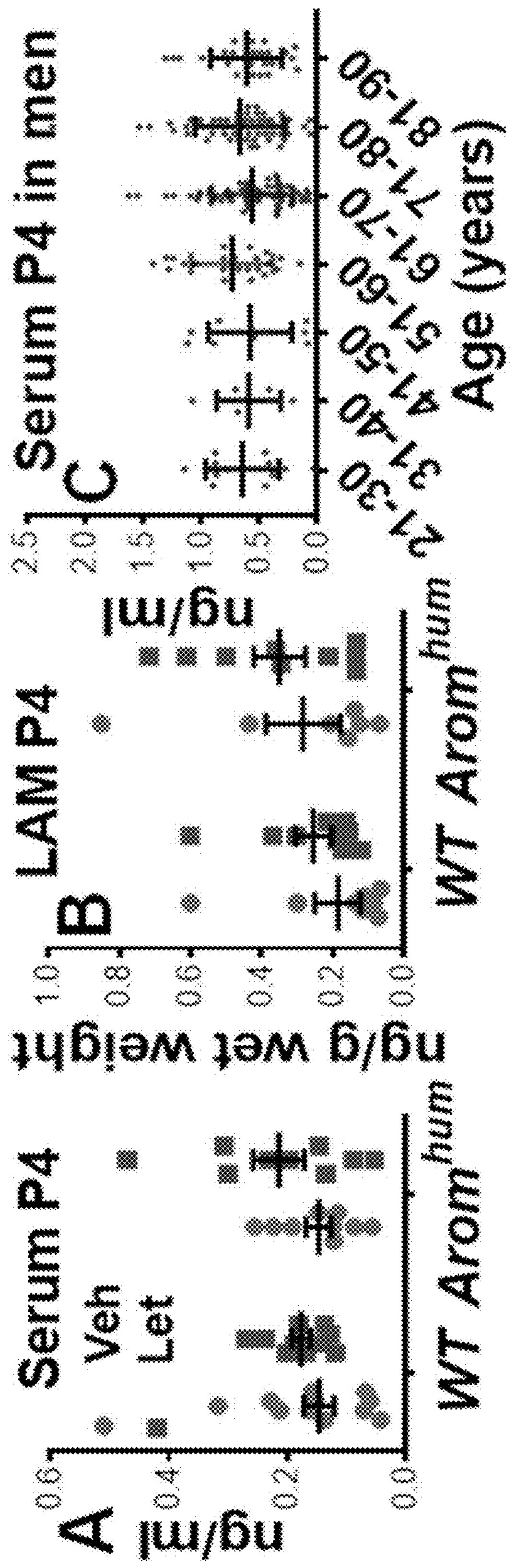
FIG. 6 shows the (A) Serum, (B) LAM tissue P4 in WT and Arom$^{hum}$ mice measured by LC-MS$^2$ after letrozole (Let) treatment (n=10/group), and the (C) Serum P4 levels measured by ELISA in men with inguinal hernia (21-90 years of age; n=211). Veh: vehicle.

Following work with aromatase inhibitors, we recently demonstrated that fulvestrant, an ESR1-selective E2 antagonist, completely reversed muscle fibrosis in existing hernias and restored normal anatomy in Arom$^{hum}$ male mice (FIG. 3)[19, 22]. We also identified PGR as the key downstream effector of E2/ESR1 in LAM fibroblasts in Arom$^{hum}$ mice[22]. This exciting discovery raised the possibility of circumventing the side effects of anti-E2/ESR1 in male mice or men by using P4 antagonists such as RU486 to treat LAM fibrosis and hernia. Both LAM tissue and circulating blood contain readily detectable P4 levels in male mice and men (FIG. 6). Our preliminary data strongly and consistently support our proposed hypothesis (see below).

In summary, Arom$^{hum}$ mice represent a unique and physiologically relevant model to test the innovative hypothesis that high PGR induced by E2/ESR1 causes LAM fibrosis, leading to muscle atrophy and hernia formation. This model is amenable to drug development because treatment with P4/PGR antagonists prevented hernia development. Anti-P4/PGR approaches will likely have a greater translational potential than anti-E2/ESR1 strategies due to their low side effect profile. The hypothesis linking PGR to inguinal hernia development has not been studied in an animal model of inguinal hernia or men, making the proposed work highly innovative.

Increased P4/PGR signaling is necessary and sufficient for LAM tissue fibrosis, muscle atrophy, and hernia formation. Disordered fibroblast proliferation and increased ECM formation in the stromal component of muscle cause weakening of LAM tissue and herniation of abdominal contents into the scrotum.

In Example 1 below, we will determine the roles of high PGR expression in LAM fibrosis and inguinal hernia formation using various PGR-selective P4 antagonists to block LAM fibroblast proliferation, excessive ECM production, myocyte atrophy, and inguinal hernia formation in Arom$^{hum}$ mice. We will also perform multiomic paired snATAC-seq and snRNA-seq on LAM tissue and PGR-ChIP-seq on LAM fibroblasts from Arom$^{hum}$ in the presence of P4 and/or PGR antagonists to define genome-wide PGR target genes. PGR target gene signatures will be assessed by integrative bioinformatics analysis, real-time quantitative PCR (qPCR), RNAScope, immunohistochemistry (IHC), and immunoblotting. In Example 2, we will define the underlying molecular mechanisms of hernia formation via genetic disruption of PGR selectively in fibroblasts in mice and associate the mechanistic data from mouse experiments with human disease. The majority of the experiments will employ whole tissues or isolated primary fibroblasts from LAM or upper abdominal muscle (UAM) tissues. Sampling sites for UAM, healthy LAM, or fibrotic LAM tissue that comprises the hernia wall are shown in FIG. 2. To determine the role of P4/PGR in hernia formation, we will use several strategies, including extended-release pellets for E2, P4, PGR antagonist RU486 (mifepristone), ulipristal acetate (UPA), and ZK299 (onapristone). We will confirm our mechanistic findings in fibrotic and healthy LAM tissue from men with or without hernia. Serum and LAM tissue P4 and E2 will be measured by liquid chromatography-tandem mass spectrometry (LS-MS$^2$)[19, 32, 51].

Herein, we present compelling evidence generated using the Arom$^{hum}$ mouse model, which is physiologically relevant to human disease in terms of the E2/P4 profile. scRNA-seq and microarray analyses of LAM tissues[19, 22], data mining of publicly available database Online Mendelian Inheritance in Man[52], and ESR1 ChIP-seq and RNA-seq analysis of LAM fibroblasts treated with E2 or E2/ESR1 antagonist fulvestrant (ICI182,780, unpublished data) revealed that TGFβ and Wnt pathways and the nuclear receptor PGR and kisspeptin may be the major E2/ESR1 downstream pathways or mediators involved in hernia formation. Arom$^{hum}$ mice have lower serum testosterone levels compared with WT mice[19], which is consistent with low testosterone in elderly men. We treated Arom$^{hum}$ mice with a neutralized TGFβ antibody, a Wnt inhibitor LGK974, and DHT (the most potent androgen) for 12 weeks starting from 3 weeks of age. None prevented hernia formation. Treatment with kisspeptin agonist and antagonist did not alter LAM fibroblast proliferation and collagen production. Thus, our findings regarding the role of P4/PGR signaling in hernias were unbiased. The double-blind studies that RU486/UPA prevented hernia in all treated Arom$^{hum}$ mice reproducibly and observed independently by two lab members added further rigor. Our study design is robust, utilizing Arom$^{hum}$ mice with endpoints examined after treatment with placebo or anti-P4/PGR, and compared to those of WT littermates using 2 different tissue sites: UAM and LAM (normal or weakened/herniated). Inguinal hernia affects predominantly men vs. women (10:1 ratio). Inguinal hernias are unique to male mice and aged men. No female Arom$^{hum}$ mice developed hernias. Here, we will focus on the effects of P4/PGR action on skeletal muscle integrity and hernia formation in males, and our work will be carried out in male mice or tissues primarily from men over 50 years of age. We will use mouse or human tissues or primary cells to closely recapitulate in vivo pathology.

Statistical Methods. Statistical analyses will be performed with the help of the Biostatistics Core Facility of Northwestern University. The normality of biological data distribution will be checked, and log-transformations will be made for non-normal data. Variables will be compared across different groups of mice for each aim using Kaplan-Meier curves, t-test, or ANOVA followed by Tukey's (parametric) or Chi-square test of independence (non-parametric)[53]. Sample size calculations are based on the published results of similar studies from our laboratory[19, 22, 54-58]. For most experiments, 15 mice in each group at each time point will be adequate to detect at least a 30% difference at 80% power in physiological and morphometric parameters, assuming a 30% coefficient of variation. Bioinformatics analysis for multiomic paired snATAC-seq and snRNA-seq, PGR ChIP-seq, and their integration is discussed in detail under Hypothesis 1b. All surgical procedures, substance administration, sample collections, and histological analyses will be performed in a double-blind fashion. If a larger sample size appears to be necessary, the experiments will be repeated under the same conditions. Statistical significance will be assigned if two-tailed $p<0.05$.

Example 1. Determine the Mechanisms by Which PGR Mediates LAM Tissue Fibrosis, Myocyte Atrophy, and Hernia Formation

Hypothesis 1a

PGR induced by aromatase expression, E2 production, and ESR1 activation is essential for disordered proliferation of PGR-expressing fibroblasts and increased production of ECM, which progressively replace the myofiber component of muscle tissue, leading to LAM tissue myocyte atrophy, weakness, and hernia.

Rationale

Figure 4:
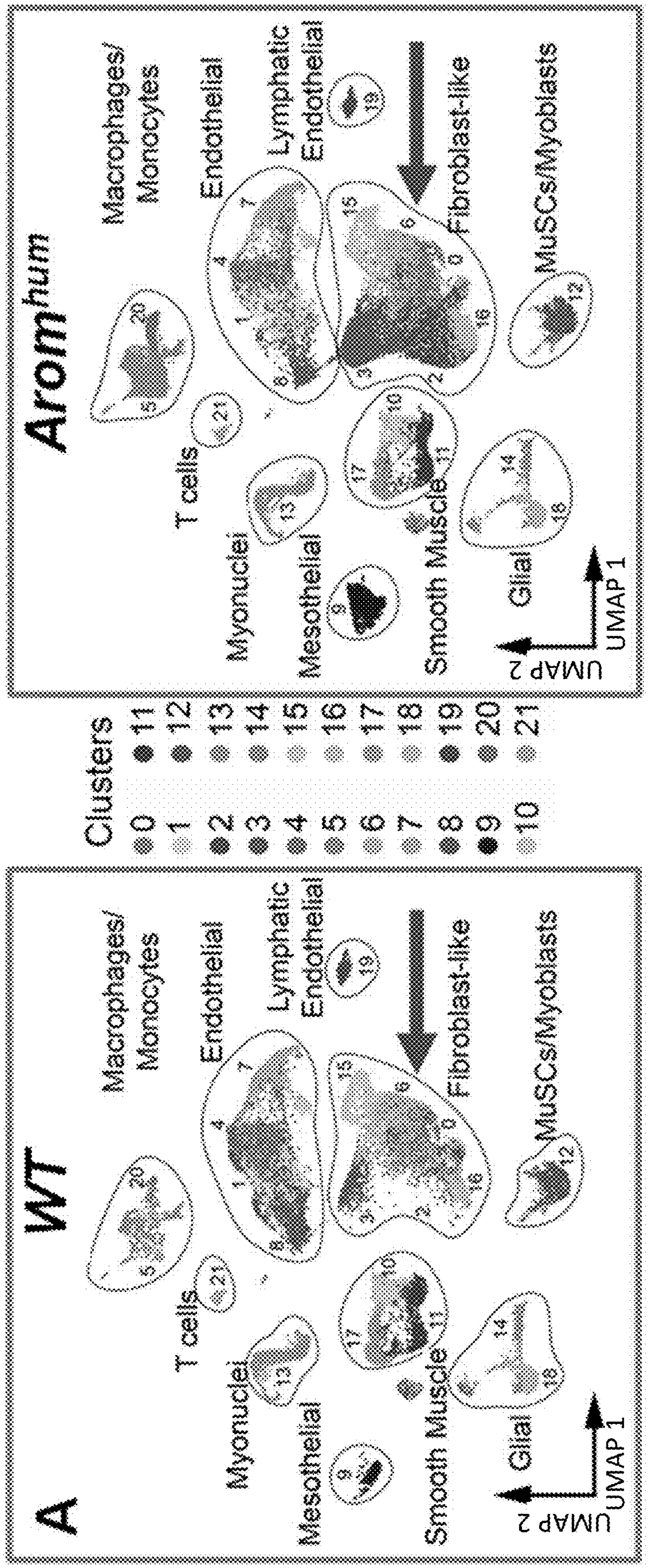
FIG. 4 shows that PGR is highly expressed in LAM fibroblasts of Arom$^{hum}$ mice. (A) Single-cell (sc)RNA-seq cell clusters through gene marker expression analysis in LAM tissues of 9- to 10-week-old male WT and Arom$^{hum}$ mice. UMAP plot of WT cells alone and Arom$^{hum}$ cells alone. When both groups were analyzed together, 22 cell clusters were found, and cells were grouped into 10 cell categories based on canonical marker expression (n=3). Feature plots representing (B) Pdgfra, (C) Esr1, and (D) Pgr expression in fibroblast-like cells from WT mice or Arom$^{hum}$ mice on individual UMAP plots. Color intensity corresponds to relative expression. UMAP, uniform manifold approximation and projection. Immunohistochemistry (IHC): nuclear ESR1 (E) and PGR (F and inset) in LAM tissue of WT and Arom$^{hum}$ mice. Arrows and insert in panel F, immunoreactive PGR. Bar, 20 μm.
Figure 4:
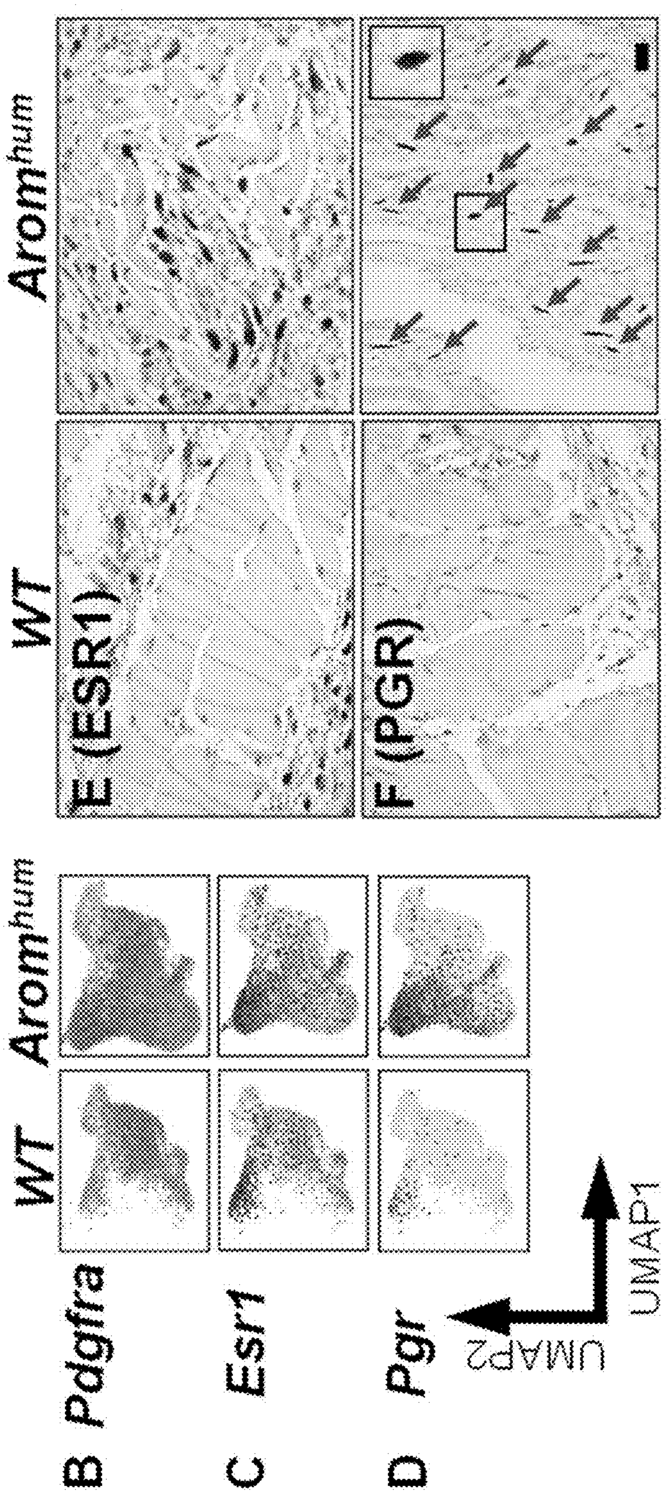
Figure 5:
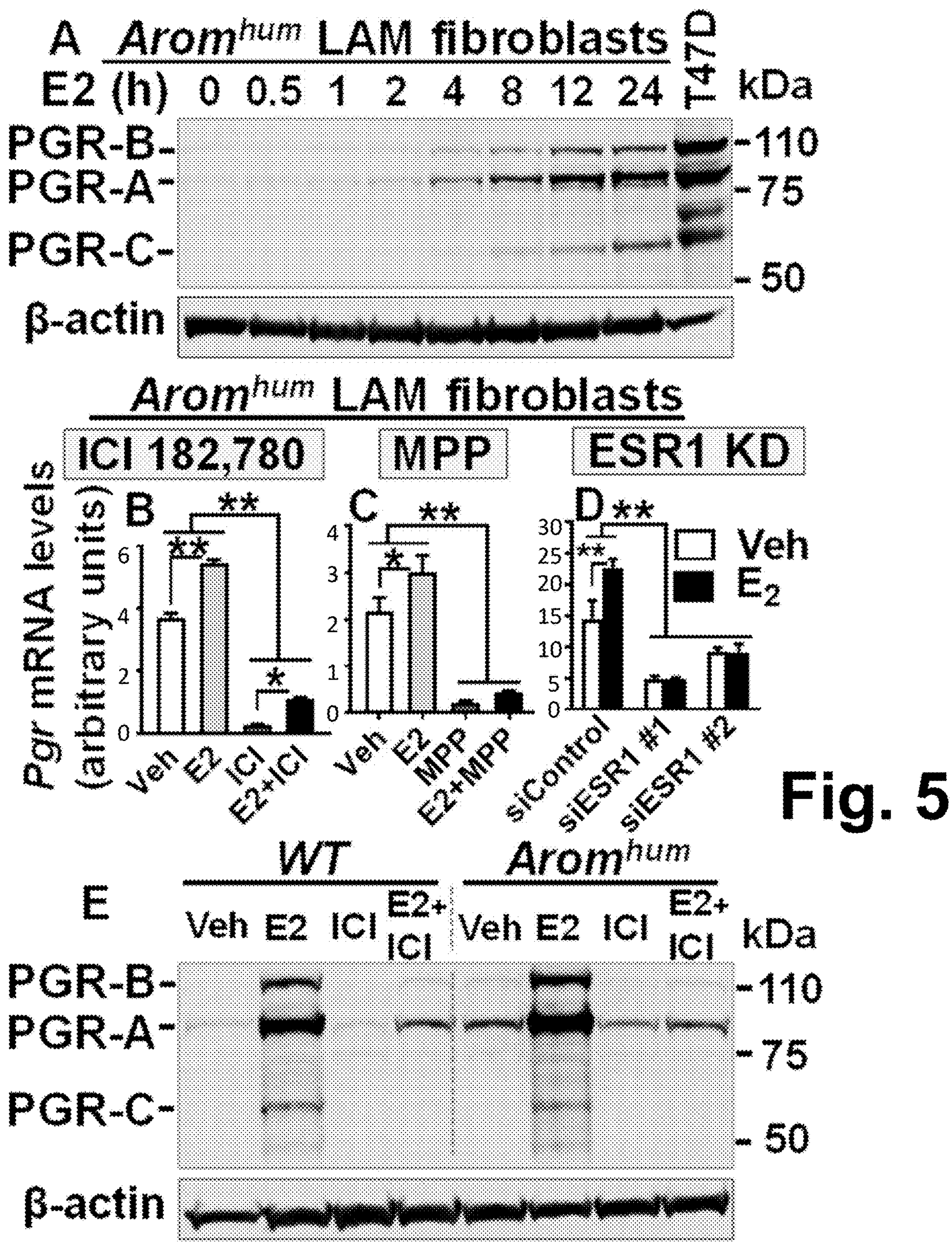
FIG. 5 shows that PGR expression is induced by E2/ESR1 in LAM fibroblasts of Arom$^{hum}$ mice. (A) Time course of E2 (10 nM) effect on PGR protein expression in LAM fibroblasts of Arom$^{hum}$ mice. The breast cancer cell line T47D served as a positive control. mRNA levels of the estrogen-responsive gene Pgr in LAM fibroblasts from Arom$^{hum}$ mice after treatment with 100 nM ICI 182,780 (ICI, B) or 10 μM MPP (C) or siRNA-mediated knockdown of ESR1 (D) in the presence or absence of E2 (10 nM). GAPDH mRNA levels served as loading controls. *$p<0.05$, **$p<0.01$. (E) PGR protein levels in LAM primary fibroblasts from WT and Arom$^{hum}$ mice after treatment with ICI with or without E2 for 48 h. Cells were pretreated with ICI or MPP for 2 h before adding E2. Data are representative of 3 independent experiments; B-actin serves as a loading control for (A) and (E). Vch: vehicle. ICI 182,780: Alternative name is fulvestrant. MPP: A selective ESR1 antagonist.
Figure 7A:
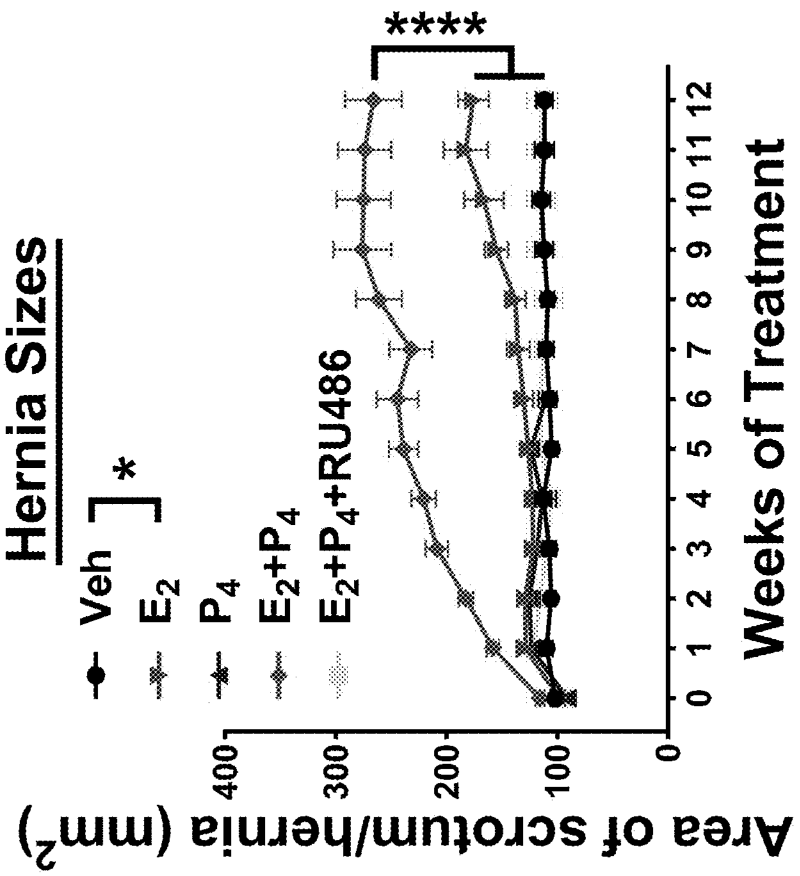
FIGS. 7A-7E shows that P4 induces and RU486 or UPA prevents inguinal hernia formation.
Figure 7B:
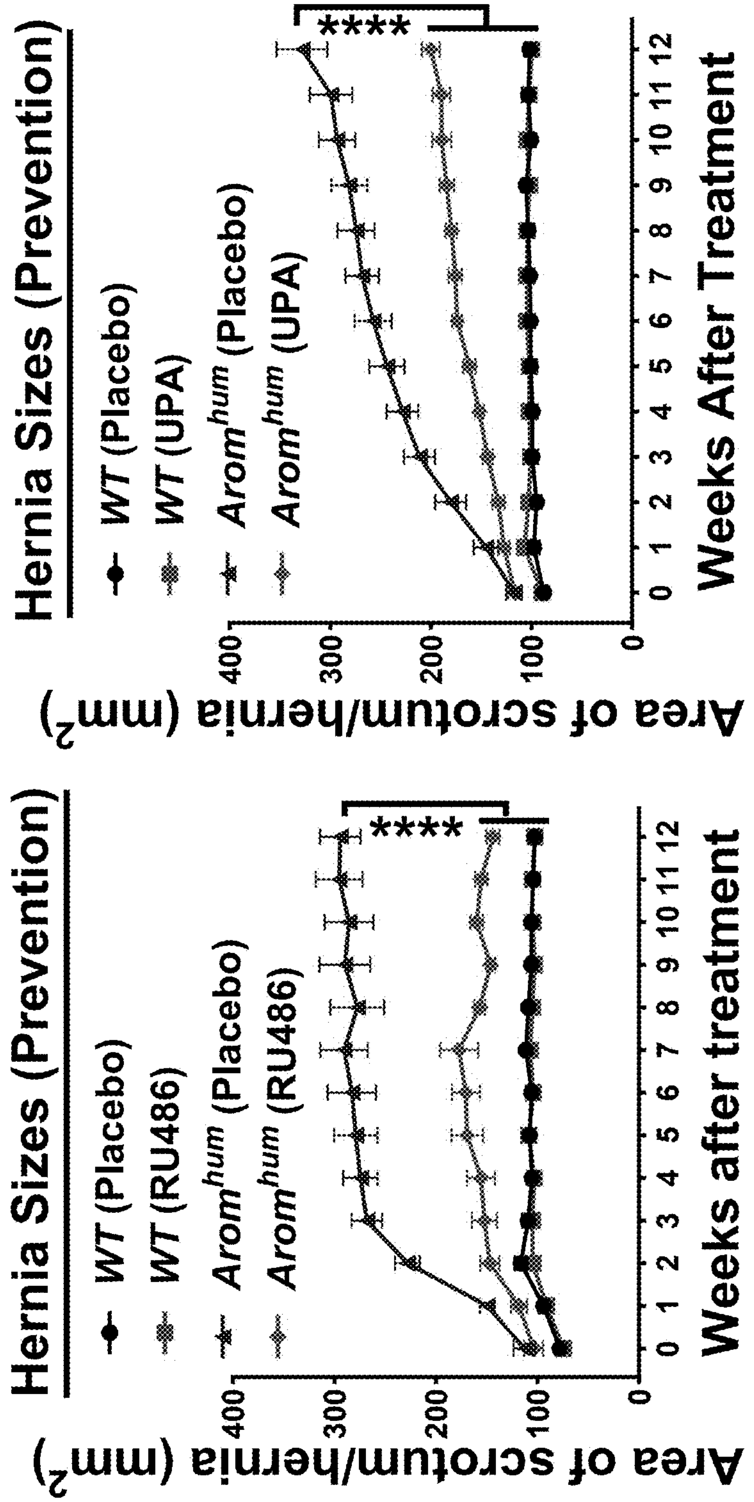
Figures 7C, 7D, 7E:
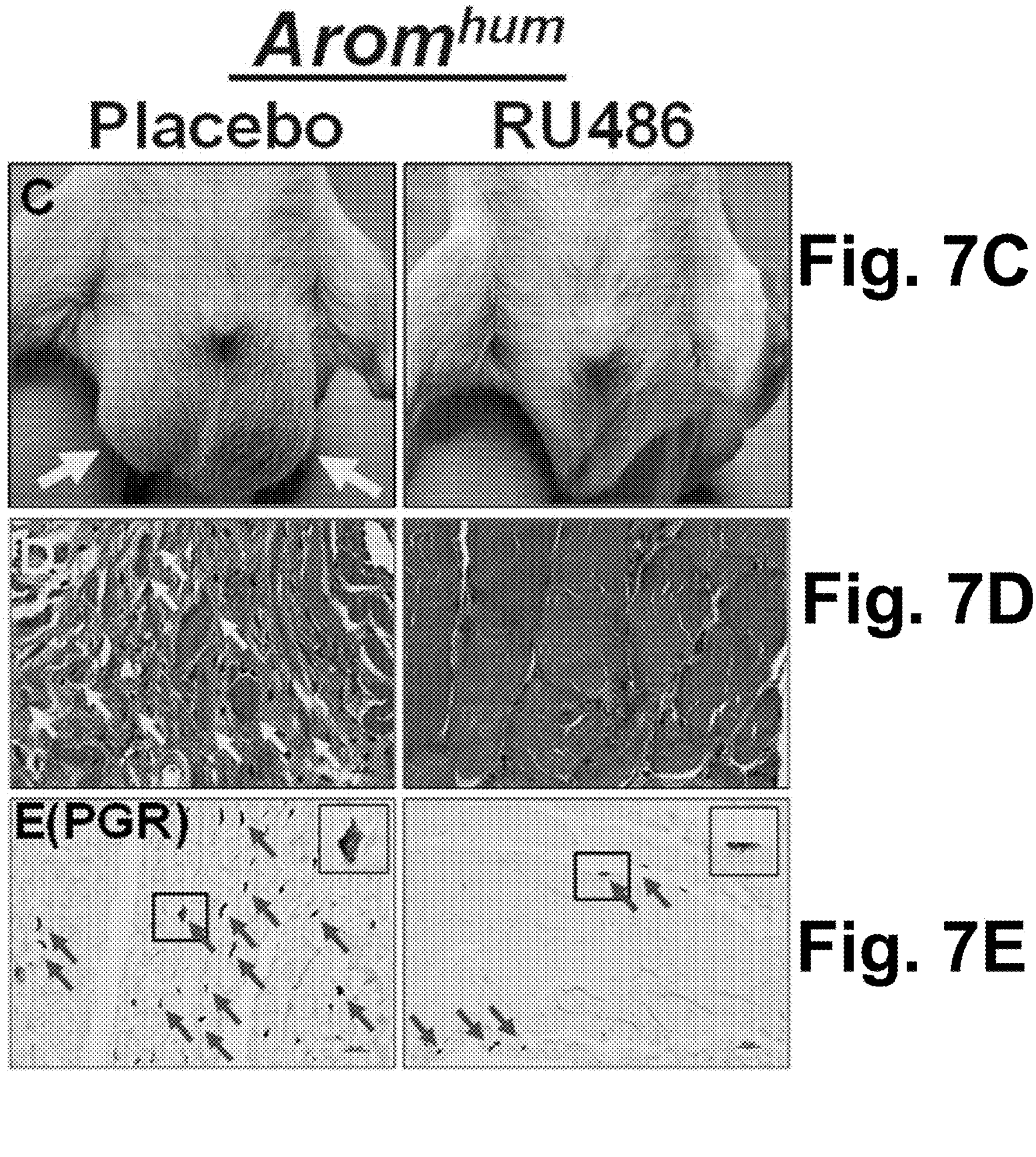
Figure 8:
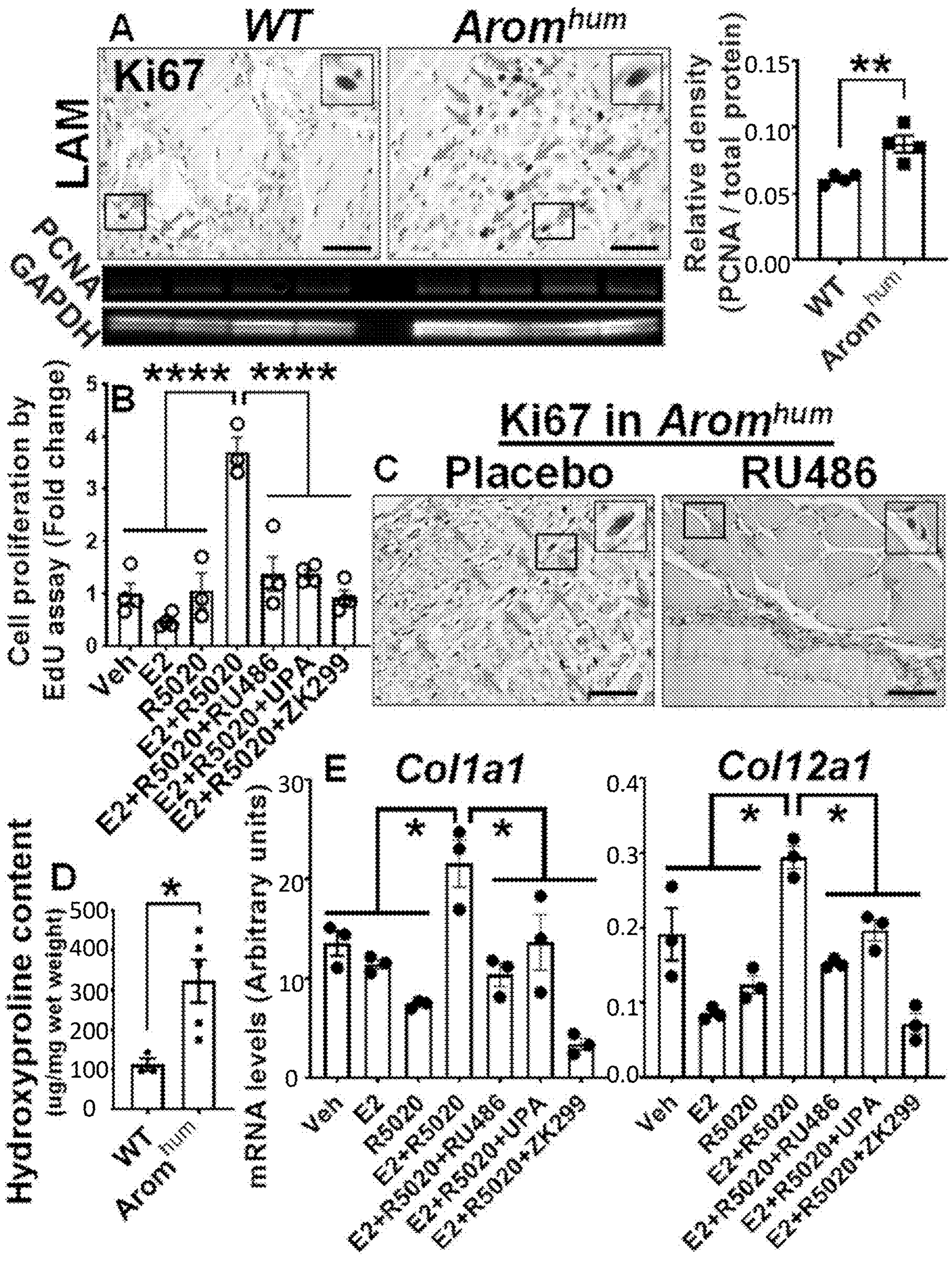
FIG. 8 shows that fibroblast proliferation and collagen formation are stimulated by P4 agonist R5020 and inhibited by P4 antagonists in LAM fibroblasts of Arom$^{hum}$ mice. (A) Ki67 IHC staining in LAM fibroblasts comparing proliferation in WT and Arom$^{hum}$ mice (n=5). Cell proliferation marker PCNA protein levels were measured by immunoblotting and quantified by densitometry in LAM tissues of WT and Arom$^{hum}$ mice (n=4). GAPDH served as a loading control. (B) Proliferation of LAM fibroblasts from Arom$^{hum}$ mice measured by the Click-iT EdU proliferation assay was increased by E2 (10 nM)+R5020 (100 nM) and inhibited by 1 μM RU486, UPA or ZK299. (C) Ki67 IHC staining (arrows) in LAM fibroblasts to assess cell proliferation in Arom$^{hum}$ mice treated with placebo or RU486 (n=6). (D) Total collagen content in LAM tissue of WT and Arom$^{hum}$ mice measured by hydroxyproline assay (n=5). (E) mRNA levels of Col1a1 and Col12a1 in primary LAM fibroblasts of Arom$^{hum}$ mice after pretreatment with 1 μM RU486, UPA or ZK299, followed by treatment with E2 and/or R5020. Data are representative of 3 independent experiments. Data was normalized to GAPDH mRNA levels. $*p<0.05$, $p<0.01$, $**p<0.0001$. Bar, 50 μm. RU486, UPA, and ZK299 are progesterone antagonists or antiprogestin.
Figure 9:
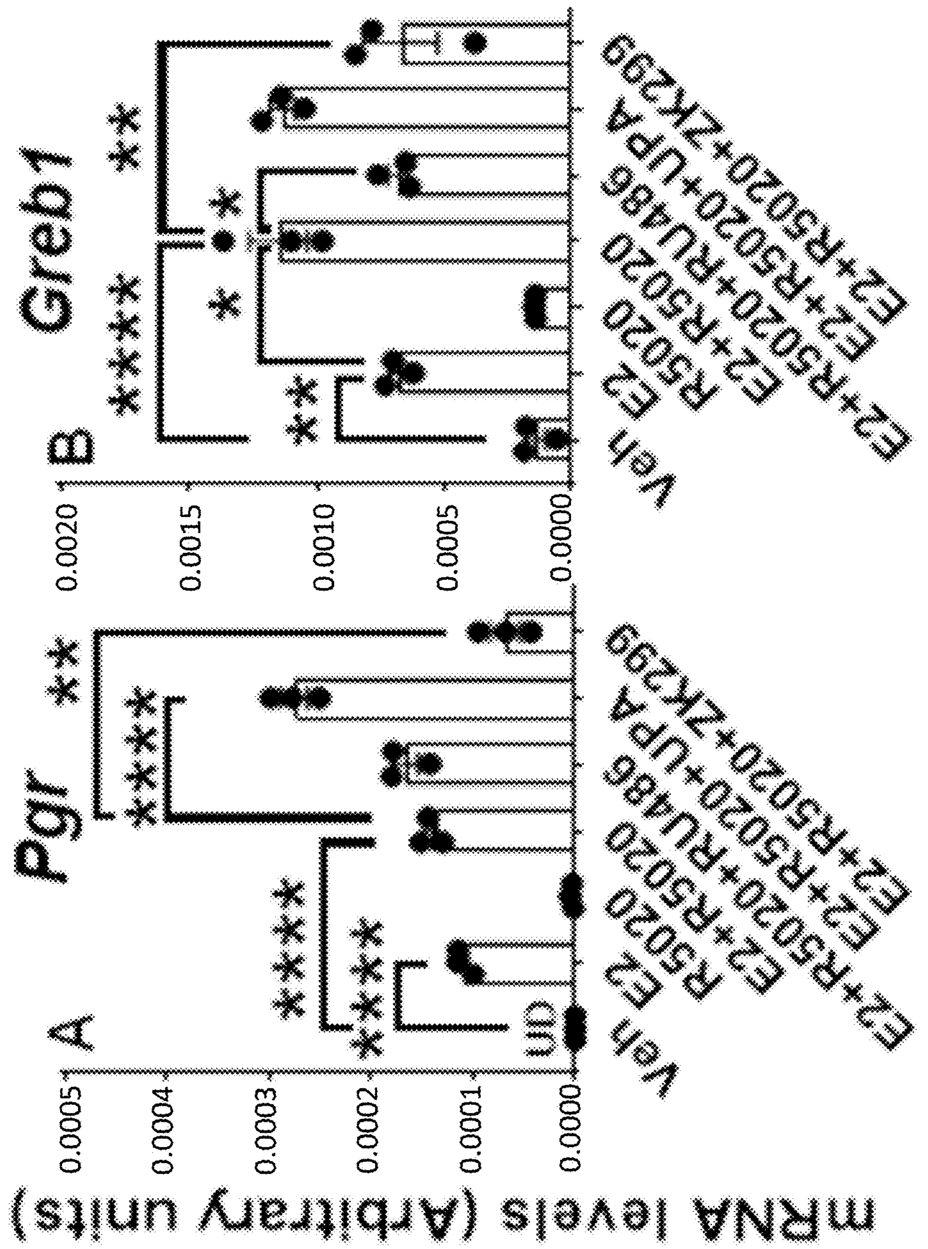
FIG. 9 shows the mRNA levels of Pgr (A), P4/PGR-responsive genes [Greb1 (B) and Cyp7b1 (C)], and fibrotic genes [Col14a1 (D) and Adamtsl1 (E)] in LAM primary fibroblasts from Arom$^{hum}$ mice after treatment with E2 (10 nM) and/or R5020 (100 nM) in the presence or absence of 1 μM RU486, UPA, or ZK299. Cells were pretreated with RU486, UPA, and ZK299 for 2 h before adding E2+R5020. Data was normalized to GAPDH mRNA levels. Veh: Vehicle. UD: Undetermined. $*p<0.05$, $p<0.01$, $*p<0.001$, $****p<0.0001$.
Figure 9:
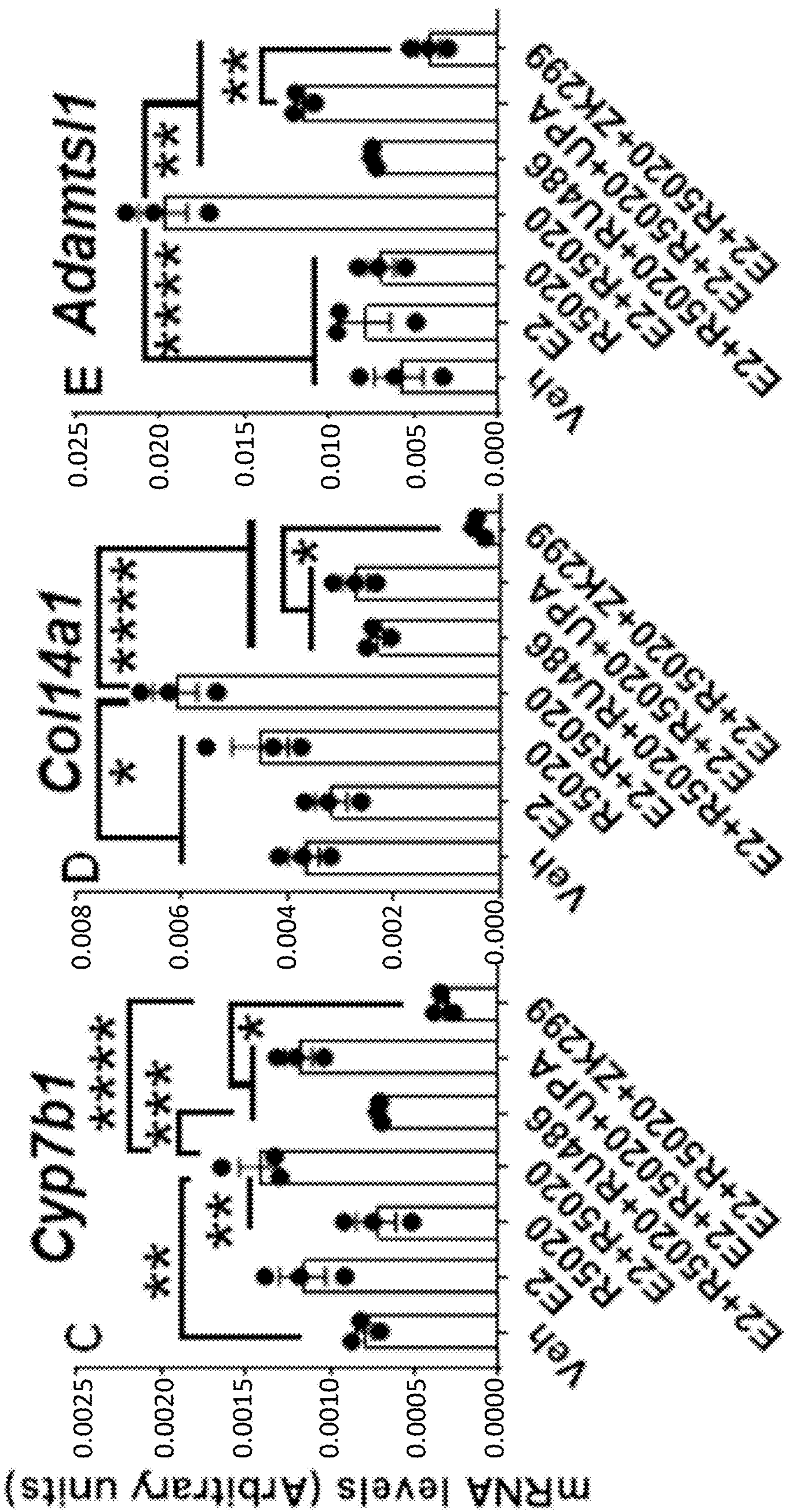
Figure 12:
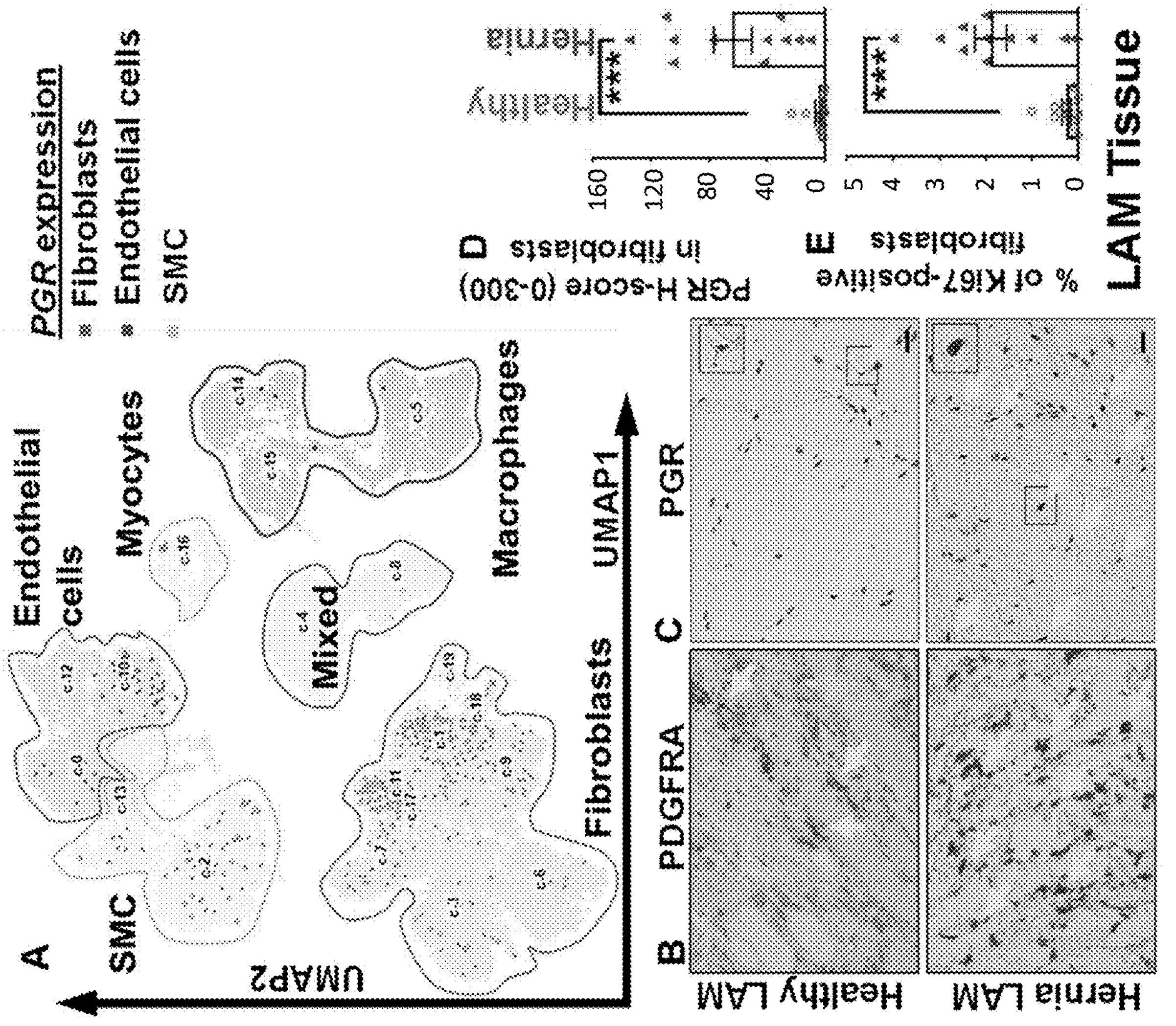
FIG. 12 shows (A) Feature plots representing PGR expression in cells from human skeletal muscle tissue on individual UMAP plots. Color intensity corresponds to relative expression. SMC: Smooth muscle cells. Immunoreactive PDGFRA (B) and PGR (C) in LAM tissue from hernia and adjacent healthy area. Arrows show positive staining. (D) PGR H-Score and (E) % of Ki67+nuclei in fibroblasts in LAM tissue from hernia and adjacent healthy area (n=11). $***p<0.001$. Bar, 20 μm.

We previously demonstrated that locally produced E2 in LAM tissue via human aromatase expression, but not moderately increased circulating E2, caused disordered proliferation of ESR1-expressing fibroblasts, excessive ECM formation, and myocyte atrophy, thus weakening LAM tissue leading to herniation of the abdominal contents (FIG. 3)[19, 22]. This resonates with LAM atrophy and hernia in men because local aromatase expression in peripheral tissues such as skeletal muscle in men and women increases with aging by 4-fold[59-64]. Locally produced E2 exerts an intense intracrine estrogenic effect via ESR1 to cause maximum induction of E2/ESR1 target genes including PGR; PGR IHC staining is absent in WT LAM tissue but highly expressed in the nuclei of LAM fibroblasts in Arom$^{hum}$ mice and hernia fibroblasts of men (FIGS. 4, 5, and 12). P4 was detectable in both serum and LAM tissue in Arom$^{hum}$ mice, comparable to the circulating P4 levels found in men with hernias (FIG. 6). However, the physiologic or pathologic roles of P4/PGR in skeletal muscle tissue in men are unknown. Short-term (6 weeks) P4+E2 treatment induced much larger hernias at an earlier time point than E2-alone treatment in WT mice (FIG. 7A). Treatment of Arom$^{hum}$ mice with RU486/UPA starting at 3 weeks of age prevented LAM tissue fibrosis or inguinal hernia in all mice (FIGS. 7B-E). E2+R5020 (a PGR/P4 agonist), but not E2 or R5020 alone stimulated LAM fibroblast proliferation. E2+R5020 also increased mRNA levels of PGR-target genes (Greb1, Cyp7b1) and fibrotic genes (Adamtsl1, Col1a1, Col12a1, Col14a1), and RU486 and other P4/PGR antagonists, UPA and ZK299, blocked the induction of these genes (FIG. 8, panel F and FIG. 9). Here, we propose mechanistic in vivo and in vitro experiments to assess the role of P4/PGR in skeletal muscle fibrosis, myocyte atrophy and hernia formation and provide critical evidence supporting a causal link between P4/PGR action and the development of inguinal hernias in males.

Background, Data, and Discussion

We previously showed that excessive local E2 production in the LAM tissues triggers extensive LAM fibrosis, leading to hernia formation in Arom$^{hum}$ mice; the aromatase inhibitor letrozole entirely prevents this phenotype[19]. Stunningly, treatment with letrozole or the E2/ESR1 antagonist fulvestrant reversed existing hernias and restored normal anatomy in Arom$^{hum}$ mice. E2 acts via ESR1, highly expressed in LAM fibroblasts, to activate pathways for proliferation and fibrosis that replaces atrophied myocytes, resulting in hernia formation. scRNA-seq analysis of LAM tissue identified two novel and unique hernia-associated fibroblast (HAF) clusters in Arom$^{hum}$ mice, one enriched for ESR1 and another enriched for ECM-altering enzyme (MMP3), and the profibrotic gene products for both[21]. Histologically, we recapitulated these findings in humans and found that healthy-appearing muscle fibers and stromal tissue on LAM tissue biopsies from 6 hernia-free men (50-68 years) and fibrotic tissue with islands of atrophic myocytes (yellow arrows) in hernia biopsies from 6 men with hernia (60-77 years, FIG. 2, panels B, C). ESR1-positive staining and the percentage of cells with proliferation marker Ki67 were significantly higher in the LAM stroma from men with hernia compared with hernia-free men[19].

Figure 3:
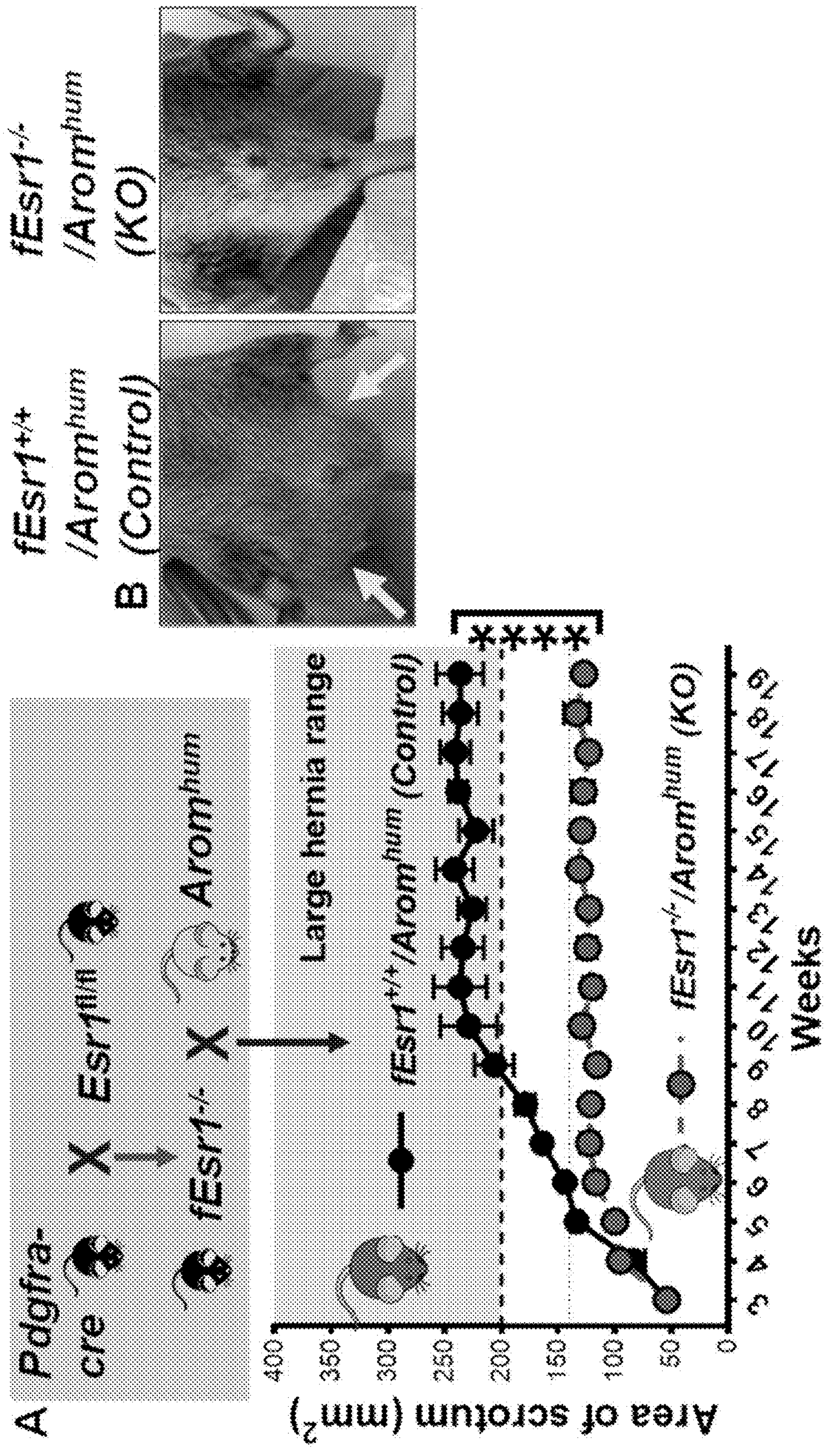
FIG. 3 shows that fibroblast-specific ESR1 knockout prevents and fulvestrant treatment reverses inguinal hernias in Arom$^{hum}$ mice. Hernia area (A) and morphology (B) in fibroblast-specific ESR1 knockout (KO) in Arom$^{hum}$ mice showed prevention of hernia formation (n=4-5). (C) Hernia area measurements and (D) gross appearance (upper) and Masson's trichrome staining (lower) showed that E2/ESR1 antagonist fulvestrant reversed large hernias and restored normal anatomy and reversed LAM tissue fibrosis and muscle atrophy in Arom$^{hum}$ mice during a 12-week treatment (n=10-11). ****$p<0.0001$. Arrows in panels B and D point to hernias.
Figure 3:
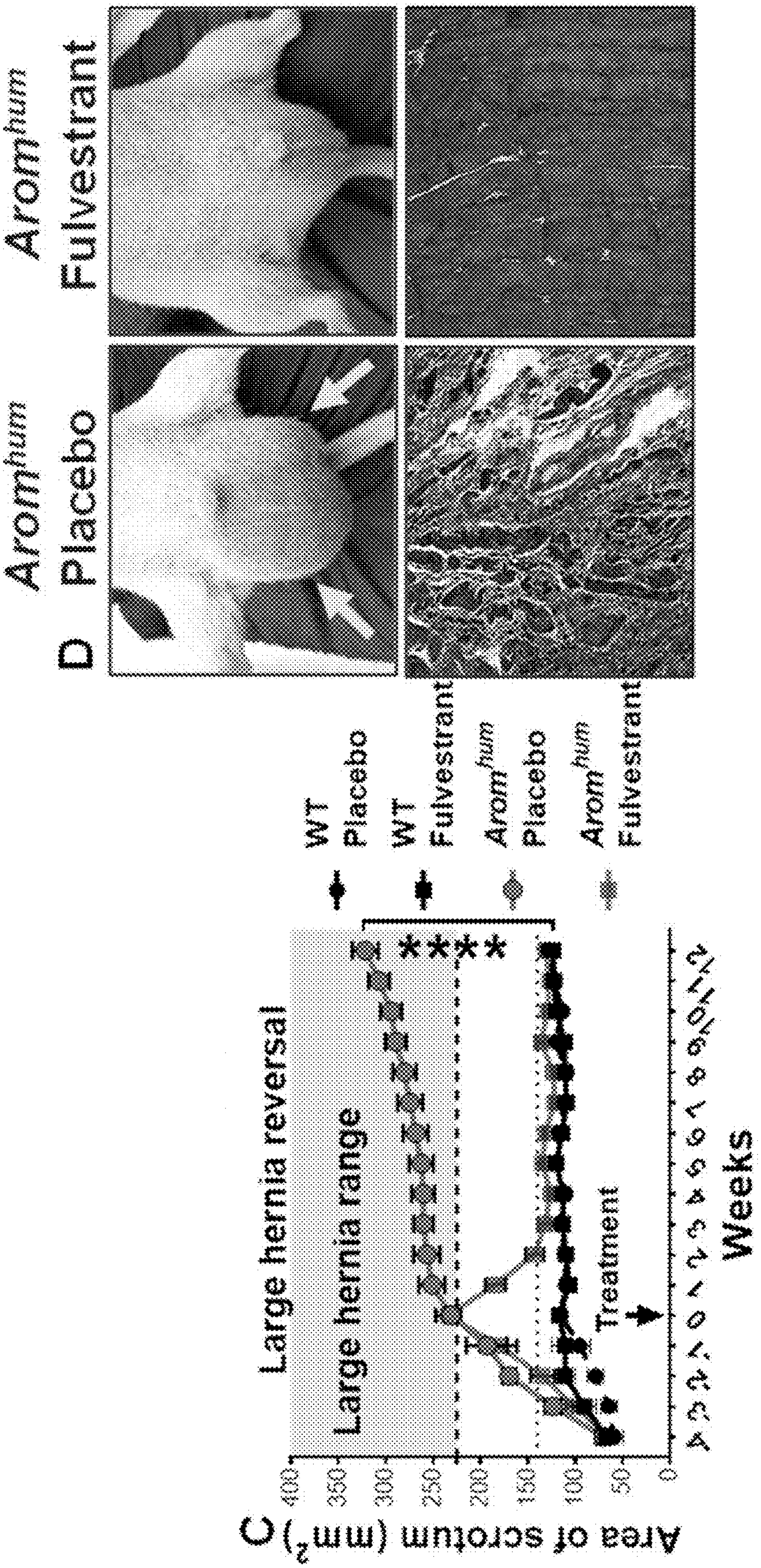

Further, fibroblast-specific ablation of ESR1 using platelet-derived growth factor receptor A (Pdgfra)-cre mice completely blocked hernia formation in all Arom$^{hum}$ mice during a 19-week follow-up (FIG. 3, panel A). As expected, littermate controls developed hernias starting from the age of 5 weeks, which progressively increased in size as they aged. The scrotal area in WT mice is under ~125 mm$^2$. We classified hernias as small, medium, or large based on the bulging area through muscle tissue of 125-175 mm$^2$, 175-225 mm$^2$, or ≥225 mm$^2$, respectively. Administration of the E2/ER antagonist fulvestrant (3.75 mg/pellet for 12-week subcutaneous release)[65] to Arom$^{hum}$ mice with large hernias successfully reversed them to normal size, rescued LAM fibrosis, reversed muscle atrophy, and restored normal anatomy (FIG. 3, panels C-D). Since long-term anti-E2/ESR1 treatments cause significant side effects (e.g., sexual dysfunction or osteoporosis), we mechanistically explored the specific and major downstream effectors of E2/ESR1 signaling leading to muscle fibrosis. We found that Pgr is strikingly upregulated and colocalized with Esr1 in the Esr1-enriched fibroblasts in LAM tissue from Arom$^{hum}$ mice (FIG. 4, panels B-D). The key observations that support the role of P4/PGR signaling are summarized below.

PGR is highly expressed in LAM fibroblasts of Arom$^{hum}$ mice. We performed scRNA-seq analysis on LAM tissue from male Arom$^{hum}$ and WT mice and found 22 transcriptionally distinct clusters, in which clusters 0, 2, 3, 6, 15, and 16 were designated as fibroblast-like cells (FIG. 4, panel A, arrows) due to their abundant expression of the fibro-adipogenic progenitor cell marker Pdgfra and genes encoding ECM-associated proteins such as Col1a1 and Mfap4 (FIG. 4B)[22]. Clusters 2 and 3 were designated as novel hernia-associated fibroblast (HAF) clusters for their enrichment in Arom$^{hum}$ LAM tissue. Cluster 3 fibroblasts were enriched for the Esr1 gene and maximally expressed estrogen target genes and seemed to serve as the progenitors of cluster 2, highly expressing ECM-altering enzymes (e.g., Mmp3) and proinflammatory and profibrotic genes (FIG. 4, panel C)[22]. Pgr mRNA is nearly absent in WT LAM fibroblasts but highly expressed in Esr1-high cluster 3 HAFs (FIG. 4, panel D). IHC staining further confirmed that nuclear immunoreactive PGR and ESR1 localized primarily in fibroblasts dispersed in LAM stroma but not in myocytes. PGR protein was highly expressed in the fibroblasts of LAM tissue of Arom$^{hum}$ mice but absent from WT LAM tissue (FIG. 4, panels E, F). These results suggest that E2/ESR1 pathway is the key driver of PGR expression in LAM fibroblasts of Arom$^{hum}$ mice.

PGR expression is induced by E2/ESR1 in LAM fibroblasts of Arom$^{hum}$ mice. Primary LAM tissue fibroblasts from Arom$^{hum}$ mice treated with 10 nM E2 at different time points (0.5, 1, 2, 4, 8, 12, and 24 h) showed a time-dependent increase in three PGR isoforms (PGR-A, PGR-B, and PGR-C) (FIG. 5, panel A). Breast cancer cell line T47D served as a positive control. Because ESR1 is the primary estrogen receptor in LAM fibroblasts of Arom$^{hum}$ mice[19], we treated Arom$^{hum}$ LAM primary fibroblasts with fulvestrant (ICI 182,780), a general and strong antagonist that blocks ER-dependent E2 action via degradation or inhibition of ER protein in target cells[66, 67], or MPP, an ESR1-selective E2 antagonist[68-70], and found significantly decreased E2-induced expression of Pgr (FIG. 5, panels B, C). Transient depletion of ESR1 using two mouse Esr1 siRNAs in Arom$^{hum}$ LAM fibroblasts also significantly downregulated Pgr expression (FIG. 5, panel D). Immunoblotting further showed that the protein levels of 3 PGR isoforms were induced by E2 and blocked by ICI182,780 treatment in LAM fibroblasts of WT and Arom$^{hum}$ mice (FIG. 5, panel E). These data indicate that E2-dependent PGR expression is mediated by ESR1 in LAM fibroblasts of Arom$^{hum}$ mice.

P4 levels in circulation and LAM tissue of Arom$^{hum}$ mice and in the serum of men with inguinal hernia. P4 levels are relatively low but detectable in postmenopausal women and in men[71, 72]. Similarly, P4 is detectable in serum and LAM tissue of male Arom$^{hum}$ mice measured by LS-MS$^2$ (FIG. 6, panels A, B). LAM tissue E2 levels were strikingly higher in Arom$^{hum}$ mice compared with WT littermates and letrozole treatment completely restored LAM E2 levels to normal (WT) levels[19]. Serum and LAM P4 levels were not altered following letrozole treatment, as expected. As in mice, serum P4 was maintained at detectable levels in men with inguinal hernia (FIG. 6, panel C). These observations suggest that P4 is constantly present in the circulation and LAM tissue and can bind and activate PGR when its expression is induced by elevated estrogen.

High LAM PGR expression is associated with LAM fibrosis, myocyte atrophy, and inguinal hernia development; P4 antagonists RU486/UPA prevent hernia formation in Arom$^{hum}$ mice. We confirmed that the development of hernia was positively associated with P4/PGR signaling, as our study showed that treatment of WT male mice with P4+E2 starting at the age of 9 weeks significantly induced hernia formation in all mice in a week and induced large hernias (>225 mm2) within just 2-4 weeks, whereas E2-only treated mice induced the development of small hernias (125-175 mm2) and P4-only treatment did not induce any hernia formation after 10-12 weeks (FIG. 7A). Previous studies reported that treatment of WT male mice of similar age for longer periods with systemic estrogen eventually caused hernias in one third to half of the mice[23-25]. The large hernias in P4+E2 treated mice were completely prevented with concurrent RU486 treatment. In a follow-up experiment, RU486 treatment starting at 3 weeks of age strikingly reduced hernia size or entirely prevented hernia development in all Arom$^{hum}$ mice (n=10, FIG. 7B, 7C). The scrotal area in RU486-treated Arom$^{hum}$ mice was slightly larger than that of WT littermates but was maintained within the upper limit of normal with no evidence of herniation, suggesting that E2/ESR1 signaling initiates minimal muscular changes but P4/PGR is essential for progression to inguinal hernias. All placebo-treated Arom$^{hum}$ mice developed hernias starting from 5 weeks of age. None of the WT littermates developed hernias. Our study also showed that another P4 antagonist, UPA, also prevented hernia formation (FIG. 7B). The mouse scrotum is connected to the peritoneal cavity with a narrow funicular (or inguinal) canal, with walls composed of LAM tissue. Structurally normal LAM tissue is essential to maintain the tone of this canal and prevent herniation of the bowel. LAM in placebo-treated Arom$^{hum}$ mice exhibited increased numbers of disordered stromal fibroblasts, ECM formation (fibrosis), and atrophic myocytes with reduced size (arrow; FIG. 7D), indicating accelerated muscle atrophy and insufficient regeneration activity with a net result of muscle loss. Administration of the P4 antagonist RU486 prevented LAM tissue fibrosis and atrophy in all treated Arom$^{hum}$ mice. Diminished fibrosis was accompanied by severely reduced numbers of PGR-positive fibroblasts in LAM tissues of RU486-treated Arom$^{hum}$ mice (FIG. 7E). These observations suggest that PGR induction is the key mediator of pathologic E2/ESR1 action to weaken inguinal LAM via muscle fibrosis and atrophy, which significantly enlarges the caliber of the inguinal passageway and gives way to herniation of the abdominal contents into the scrotum.

P4 induces fibroblast proliferation and ECM formation in LAM tissue via PGR. In vivo, prominently increased Ki67 staining indicating cell proliferation was consistently observed in LAM fibroblasts of Arom$^{hum}$ mice compared with WT mice (FIG. 8, panel A). Cell proliferation marker PCNA protein levels in LAM tissues were higher in Arom$^{hum}$ mice than in WT mice (FIG. 8, panel A). Primary LAM fibroblasts from Arom$^{hum}$ mice treated with E2+R5020 (P4 agonist), but not by E2 or R5020 alone, for 24 h showed strikingly increased EdU incorporation indicating proliferative activity (FIG. 8, panel B). LAM fibroblast proliferation was blocked in vitro by RU486, UPA or ZK299 or in vivo by RU486 in Arom$^{hum}$ mice (FIG. 8, panels B, C). The total collagen (hydroxyproline) content in LAM tissues was higher in Arom$^{hum}$ mice than in WT mice (FIG. 8, panel D). ECM deposition, indicated by increased expression of type I collagen (Col1a1) and collagen XII (Col12a1), was stimulated by E2+R5020 and blocked by RU486, UPA, or ZK299 (FIG. 8, panel E). scRNA-seq analysis of LAM tissues of WT and Arom$^{hum}$ mice identified several differentially expressed P4/PGR responsive genes (e.g., Greb1, Cyp7b1) and fibrosis-related genes (e.g., Adamtsl1, Col1a1, Col14a1) in ESR1- and PGR-positive HAFs[22]. Treatment of Arom$^{hum}$ LAM primary fibroblasts with RU486, UPA, or ZK299 significantly decreased E2+R5020-induced expression of these P4/PGR-responsive and fibrotic genes (FIG. 9). Thus, we found that P4 prompts PGR-rich fibroblast proliferation and ECM formation in LAM tissue of Arom$^{hum}$ mice, leading to hernia formation.

In summary, PGR, regulated by E2/ESR1, is enriched in ESR1-expressing HAFs of Arom$^{hum}$ mice. PGR is activated by P4 present in LAM tissue. PGR-rich HAF proliferation and ECM formation in LAM tissue lead to replacement of myofibers by proliferating fibroblasts and ECM. The decreased tone of weakened LAM tissue permits formation of inguinal hernias in all Arom$^{hum}$ mice. Conversely, no hernias develop in WT mice, which lack immunoreactive PGR in LAM tissue. We hypothesize that Arom$^{hum}$ mice treated with P4/PGR antagonists will show diminished LAM fibrosis or atrophy and a lower prevalence of inguinal hernia.

Proposed Experiments

Experiment 1a1: Does the addition of P4 to E2 treatment accelerate LAM fibrosis and hernia formation in WT mice? It was shown that treatment of male WT mice with extremely high doses of systemic estrogens starting around or after the onset of puberty caused inguinal hernia in one third to half of these animals[23-25]. We hypothesize that this effect is primarily mediated by the E2 induction of PGR expression in LAM fibroblasts. Male mice have readily detectable P4 levels in the circulation and LAM tissue to activate PGR in LAM fibroblasts (FIG. 6). If this were true, the addition of pharmacologic quantities of P4 (75 mg/pellet for 12-week release)[73] to E2 (0.3 mg/pellet for 12-week release)[23-25] in WT mice should accelerate this phenotype. Our ongoing preliminary study, whereby a 6-week treatment with P4+E2 induced large inguinal hernia in all WT mice (FIG. 7A), supports the following experiment. Long-term (8 weeks or longer) treatment with E2 only is anticipated to cause hernias in up to half of WT mice based on previous findings[23-25]. We will determine whether P4+E2 treatment over 12 weeks will give rise to larger hernias in a higher number of mice compared with E2-only treatment. We will determine whether the addition of RU486 blocks muscle fibrosis and hernia formation in E2 or P4+E2 groups. The following treatment groups will establish the roles of P4 and PGR in LAM fibrosis and hernia formation: (1) Placebo, (2) E2 only, (3) P4+E2, (4) E2+RU486, and (5) P4+E2+RU486 (n=15/group). See Statistical Methods above for sample size calculation. Hernia surface area will be measured using a digital caliper and calculated as previously described (length×width)[19]. At the designated endpoints, LAM and UAM (control) from each mouse will be resected, with one-half of the tissue snap-frozen in liquid nitrogen, and the other half fixed in 4% phosphate-buffered paraformaldehyde for histological and IHC analyses (see below). All tissue and serum (for P4/E2 levels) samples will be collected between 10:00 AM and noon to avoid possible variability in daily hormone fluctuations. Our study showed that treatment of WT male mice with P4+E2 starting at the age of 9 weeks significantly induced hernia formation in all mice in a week and induced large hernias (>225 mm$^2$) within just 2-4 weeks, whereas E2-only treated mice induced the development of small hernias (125-175 mm$^2$) and P4-only treatment did not induce any hernia formation after 10-12 weeks (FIG. 7A). We will continue to complete the rest of the proposed study in this subaim. We will also assess whether and extent of muscle fibrosis and atrophy will be induced in P4+E2-induced large hernias and E2-induced small hernias. Experiment 1a2: Do P4 antagonists RU486, UPA, or ZK299 arrest or reverse LAM fibrosis, muscle atrophy, and hernia formation in male Arom$^{hum}$ mice? P4 antagonists show various levels of selectivity for PGR. In addition to being a strong P4/PGR antagonist, RU486 has anti-glucocorticoid effects via glucocorticoid receptor (GR)[36]. To assess whether the therapeutic effect of RU486 is mediated via P4/PGR antagonism, it will be used to prevent P4/E2-induced hernia formation in WT mice (Experiment 1a1). Additionally, because GR expression in LAM tissues of WT or Arom$^{hum}$ mice is similar, GR is an unlikely mediator of the RU486 effect. The use of UPA and ZK299 with minimal or no antiglucocorticoid properties will provide additional evidence for the role of P4/PGR as the mediator of hernia formation[74]. RU486 or UPA does not inhibit aromatase enzyme activity, but ZK299 was reported to be a weak aromatase inhibitor[75]. The therapeutic effects of RU486 and UPA rule out that aromatase inhibition is the responsible mechanism (FIG. 7B). The use of 3 distinct P4/PGR antagonists with different properties will establish the role of PGR in muscle fibrosis and hernia. Long-term administration of RU486 to men for more than 2 years is well tolerated, which makes it a realistic candidate for hernia treatment[47]. UPA has very high PGR selectivity with extremely low anti-glucocorticoid activity[36]. There is an extremely low (<1:1,000) risk of idiopathic severe liver damage associated with UPA treatment in women[76]. ZK299 is a highly PGR-selective pure P4 antagonist with significant liver toxicity associated with its long-term use[77]. While RU486 has the highest potential for clinical use in men in the future, UPA and ZK299 will be used to gain more mechanistic insights. Preliminary data suggest that treatment with RU486 or UPA starting at 3 weeks of age (before hernia development) for 12 weeks prevented LAM tissue fibrosis, myocyte atrophy, and inguinal hernias in Arom$^{hum}$ mice (FIGS. 7A-7E). Since ZK299 treatment showed the strongest inhibition of the expression of P4/PGR-responsive and fibrotic genes induced by E2+R5020 in Arom$^{hum}$ LAM fibroblasts compared to RU486 or UPA treatment (FIG. 9), we expect that ZK299 treatment will also prevent hernia formation in Arom$^{hum}$ mice.

Figure 13:
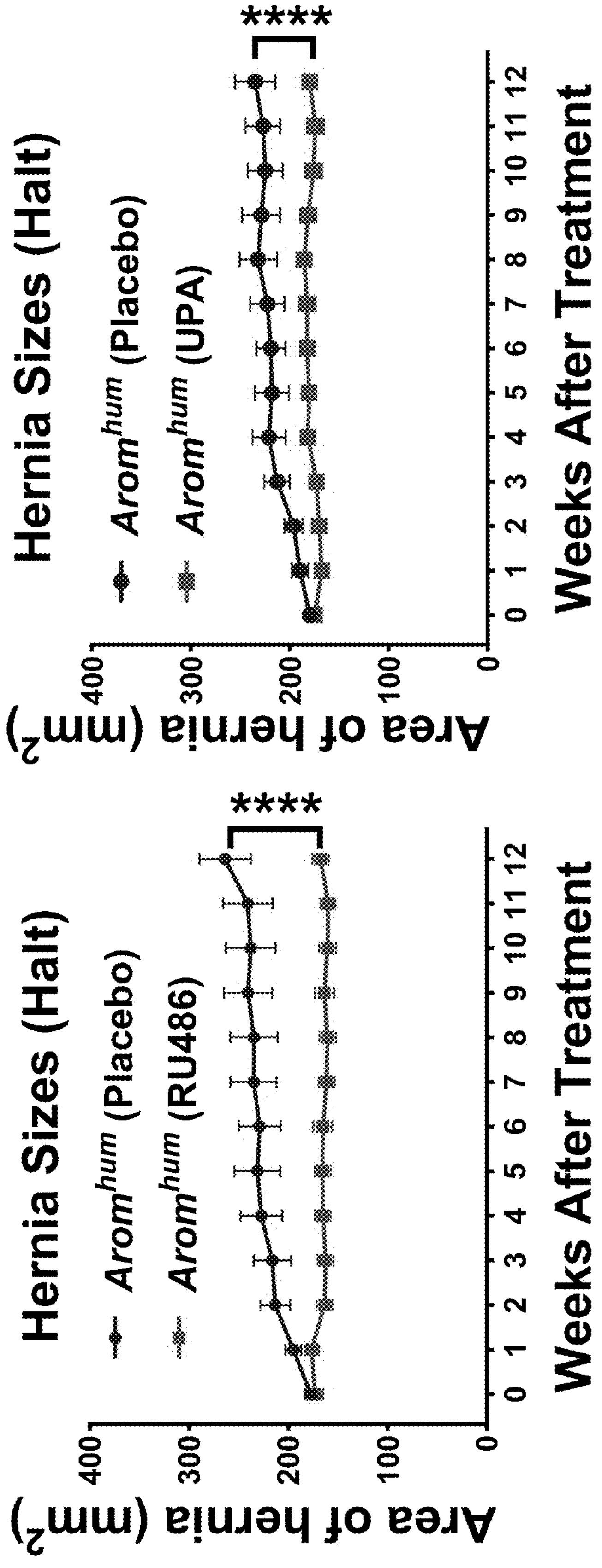
FIG. 13 shows the Arom$^{hum}$ mice treated with RU486 (left) and UPA (right) for halting the progression of small/medium-sized hernias. Hernia area measurements showed that the treatment with RU486 or UPA halted the progression of small/medium-sized hernias in Arom$^{hum}$ mice during a 12-week treatment (n=10). The treatment started when small/medium-sized hernias were formed. $****p<0.0001$.

Hernias will be classified as small, medium, or large if the bulging area through muscle tissue is 125-175 mm$^2$, 175-225 mm$^2$, or >225 mm$^2$, respectively. First, we will treat Arom$^{hum}$ mice with small hernias using 12-week subcutaneous release pellets containing RU486 (37.5 mg/pellet)[73, 78], UPA (22.5 mg/pellet)[79, 80], ZK299 (22.5 mg/pellet)[81, 82], or placebo for 12 weeks. We will assess whether muscle fibrosis, atrophy, and hernia are arrested or reversed. Then, if early treatment with RU486, UPA, or ZK299 is found to arrest small hernias, we will delay the initiation of treatment to determine whether RU486/UPA/ZK299 can arrest or reverse the growth of medium or large hernias. Hernia development will be monitored by visual inspection twice a week for 12 weeks after administering RU486, UPA, or ZK299 and will be reported as hernia incidence using Kaplan-Meier curve analysis. Hernia size will be measured. After completion of treatment, the mice will be dissected, and LAM, UAM (control), and serum will be collected. A total of 100 mg of tissue (LAM and UAM) will be obtained and frozen for measurement of tissue E2/P4. Circulating and tissue E2/P4 levels will be measured using LC-MS[2]. We will use immunoblotting and IHC to determine PGR expression in LAM and UAM tissues. PGR target gene expression (Greb1, Cyp7b1) will be measured in paraformaldehyde-fixed LAM tissues using RNAScope and IHC. Administration of the P4 antagonist RU486 or UPA halted the growth of small- and medium-size hernias in all treated Arom$^{hum}$ mice, whereas placebo-treated Arom$^{hum}$ mice continued to develop large hernias (FIG. 13). We will continue to complete the rest of the proposed study in this subaim. We will also assess whether muscle fibrosis, atrophy, and large hernia are halted.

Does RU486/UPA/ZK299 administration inhibit fibroblast proliferation, collagen formation, and fibrosis? The effect of RU486, UPA, or ZK299 treatment on LAM fibroblast proliferation will be measured by Ki67 IHC staining and PCNA immunoblotting. We will use H&E staining to morphologically assess stromal fibrosis in LAM tissue. Masson's trichrome staining will be performed to further determine the extent of ECM deposition in hernia tissue, and fibrotic areas (blue color) will be quantified using ImageJ software. The amount of type I collagen (COL1A1), the major collagen secreted by fibroblasts of fibrotic tissue, will be determined by IHC and immunoblotting. We will also examine the expression of the newly identified P4/PGR-induced fibrosis-related genes (Adamtsl1, Col12a1, Col14a1) in LAM and UAM tissue after treatment with RU486, UPA, or ZK299 using qPCR and IHC. These results will determine if P4 antagonist treatment reduces LAM fibroblast proliferation, collagen excess, and fibrosis. Total collagen (hydroxyproline) content, a major component of ECM, will be measured by Dr. Richard L. Lieber (co-PI), an expert in muscle ECM and cellular mechanisms that contribute to fibrosis[83-89].

Does RU486/UPA/ZK299 inhibit or reverse muscle atrophy and restore muscle strength? We will histologically determine cross-sectional area (CSA) of myofibers in Masson's trichrome-stained LAM and UAM tissue sections employing Axiovision 4.5 software (ZEISS) to assess LAM atrophy. The myofiber marker myosin heavy chain (MYH) will be measured in LAM and UAM by qPCR and immunoblotting[19]. The muscle fibers we will assess are composed of transverse abdominis and the internal and external oblique muscles in healthy LAM and UAM as well as the atrophied remnants of these myofibers in Arom$^{hum}$ LAM. We will quantify the LAM architectural properties (e.g., physiologic CSA, fascicle length, and sarcomere length) to predict the maximum force-generating capacity of LAM tissue[90, 91]. Muscle architecture analysis will be performed by Dr. Lieber (co-PI), an expert in muscle biomechanics[90, 91]. Histologic assessment will be performed by Dr. David J. Escobar (co-PI), a pathologist at Northwestern. The results will determine whether treatment with RU486, UPA, or ZK299 inhibits LAM tissue muscle atrophy or reverses muscle strength. For statistical methods and power analyses, see Statistical Methods above.

Hypothesis 1b

Figure 10:
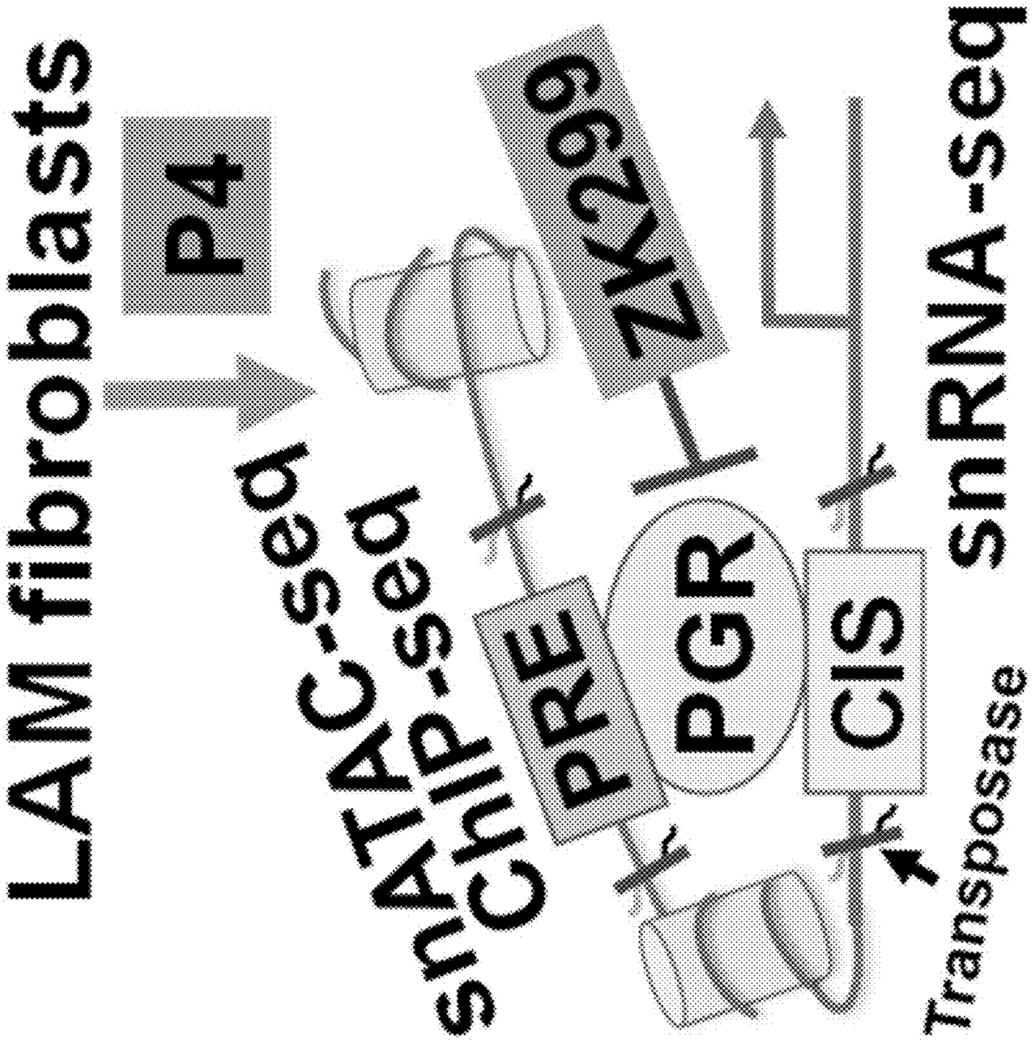
FIG. 10 shows the working model for Hypothesis 1b. CIS, cis-regulatory elements.

P4-activated PGR interacts with specific regions of chromatin and drives the expression of a distinct set of genes in LAM HAFs in Arom$^{hum}$ mice, leading to fibroblast proliferation, ECM production, and hernia formation. We expect that some of these genes are potential targets for novel therapeutics to prevent or reverse recurrent inguinal hernias. We will determine the PGR cistrome together with multiomic profiling of epigenome and transcriptome in ZK299-treated LAM fibroblasts from Arom$^{hum}$ mice at the single-cell level (FIG. 10).

Rationale

Evidence from PGR- and ESR1-positive breast cancer tissues reveals the critical roles of coordinated genome-wide PGR-chromatin interactions, epigenetic regulation, and transcriptional activity in disease development[92]. However, chromatin-based gene regulation by PGR in LAM fibroblasts is unknown, thereby hindering our understanding of the mechanisms underlying LAM fibroblast proliferation, ECM production, and hernia formation. Fibroblasts are usually quiescent, but persistent stimuli may epigenetically transform these into fibrosis-associated fibroblasts with enhanced proliferative properties and ECM production[93]. LAM fibroblasts are quiescent in WT mice and become fibrotic HAFs in Arom$^{hum}$ mice under the influence of P4-activated PGR, induced by E2/ESR1. Indeed, LAM PGR-rich HAFs from Arom$^{hum}$ expressed the highest levels of PGR, grew faster and produced more ECM compared to LAM fibroblasts from WT mice (FIGS. 4, 5, 8). snRNA-seq and snATAC-seq will be performed in identical cells isolated directly from LAM tissues of Arom$^{hum}$ mice treated with placebo or ZK299 for 12 weeks (n=3/group). Single-cell suspensions of LAM tissues will be obtained as described in our recent publication[22]. To perform PGR ChIP-seq in an in vivo setting, we will directly isolate LAM tissue HAFs that exclusively express PGR using fluorescence-activated cell sorting (FACS) and an antibody against PDGFRA (FIG. 4D, 4F). PDGFRA is expressed in most PGR-expressing LAM fibroblasts (FIG. 4, panels B, C, FIG. 11)[22]. We previously used PDGFRA antibody (Invitrogen 11-1401-82) to isolate LAM fibroblasts from WT and Arom$^{hum}$ mice by flow cytometry[22]. We anticipate obtaining ~6.6×10$^6$ single suspended cells in LAM tissue from one Arom$^{hum}$ mouse, of which 45% (~3×10$^6$) are PDGFRA-positive fibroblasts. Since ~9×10$^6$ cells are needed for a single PGR ChIP-seq, we will use 12 Arom$^{hum}$ mice for one set of PGR ChIP-seq (4 conditions). Each experiment will be repeated 3 times, requiring a total of 42 (2×3+12×3) mice.

Proposed Experiments

Experiment 1b1: We will perform multiomic analyses of paired snRNA-seq and snATAC-seq from the same set of LAM single-suspended cells from Arom$^{hum}$ male mice treated with placebo or ZK299 (n=3/group). We previously identified two HAF clusters in LAM tissues of Arom$^{hum}$ mice using scRNA-seq analysis (FIG. 4, panel A)[22]. We will analyze epigenetic changes responsible for differential gene expression after P4/PGR antagonist ZK299 treatment in HAFs at the single-cell level. Nuclei from each LAM tissue will be isolated using Chromium Nuclei Isolation Kit (10xGenomics) and submitted to the NUSeq core for paired multiomic assays. The NUSeq core routinely generates libraries using the Chromium Next GEM Single Cell Multiome ATAC+Gene Expression Reagent Kit. Sequencing will be performed (Illumina NovaSeq) to obtain a depth of >30,000 reads/cell for each library. Putative regulatory targets will be identified by direct linkage of differentially accessible DNA regions to proximal differentially expressed (DE) genes in the same nucleus. These in vivo assays will be performed under the physiological conditions, at which endogenous P4 activates PGR responsible for LAM fibrosis.

Experiment 1b2: Using ChIP-seq, we will map global PGR binding sites on chromatin from freshly (FACS)-isolated PDGFRA-positive LAM fibroblasts from 36 Arom$^{hum}$ male mice treated for 3 h with vehicle, P4 (100 nM), P4+E2 (10 nM), or P4+E2+ZK299 (1 μM). For the last 2 conditions, we added E2 to maintain PGR expression. The age of Arom$^{hum}$ mice will match the mouse ages in Experiment 1b1. We have successfully performed PGR ChIP-seq in human cells and tissues[78, 94]. We will use an antibody validated for PGR ChIP-seq in mouse tissue (Thermo Fisher, cat #MA5-12658) and perform optimization studies (ChIP-immunoblot and conventional ChIP) with this antibody in primary LAM fibroblasts. ChIP DNA will be prepared using the SimpleChIP Enzymatic Chromatin IP Kit (Cell Signaling); libraries will be prepared using Kapa Hyper Prep Kits. Library quality will be assessed using the Agilent 2100 Bioanalyzer. Sequencing will be performed at the NUSeq core to obtain 25 million single-end 75-bp reads per sample. By integrating the genome-wide open chromatin regions, global PGR-binding sites, and DE transcripts/genes, we will define regulatory regions that specifically activate or repress gene transcription in LAM fibroblasts of male Arom$^{hum}$ mice.

Bioinformatics analysis for snRNA-seq, snATAC-seq, PGR ChIP-seq, and their integration will be performed by Dr. Yang Dai's lab at the University of Illinois at Chicago. Raw reads from snRNA-seq and snATAC-seq will be processed using Cell Ranger Arc (10x Genomics)[98] with the mouse reference genome (mm10). The output will be integrated using various tools in Seurat[99, 100] for clustering cells and identifying LAM fibroblast subtypes and detecting DE transcripts/genes between specific clusters in LAM fibroblast from male Arom$^{hum}$ treated with placebo or ZK299. Differentially accessible regions between cell clusters of interest will be identified and overrepresented motifs will be detected. For ChIP-seq data, sequencing reads will be evaluated using FastQC[101] and trimmed reads will be aligned to the mouse genome using Bowtie[102]. Peak calling will be performed using HOMER[103]. The peak intervals will be merged and differential binding (DB) sites of the consensus overlapping regions across all replicates will be identified using DiffBnd[104]. Motif analysis will be performed using HOMER to identify additional transcription factors. We will use binding and expression target analysis (BETA) to integrate the DB sites and DE transcripts/genes[105] and open accessible regions in fibroblast cell types identified from the single-cell data. This will allow us to prioritize PGR binding sites that directly regulate functional mRNA transcription and pathways that coordinate the concerted series of molecular events leading to increased LAM fibrosis. This integrated approach will distinguish active vs. repressive regulators and reduce false-positive findings, thus enabling the design of effective validation experiments. Target genes will be validated using qPCR, RNAScope, immunoblotting, and immunofluorescence (IF). Receptor binding sites will be confirmed using the traditional ChIP assay. Functional analysis of these genes will be performed in vitro (e.g., siRNA knockdown or gene overexpression) to determine their effects on LAM fibrosis and hernia formation.

Expected Results

We expect that in all WT mice, P4+E2 treatment will induce hernia formation earlier than E2-only treatment, which may induce hernia in a portion of mice treated long-term. RU486 will prevent P4+E2 or E2-induced inguinal hernia in WT mice. We anticipate that the P4 antagonists RU486, UPA, and ZK299 will prevent hernias if started as early as 3 weeks of age and will arrest further enlargement of or reverse small- and medium-size hernias in Arom$^{hum}$ mice. ZK299 has the highest potential to reverse existing hernias and restore normal anatomy. It is less likely that RU486, UPA, or ZK299 will completely reverse large inguinal hernias with protruding muscle areas≥225 mm$^2$, compared with small or mid-sized hernias. Based on the literature, P4 levels in the circulation and LAM tissues will likely not change after RU486, UPA, or ZK299 treatment in Arom$^{hum}$ mice[106]. The combined snRNA-seq, snATAC-seq, and PGR ChIP-seq strategy will provide a functional understanding of how the nuclear receptor PGR, in cooperation with accessible chromatin regions, determines the transcriptional activities of select genes in specific cell types (e.g., HAFs) to induce LAM HAF proliferation and ECM production leading to hernia formation. We expect to define specific chromatin accessibility and its associated unique gene expression profile in the specific LAM fibroblast clusters from Arom$^{hum}$ mice treated with placebo or ZK299. Using ChIP-seq in P4+(E2)-treated LAM fibroblasts, we anticipate identifying a distinct set of PGR binding sites that are modified by specific chromatin accessibility data from intact mice and drive the transcription of proliferative and profibrotic genes. We expect that ZK299 treatment will block or partially reverse P4(+E2)-induced PGR binding and open chromatin regions, and alter gene expression profiles (e.g., P4-responsive and fibrotic genes) in LAM fibroblasts[107]. The addition of motif analysis data will allow us to more accurately identify critical and novel transcription factors that are key for LAM fibroblast activation, fibrosis, and eventually hernia formation.

In addition to acting as a P4/PGR-antagonist, RU486 also has anti-glucocorticoid properties[108]. It is extremely unlikely, however, that the glucocorticoid/GR pathway is involved in hernia formation in Arom$^{hum}$ mice because GR expression in LAM tissues is similar in WT and Arom$^{hum}$ mice. Additionally, circulating or tissue levels of corticosterone (the main GR ligand in mice) levels are not different between WT and Arom$^{hum}$ mice. Treatment of Arom$^{hum}$ mice with more PGR-selective P4 antagonists UPA and ZK299, with minimal or no anti-glucocorticoid effects, will further clarify this possibility[36, 74]. Despite these efforts, RU486, UPA, or ZK299 may prevent or reverse muscle fibrosis or hernia formation via non-PGR-dependent pathways. Thus, we propose a parallel study in Example 2, in which we will knock out PGR selectively in PDGFRA-expressing LAM fibroblasts. PGR ChIP-seq, snATAC-seq, snRNA-seq, and integrative bioinformatic analyses are technically challenging experiments. Our team, however, has extensive experience in this area[22, 41, 78, 94, 97, 109-113], and we expect to encounter no obstacles.

Example 2. Determine Whether Conditional Knockout of PGR in LAM Fibroblasts Reduces Fibrosis, Myocyte Atrophy, or Hernia and Associate the Mechanistic Mouse Data With Human Disease Hypothesis 2a PGR, which is highly induced by E2/ESR1 in LAM hernia-associated fibroblasts (HAFs) (FIG. 5), is responsible for LAM HAF proliferation, ECM formation, myocyte atrophy, and hernia formation.

Rationale

Although circulating and LAM P4 levels are similar in WT and Arom$^{hum}$ mice (FIG. 6), the Pgr gene is differentially expressed in LAM HAFs of Arom$^{hum}$ compared with quiescent fibroblasts from WT LAM tissue (FIG. 4, panels B, D). IHC showed that PGR was absent from WT LAM tissues but highly expressed in LAM fibroblasts of Arom$^{hum}$ mice (FIG. 4, panel F). P4/PGR is required for LAM fibroblast proliferation (FIGS. 7A, 8A-C). RU486 or UPA significantly inhibits the expression of PGR-responsive and fibrotic genes (FIG. 8, panels E, FIG. 9). Strikingly, RU486 or UPA prevented hernia formation in vivo (FIGS. 7A-7E). Highly expressed PGR in LAM fibroblasts of Arom$^{hum}$ mice may drive HAF proliferation, fibrosis, muscle atrophy, and hernia development via activation of PGR-rich HAFs.

Background, Data, and Discussion

Figure 11:
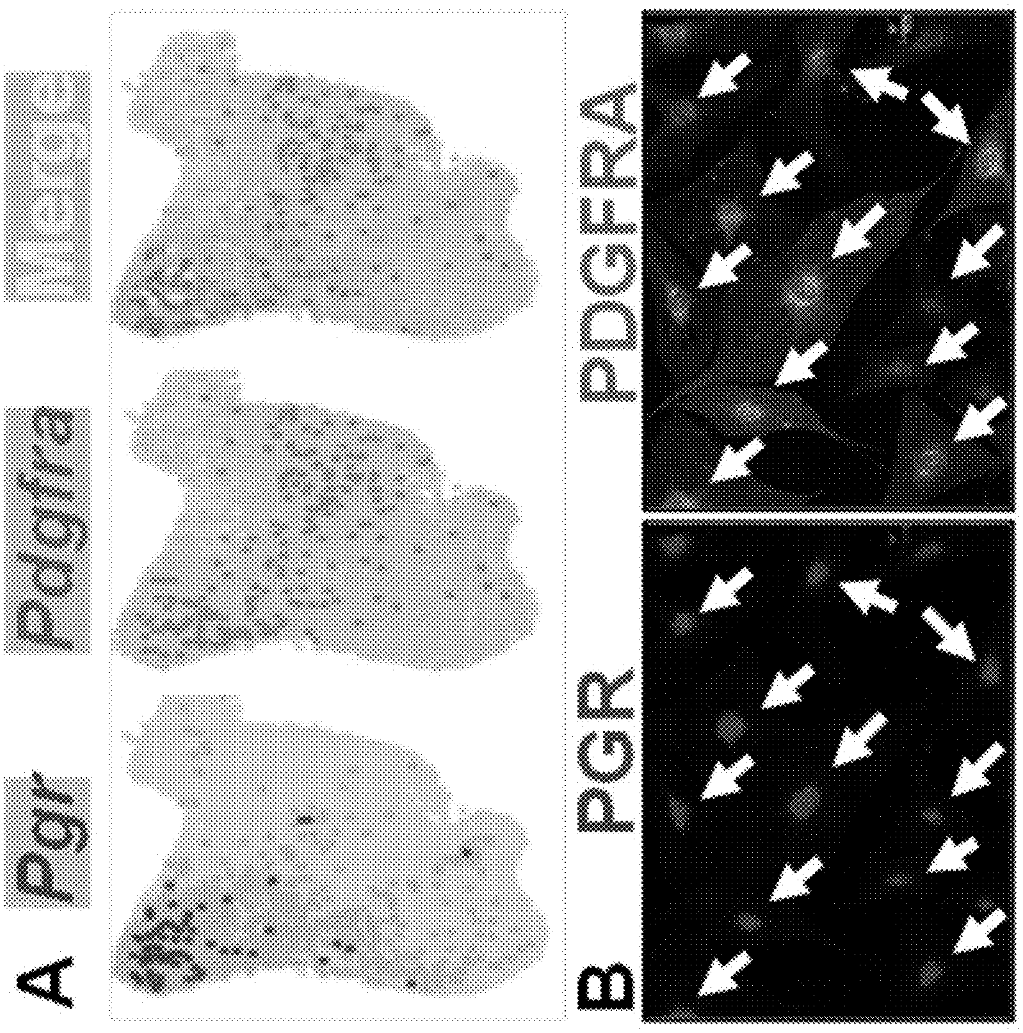
FIG. 11 shows (A) UMAP feature plots showing overlapping expression of Pgr and Pdgfra in fibroblasts from LAM of Arom$^{hum}$ mice (n=3), and (B) PGR is expressed in PDGFRA-positive LAM fibroblasts from Arom$^{hum}$ mice (n=5). Immunocytochemistry (ICC) staining of PGR and PDGFRA.

In vivo, UMAP feature plots showed that Pgr and Pdgfra were colocalized in PGR-positive LAM fibroblasts (FIG. 11, panel A)[40]. Additionally, LAM fibroblasts that were isolated via differential plating from LAM tissues of Arom$^{hum}$ mice (n=5) were analyzed using multicolor immunocytochemistry (ICC). We found that PGR is highly expressed in LAM fibroblasts and co-localized with PDGFRA in the majority (>95%) of PDGFRA-positive fibroblasts (FIG. 11, panel B). This remarkable co-expression pattern will enable us to test the role of PGR in hernia formation using a genetic approach employing Pdgfra-cre transgenic mice. Here, we will define the role of fibroblast-specific PGR in mediating the effects of E2/ESR1 on LAM fibrosis, myocyte atrophy, and hernia formation. Prevention of fibrotic muscle atrophy and hernia via genetic disruption of PGR in PDGFRA-positive fibroblasts will provide rigorous evidence for the role of P4/PGR action in muscle fibroblasts in hernia formation.

Proposed Experiments

Experiment 2a: Does fibroblast-specific ablation of PGR prevent LAM tissue fibrosis and hernia in Arom$^{hum}$ mice? We will obtain floxed PGR mice (Pgr$^{fl/fl}$) from Dr. Francesco J. DeMayo (see letter)[40] and have obtained Pdgfra-cre mice from the Jackson Laboratory (Jax #013148). We will cross these two mice to genetically ablate the Pgr gene only in mouse fibroblasts expressing PDGFRA (Pgr$^{-/-}$). In addition to confirmation with genotyping, we will also validate the efficiency of recombination (ablation) between the two loxP sites in fibroblasts using PDGFRA/PGR double immunofluorescence (IF) staining, which will be essential for interpreting the results. Once we confirm generation of the fPgr$^{-/-}$mouse, we will cross it with the Arom$^{hum}$ mouse to generate an Arom$^{hum}$ mouse lacking fibroblast PGR in LAM tissue and possibly other tissues (Pgr$^{-/-}$Arom$^{hum}$). fPgr$^{+/+}$-Arom$^{hum}$ and fPgr$^{+/-}$-Arom$^{hum}$ littermates will be used as controls.

Do fPgr$^{-/-}$-Arom$^{hum}$ mice exhibit decreased P4/PGR action in muscle fibroblasts and not in other cell types? PGR mRNA and protein will be assessed in LAM tissue homogenates by qPCR and immunoblotting. Since LAM homogenates are mixtures of fibroblasts and myocytes, the extent of PGR deletion in fibroblasts may not be shown precisely. LAM tissue will be paraffin-embedded and sectioned for IHC localization of PGR to confirm deletion in fibroblasts. To define if PGR is fully deleted in fibroblasts, primary LAM fibroblasts (passage 0) will be isolated and cultured from fPgr$^{-/-}$-Arom$^{hum}$ mice and controls by differential plating[19, 22]. PGR mRNA and protein levels will be measured using qPCR and immunoblotting. We routinely isolate and culture primary fibroblasts from LAM tissue[19, 22]. To confirm that the fibroblast-specific deletion of PGR decreases P4/PGR action, P4/PGR-responsive mRNA/protein expression (Greb1, Cyp7b1) will be determined in LAM and UAM fibroblasts after P4 (100 nM)+E2 (10 nM) treatment for 48 h (E2 will be included to induce PGR levels). We will measure serum and muscle tissue P4 levels by LC-MS$^2$ to verify the presence of the native PGR ligand, P4, in vivo in LAM tissue.

Does fibroblast-specific ablation of PGR decrease fibroblast proliferation and profibrotic gene expression? In vivo, LAM fibroblast proliferation will be measured by Ki67 IHC staining and PCNA immunoblotting of tissues from $fPgr^{-/-}$-$Arom^{hum}$ mice or their littermate controls. mRNA and protein levels of fibrosis-related genes (e.g., Adamtsl1, Col1a1, Col12a1, Col14a1) will be assessed in LAM/UAM tissues by qPCR and IHC and in P4+E2-treated primary LAM fibroblasts using immunoblotting.

Does fibroblast-specific ablation of PGR diminish LAM fibrosis, atrophy, and hernia formation? Hernia formation will be monitored twice a week by visual inspection from 3 to 26 weeks of age. Hernia incidence, time to hernia onset, and hernia surface area will be analyzed by Kaplan-Meier plot. At euthanasia, muscle-fiber CSA and stromal ECM will be measured in Masson's trichrome-stained (MTS) sections, and COL1A1 will be determined by IHC and immunoblotting to confirm the results from MTS. Total collagen content in LAM tissues will be defined by hydroxyproline assay and LAM tissue architecture properties will be analyzed, as described under Experiment 1a2. For statistical methods and power analyses, see Statistical Methods above.

Hypothesis 2b

The histologic and P4/PGR-related molecular changes in LAM tissue of $Arom^{hum}$ male mice are present in tissues of a subset of elderly men with inguinal hernia.

Rationale

We will test whether the histologic and P4/PGR-related molecular changes observed in the $Arom^{hum}$ mice are present in a subset of elderly men with hernias. Previously, we found that men with inguinal hernia show higher ESR1 expression, proliferative activity, and ECM formation in LAM fibroblasts in biopsied hernia tissue, similar to those observed in the $Arom^{hum}$ mouse hernia model (FIG. 2)[19]. Serum P4 levels in men with hernia persist at detectable levels during their lifetime (FIG. 6, panel C). In the $Arom^{hum}$ mouse model, P4-activated PGR induced PGR-responsive and profibrotic gene expression, leading to LAM fibroblast proliferation, fibrosis, muscle atrophy, and hernia formation (FIGS. 4, 5, 7A-7E, 8-9). Thus, we will examine these molecular signatures in human tissues and compare them to those of $Arom^{hum}$ mice. We will further define the correlation between ESR1 and PGR or PGR and Ki67 in LAM tissue of the herniated region in men.

Background, Data, and Discussion

Feature plots showed PGR expression in the majority of fibroblasts from human skeletal muscle tissue in the publicly available Human Protein Atlas database (FIG. 12, panel A). Our long-time co-investigator Dr. Jonah J. Stulberg, Vice-Chair of Research, Department of Surgery at University of Texas Health Sciences Center of Houston, has collected fibrotic LAM tissue in the hernia sites and adjacent healthy LAM tissues at 1 cm to hernia from 11 men undergoing hernia repair surgery (50-76 years of age). Healthy LAM tissue consisted of normal muscle fibers and stromal tissue, whereas LAM at hernia wall consisted of fibrotic tissue with islands of atrophic myocytes (yellow arrows; FIG. 2). This histologic picture is almost identical to that seen in similar tissues from $Arom^{hum}$ mice (FIG. 2). PDGFRA IHC staining was also significantly higher in hernia site LAM tissues (FIG. 12, panel B). Consistent with $Arom^{hum}$ mice, human PGR expression was strikingly higher in the LAM fibroblasts from hernia sites compared with adjacent healthy controls (FIG. 12, panels C and D). Similarly, fibroblast proliferation quantified by Ki67 IHC was increased in LAM tissues from hernia sites compared with adjacent healthy muscles (FIG. 12, panel E). These findings suggest a link between enhanced PGR action and LAM fibrosis associated with inguinal hernias in men.

Proposed Experiments

Experiment 2b: Are PGR expression and the correlation between PGR, ESR1, or Ki67 in human hernia/LAM tissues consistent with those observed in the mouse model of hernia? To define whether the mouse abdominal muscle tissue levels of P4, PGR, and Ki67 and the correlation between ESR1 and PGR or PGR and Ki67 mirror their expression/production pattern in men, informed consent will be obtained to collect blood samples and biopsies of LAM tissue from the hernia wall and healthy-appearing LAM tissue 1 cm adjacent to hernia sac from men (>50 years) undergoing surgery for inguinal hernia, as well as healthy-appearing LAM tissue of age-matched hernia-free men undergoing lower abdominal surgery for other benign indications. These men will be required to have intact and healthy abdominal muscle tissue. Note that the risks of obtaining additional UAM samples from men undergoing hernia surgery do not justify the research benefits, and thus UAM will not be collected for this study. Exclusion criteria will include men with muscular dystrophy, recent abdominal surgeries, or cancer within the previous five years and men receiving steroid hormone therapy for various reasons. We will evaluate mRNA (qPCR, RNAScope) and protein levels (immunoblotting, IHC) of ESR1, PGR, and PGR-responsive (GREB1, CYP7B1) and fibrosis-related genes (ADAMTSL1, COL1A1, COL12A1, COL14A1) in the human tissue samples. We anticipate augmenting the spectrum and pathologic relevance of PGR-target and profibrotic gene signatures based on the results from the ChIP-seq and multiomic experiments described under Experiments 1b1 and 1b2. P4 and E2 levels in both tissue and serum will be measured by LC-$MS^2$. A 36% increase in ESR1 in hernia LAM tissue compared with hernia-free LAM tissue can be reliably detected with approximately 6 men per group, assuming a coefficient of variation of 50% and a two-tailed, $\alpha=0.05$-level, and independent-sample t-test[19]. We plan to recruit a total of 30 men for each group (30 men with hernia and 30 hernia-free men) to ensure a realistic chance of obtaining meaningful results. We will use ANOVA followed by Tukey's or Chi-square test of independence analyses for comparing the mRNA and protein levels of these genes in 3 groups of tissues: (1) atrophic LAM tissue at the hernia wall, (2) normal-appearing LAM 1 cm adjacent to the hernia, and (3) LAM tissue from hernia-free men. We will use the Pearson method to determine whether tissue P4 and E2 levels, PGR/ESR1 expression, PGR/Ki67 expression, and PGR-target and fibrosis-related gene signatures are correlated in men with hernias.

Example 2: Expected Results

We anticipate that fibroblast-specific ablation of PGR in $Arom^{hum}$ mice will prevent or significantly delay LAM fibrosis, muscle atrophy, and hernia formation. Because P4 acts via PGR in the LAM fibroblast, PGR ablation will have a nearly complete protective effect against hernia formation. We expect that LAM fibroblasts in $fPgr^{-/-}$-$Arom^{hum}$ mice will become less fibrotically active, i.e., show decreased proliferation and ECM production. Fibroblast-selective PGR disruption will restore the physiologic properties and strength of LAM tissue to normal levels. In a subset of elderly men with hernias, we expect that the tissue levels E2 and P4 and expression patterns of ESR1, PGR, and PGR target genes in LAM tissue will be similar to those observed in Arom$^{hum}$ mice. We expect that LAM E2 levels, but not LAM P4 levels, will be higher in the LAM tissue of men with hernias compared with age-matched hernia-free men. We anticipate that PGR will positively correlate with ESR1 or Ki67 in hernia/LAM fibroblasts of men with hernias and will be higher in LAM tissue in these men compared with age-matched hernia-free men. We also expect that P4/PGR-target and fibrotic gene signatures will follow these patterns. Healthy LAM tissue biopsies obtained adjacent to hernias are expected to show a similar gene expression profile to those of hernia-free men.

We have almost 20 years of experience in the described techniques[19, 22, 57, 58, 114-119]. PDGFRA is expressed in most LAM fibroblasts including PGR-positive fibroblasts (FIG. 4, panels B, D, and FIG. 11). We have successfully deleted ESR1 in LAM fibroblasts of Arom$^{hum}$ mice using Pdgfra-cre mice (FIG. 3, panel A). Thus, we can address the potential challenges associated with PGR deletion in LAM fibroblasts. In the human study, we will increase the sample size if we see a large subject-to-subject variation.

SUMMARY

The examples and experiments described herein will provide mechanistic plausibility for starting clinical trials to test the potential of RU486 (mifepristone) for treating inguinal hernias in surgically challenging cases, those accompanied by long-term postoperative pain, infection, and a high rate of recurrence. Our studies will reveal the underlying molecular mechanisms for hernia development in a subset of men and provide the basis for developing novel pharmacological approaches for preventing recurrence of inguinal hernia in high-risk individuals. In the future, we will perform multiomic assays in LAM tissue from men with or without hernia to reveal unique epigenome and transcriptome patterns associated with hernia formation at the single-cell level. We will also extend our research to define the functions of E2/ESR1 and P4/PGR in idiopathic lung fibrosis, where we found ESR1 and PGR are highly expressed (data not shown).

REFERENCES

1. Kingsnorth A, LeBlanc K. Hernias: inguinal and incisional. Lancet. 2003;362(9395):1561-71. doi: 10.1016/S0140-6736(03)14746-0. PubMed PMID: 14615114.
2. Primatesta P, Goldacre MJ. Inguinal hernia repair: incidence of elective and emergency surgery, readmission and mortality. International journal of epidemiology. 1996;25(4):835-9. PubMed PMID: 8921464.
3. Aasbo V, Thuen A, Raeder J. Improved long-lasting postoperative analgesia, recovery function and patient satisfaction after inguinal hernia repair with inguinal field block compared with general anesthesia. Acta anaesthesiologica Scandinavica. 2002;46(6):674-8. PubMed PMID: 12059890.
4. Bay-Nielsen M, Kehlet H, Strand L, Malmstrom J, Andersen FH, Wara P, Juul P, Callesen T, Danish Hernia Database C. Quality assessment of 26,304 herniorrhaphies in Denmark: a prospective nationwide study. Lancet. 2001;358(9288):1124-8. doi: 10.1016/S0140-6736 (01) 06251-1. PubMed PMID: 11597665.
5. Jenkins JT, O'Dwyer PJ. Inguinal hernias. BMJ. 2008; 336(7638):269-72. doi: 10.1136/bmj.39450.428275.AD. PubMed PMID: 18244999; PMCID: 2223000.
6. Rutkow IM. Demographic and socioeconomic aspects of hernia repair in the United States in 2003. Surg Clin North Am. 2003;83(5):1045-51, v-vi. doi: 10.1016/S0039-6109(03) 00132-4. PubMed PMID: 14533902.
7. Matthews RD, Neumayer L. Inguinal hernia in the 21st century: an evidence-based review. Curr Probl Surg. 2008;45(4):261-312. doi: 10.1067/j.cpsurg.2008.01.002. PubMed PMID: 18358264.
8. Malangoni MR, M. The Biological Basis of Modern Surgical Practice. In: Townsend CJB, D.; Evers, M.; Mattox, K.; eds., editor. Sabiston Textbook of Surgery. 18th ed. Philadelphia: Saunders Elsevier; 2008.
9. Matthews RD, Anthony T, Kim LT, Wang J, Fitzgibbons RJ, Jr., Giobbie-Hurder A, Reda DJ, Itani KM, Neumayer LA, Veterans Affairs Cooperative 456 Studies Program I. Factors associated with postoperative complications and hernia recurrence for patients undergoing inguinal hernia repair: a report from the VA Cooperative Hernia Study Group. Am J Surg. 2007; 194(5):611-7. doi: 10.1016/j.amjsurg.2007.07.018. PubMed PMID: 17936422.
10. Aasvang E, Kehlet H. Chronic postoperative pain: the case of inguinal herniorrhaphy. British journal of anaesthesia. 2005;95(1):69-76. doi: 10.1093/bja/aei019. PubMed PMID: 15531621.
11. Yang B, Jiang ZP, Li YR, Zong Z, Chen S. Long-term outcome for open preperitoneal mesh repair of recurrent inguinal hernia. International journal of surgery. 2015;19:134-6. doi: 10.1016/j.ijsu.2015.05.029. PubMed PMID: 26021274.
12. Hellspong G, Gunnarsson U, Dahlstrand U, Sandblom G. Diabetes as a risk factor in patients undergoing groin hernia surgery. Langenbecks Arch Surg. 2017;402(2): 219-25. doi: 10.1007/s00423-016-1519-8. PubMed PMID: 27928640.
13. Belghiti J, Durand F. Abdominal wall hernias in the setting of cirrhosis. Semin Liver Dis. 1997;17(3):219-26. doi: 10.1055/s-2007-1007199. PubMed PMID: 9308126.
14. Andraus W, Pinheiro RS, Lai Q, Haddad LBP, Nacif LS, D'Albuquerque LAC, Lerut J. Abdominal wall hernia in cirrhotic patients: emergency surgery results in higher morbidity and mortality. BMC Surg. 2015; 15:65. doi: 10.1186/s12893-015-0052-y. PubMed PMID: 25990110; PMCID: 4443633.
15. HerniaSurge G. International guidelines for groin hernia management. Hernia: the journal of hernias and abdominal wall surgery. 2018;22(1):1-165. doi: 10.1007/s10029-017-1668-x. PubMed PMID: 29330835; PMCID: 5809582.
16. Gianetta E, de Cian F, Cuneo S, Friedman D, Vitale B, Marinari G, Baschieri G, Camerini G. Hernia repair in elderly patients. Br J Surg. 1997;84(7):983-5. PubMed PMID: 9240142.
17. Gilbert AI. Hernia repair in the aged and infirmed. J Fla Med Assoc. 1988;75(11):742-4. PubMed PMID: 3204359.
18. Gunnarsson U, Degerman M, Davidsson A, Heuman R. Is elective hernia repair worthwhile in old patients? Eur J Surg. 1999;165(4):326-32. doi: 10.1080/110241599750006857. PubMed PMID: 10365833.

19. Zhao H, Zhou L, Li L, Coon VJ, Chatterton RT, Brooks DC, Jiang E, Liu L, Xu X, Dong Z, DeMayo FJ, Stulberg JJ, Tourtellotte WG, Bulun SE. Shift from androgen to estrogen action causes abdominal muscle fibrosis, atrophy, and inguinal hernia in a transgenic male mouse model. Proc Natl Acad Sci USA. 2018; 115(44): E10427-E36. doi: 10.1073/pnas. 1807765115. PubMed PMID: 30327348; PMCID: 6217386.
20. Bulun SE. Aromatase deficiency and estrogen resistance: from molecular genetics to clinic. Seminars in reproductive medicine. 2000;18(1):31-9. PubMed PMID: 11305285.
21. Bulun SE, Lin Z, Imir G, Amin S, Demura M, Yilmaz B, Martin R, Utsunomiya H, Thung S, Gurates B, Tamura M, Langoi D, Deb S. Regulation of aromatase expression in estrogen-responsive breast and uterine disease: from bench to treatment. Pharmacological reviews. 2005;57(3):359-83. doi: 10.1124/pr.57.3.6. PubMed PMID: 16109840.
22. Potluri T, Taylor MJ, Stulberg JJ, Lieber RL, Zhao H, Bulun SE. An estrogen-sensitive fibroblast population drives abdominal muscle fibrosis in an inguinal hernia mouse model. JCI Insight. 2022;7(9). Epub 2022 Apr. 20. doi: 10.1172/jci.insight. 152011. PubMed PMID: 35439171; PMCID: PMC9090253.
23. Burrows H. The occurrence of scrotal hernia in mice under treatment with oestrin. British Journal of Surgery. 1934;21:6.
24. Gardner WU. Sexual dimorphism of the pelvis of the mouse, the effect of estrogenic hormones upon the pelvis and upon the development of scrotal hernias. American Journal of Anatomy. 1936;59:25.
25. Hazary S, Gardner WU. Influence of sex hormones on abdominal musculature and the formation of inguinal and scrotal hernias in mice. Anat Rec. 1960;136:437-43. PubMed PMID: 14400391.
26. de Ronde W, de Jong FH. Aromatase inhibitors in men: effects and therapeutic options. Reprod Biol Endocrinol. 2011;9:93. Epub 2011 Jun. 23. doi: 10.1186/1477-7827-9-93. PubMed PMID: 21693046; PMCID: PMC3143915.
27. Dimitrov NV, Colucci P, Nagpal S. Some aspects of the endocrine profile and management of hormone-dependent male breast cancer. Oncologist. 2007;12(7): 798-807. Epub 2007 Aug. 4. doi: 10.1634/theoncologist.12-7-798. PubMed PMID: 17673611.
28. Yadav S, Giridhar KV, Leone JP, Leon-Ferre RA, Ruddy KJ. A practical guide to endocrine therapy in the management of estrogen receptor-positive male breast cancer. Breast Cancer Manag. 2021;10(3). doi: ARTN BMT59 10.2217/bmt-2021-0001. PubMed PMID: WOS: 000693205600001.
29. Beachler DC, de Luise C, Jamal-Allial A, Yin R, Taylor DH, Suzuki A, Lewis JH, Freston JW, Lanes S. Real-world safety of palbociclib in breast cancer patients in the United States: a new user cohort study. BMC Cancer. 2021;21(1):97. Epub 2021 Jan. 27. doi: 10.1186/s12885-021-07790-z. PubMed PMID: 33494720; PMCID: PMC7831235.
30. Smith EP, Boyd J, Frank GR, Takahashi H, Cohen RM, Specker B, Williams TC, Lubahn DB, Korach KS. Estrogen resistance caused by a mutation in the estrogen-receptor gene in a man. The New England journal of medicine. 1994;331(16):1056-61. Epub 1994 Oct. 20. doi: 10.1056/NEJM199410203311604. PubMed PMID: 8090165.
31. Rochira V, Carani C. Aromatase deficiency in men: a clinical perspective. Nat Rev Endocrinol. 2009;5(10): 559-68. Epub 2009 Aug. 27. doi: 10.1038/nrendo.2009.176. PubMed PMID: 19707181.
32. Brooks DC, Coon VJ, Ercan CM, Xu X, Dong H, Levine JE, Bulun SE, Zhao H. Brain Aromatase and the Regulation of Sexual Activity in Male Mice. Endocrinology. 2020;161(10). Epub 2020 Sep. 11. doi: 10.1210/endocr/bqaa137. PubMed PMID: 32910181; PMCID: PMC7485274.
33. Nilsson ME, Vandenput L, Tivesten A, Norlen AK, Lagerquist MK, Windahl SH, Borjesson AE, Farman HH, Poutanen M, Benrick A, Maliqueo M, Stener-Victorin E, Ryberg H, Ohlsson C. Measurement of a Comprehensive Sex Steroid Profile in Rodent Serum by High-Sensitive Gas Chromatography-Tandem Mass Spectrometry. Endocrinology. 2015;156(7):2492-502. Epub 2015 Apr. 10. doi: 10.1210/en.2014-1890. PubMed PMID: 25856427.
34. Stout EP, La Clair JJ, Snell TW, Shearer TL, Kubanek J. Conservation of progesterone hormone function in invertebrate reproduction. Proc Natl Acad Sci USA. 2010;107(26):11859-64. Epub 2010 Jun. 16. doi: 10.1073/pnas. 1006074107. PubMed PMID: 20547846; PMCID: PMC2900687.
35. Kim JJ, Kurita T, Bulun SE. Progesterone action in endometrial cancer, endometriosis, uterine fibroids, and breast cancer. Endocr Rev. 2013;34(1):130-62. doi: 10.1210/er.2012-1043. PubMed PMID: 23303565; PMCID: 3565104.
36. Islam MS, Afrin S, Jones SI, Segars J. Selective Progesterone Receptor Modulators-Mechanisms and Therapeutic Utility. Endocr Rev. 2020;41(5). Epub 2020 May 5. doi: 10.1210/endrev/bnaa012. PubMed PMID: 32365199; PMCID: PMC8659360.
37. Yang T, Bayless DW, Wei Y, Landayan D, Marcelo IM, Wang Y, DeNardo LA, Luo L, Druckmann S, Shah NM. Hypothalamic neurons that mirror aggression. Cell. 2023;186(6):1195-211 c19. Epub 2023 Feb. 17. doi: 10.1016/j.cell.2023.01.022. PubMed PMID: 36796363; PMCID: PMC10081867.
38. Yang T, Yang CF, Chizari MD, Maheswaranathan N, Burke KJ, Jr., Borius M, Inoue S, Chiang MC, Bender KJ, Ganguli S, Shah NM. Social Control of Hypothalamus-Mediated Male Aggression. Neuron. 2017;95(4): 955-70 c4. Epub 2017 Aug. 2. doi: 10.1016/j.neuron.2017.06.046. PubMed PMID: 28757304; PMCID: PMC5648542.
39. Yang CF, Chiang MC, Gray DC, Prabhakaran M, Alvarado M, Juntti SA, Unger EK, Wells JA, Shah NM. Sexually dimorphic neurons in the ventromedial hypothalamus govern mating in both sexes and aggression in males. Cell. 2013;153(4):896-909. Epub 2013 May 15. doi: 10.1016/j.cell.2013.04.017. PubMed PMID: 23663785; PMCID: PMC3767768.
40. Fernandez-Valdivia R, Jeong J, Mukherjee A, Soyal SM, Li J, Ying Y, Demayo FJ, Lydon JP. A mouse model to dissect progesterone signaling in the female reproductive tract and mammary gland. Genesis. 2010; 48(2):106-13. Epub 2009 Dec. 24. doi: 10.1002/dvg.20586. PubMed PMID: 20029965; PMCID: PMC2819579.
41. Liu S, Yin P, Kujawa SA, Coon JSt, Okeigwe I, Bulun SE. Progesterone receptor integrates the effects of mutated MED12 and altered DNA methylation to stimulate RANKL expression and stem cell proliferation in uterine leiomyoma. Oncogene. 2019;38(15):

2722-35. Epub 2018 Dec. 13. doi: 10.1038/s41388-018-0612-6. PubMed PMID: 30538295; PMCID: PMC6461478.

42. Mehrad M, Trejo Bittar HE, Yousem SA. Sex steroid receptor expression in idiopathic pulmonary fibrosis. Hum Pathol. 2017;66:200-5. Epub 2017 Mar. 17. doi: 10.1016/j.humpath.2017.02.012. PubMed PMID: 28300574.

43. Vafashoar F, Mousavizadeh K, Poormoghim H, Haghighi A, Pashangzadeh S, Mojtabavi N. Progesterone Aggravates Lung Fibrosis in a Mouse Model of Systemic Sclerosis. Front Immunol. 2021;12:742227. Epub 2021 Dec. 17. doi: 10.3389/fimmu.2021.742227. PubMed PMID: 34912332; PMCID: PMC8667310.

44. Lydon JP, DeMayo FJ, Funk CR, Mani SK, Hughes AR, Montgomery CA, Jr., Shyamala G, Conneely OM, O'Malley BW. Mice lacking progesterone receptor exhibit pleiotropic reproductive abnormalities. Genes Dev. 1995;9(18):2266-78. Epub 1995 Sep. 15. doi: 10.1101/gad.9.18.2266. PubMed PMID: 7557380.

45. Hamilton KJ, Arao Y, Korach KS. Estrogen hormone physiology: reproductive findings from estrogen receptor mutant mice. Reprod Biol. 2014;14(1):3-8. Epub 2014 Mar. 13. doi: 10.1016/j.repbio.2013.12.002. PubMed PMID: 24607249; PMCID: PMC4777324.

46. Schneider JS, Stone MK, Wynne-Edwards KE, Horton TH, Lydon J, O'Malley B, Levine JE. Progesterone receptors mediate male aggression toward infants. Proc Natl Acad Sci USA. 2003;100(5):2951-6. Epub 2003 Feb. 26. doi: 10.1073/pnas.0130100100. PubMed PMID: 12601162; PMCID: PMC151447.

47. Ji Y, Rankin C, Grunberg S, Sherrod AE, Ahmadi J, Townsend JJ, Feun LG, Fredericks RK, Russell CA, Kabbinavar FF, Stelzer KJ, Schott A, Verschraegen C. Double-Blind Phase III Randomized Trial of the Antiprogestin Agent Mifepristone in the Treatment of Unresectable Meningioma: SWOG S9005. Journal of clinical oncology: official journal of the American Society of Clinical Oncology. 2015;33(34):4093-8. Epub 2015 Nov. 4. doi: 10.1200/JCO.2015.61.6490. PubMed PMID: 26527781; PMCID: PMC4669593 online at www.jco.org. Author contributions are found at the end of this article.

48. DeMayo FJ, Lydon JP. 90 YEARS OF PROGESTERONE: New insights into progesterone receptor signaling in the endometrium required for embryo implantation. Journal of molecular endocrinology. 2020;65(1): T1-T14. Epub 2019 Dec. 7. doi: 10.1530/JME-19-0212. PubMed PMID: 31809260; PMCID: PMC7261627.

49. Brisken C, Scabia V. 90 YEARS OF PROGESTERONE: Progesterone receptor signaling in the normal breast and its implications for cancer. Journal of molecular endocrinology. 2020;65(1): T81-T94. Epub 2020 Jun. 9. doi: 10.1530/JME-20-0091. PubMed PMID: 32508307.

50. Scabia V, Ayyanan A, De Martino F, Agnoletto A, Battista L, Laszlo C, Treboux A, Zaman K, Stravodimou A, Jallut D, Fiche M, Bucher P, Ambrosini G, Sflomos G, Brisken C. Estrogen receptor positive breast cancers have patient specific hormone sensitivities and rely on progesterone receptor. Nat Commun. 2022;13(1):3127. Epub 2022 Jun. 7. doi: 10.1038/s41467-022-30898-0. PubMed PMID: 35668111; PMCID: PMC9170711.

51. Brain Aromatase Is Essential for Regulation of Sexual Activity in Male Mice [Internet]. Dryad Digital Repository. Available from: https://doi.org/10.5061/dryad.5mkkwh72t.

52. Mao Y, Chen L, Li J, Shangguan AJ, Kujawa S, Zhao H. A network analysis revealed the essential and common downstream proteins related to inguinal hernia. PloS one. 2020;15(1): c0226885. Epub 2020 Jan. 8. doi: 10.1371/journal.pone.0226885. PubMed PMID: 31910207; PMCID: PMC6946160.

53. Wallenstein S, Zucker CL, Fleiss JL. Some statistical methods useful in circulation research. Circ Res. 1980; 47(1):1-9. Epub 1980 Jul. 1. PubMed PMID: 7379260.

54. Bulun SE, Price TM, Aitken J, Mahendroo MS, Simpson ER. A link between breast cancer and local estrogen biosynthesis suggested by quantification of breast adipose tissue aromatase cytochrome P450 transcripts using competitive polymerase chain reaction after reverse transcription. The Journal of clinical endocrinology and metabolism. 1993;77(6):1622-8. Epub 1993 Dec. 1. PubMed PMID: 8117355.

55. Bulun SE, Sharda G, Rink J, Sharma S, Simpson ER. Distribution of aromatase P450 transcripts and adipose fibroblasts in the human breast. The Journal of clinical endocrinology and metabolism. 1996;81(3):1273-7. Epub 1996 Mar. 1. PubMed PMID: 8772611.

56. Chen D, Zhao H, Coon JSt, Ono M, Pearson EK, Bulun SE. Weight gain increases human aromatase expression in mammary gland. Mol Cell Endocrinol. 2012;355(1):114-20. Epub 2012 Feb. 22. doi: 10.1016/j.mce.2012.01.027. PubMed PMID: 22342815; PMCID: 3312968.

57. Zhao H, Cui Y, Dupont J, Sun H, Hennighausen L, Yakar S. Overexpression of the tumor suppressor gene phosphatase and tensin homologue partially inhibits wnt-1-induced mammary tumorigenesis. Cancer research. 2005;65(15):6864-73. Epub 2005 Aug. 3. doi: 10.1158/0008-5472.CAN-05-0181. PubMed PMID: 16061670.

58. Zhao H, Pearson EK, Brooks DC, Coon JSt, Chen D, Demura M, Zhang M, Clevenger CV, Xu X, Veenstra TD, Chatterton RT, DeMayo FJ, Bulun SE. A humanized pattern of aromatase expression is associated with mammary hyperplasia in mice. Endocrinology. 2012; 153(6):2701-13. Epub 2012 Apr. 18. doi: 10.1210/en.2011-1761. PubMed PMID: 22508516; PMCID: 3359608.

59. Bulun SE, Simpson ER. Competitive reverse transcription-polymerase chain reaction analysis indicates that levels of aromatase cytochrome P450 transcripts in adipose tissue of buttocks, thighs, and abdomen of women increase with advancing age. The Journal of clinical endocrinology and metabolism. 1994;78(2): 428-32. Epub 1994 Feb. 1. doi: 10.1210/jcem.78.2.8106632. PubMed PMID: 8106632.

60. Longcope C, Pratt JH, Schneider SH, Fineberg SE. Aromatization of androgens by muscle and adipose tissue in vivo. The Journal of clinical endocrinology and metabolism. 1978;46(1):146-52. Epub 1978 Jan. 1. doi: 10.1210/jcem-46-1-146. PubMed PMID: 752017.

61. Longcope C, Pratt JH, Schneider SH, Fineberg SE. The in vivo metabolism of androgens by muscle and adipose tissue of normal men. Steroids. 1976;28(4): 521-33. Epub 1976 Oct. 1. doi: 10.1016/0039-128x(76)90021-0. PubMed PMID: 1006722.

62. MacDonald PC, Rombaut RP, Siiteri PK. Plasma precursors of estrogen. I. Extent of conversion of plasma delta-4-androstenedione to estrone in normal males and nonpregnant normal, castrate and adrenalectomized females. The Journal of clinical endocrinology and metabolism. 1967;27(8):1103-11. Epub 1967 Aug. 1. doi: 10.1210/jcem-27-8-1103. PubMed PMID: 6035658.
63. Hemsell DL, Grodin JM, Brenner PF, Siiteri PK, MacDonald PC. Plasma precursors of estrogen. II. Correlation of the extent of conversion of plasma androstenedione to estrone with age. The Journal of clinical endocrinology and metabolism. 1974;38(3): 476-9. Epub 1974 Mar. 1. doi: 10.1210/jcem-38-3-476. PubMed PMID: 4815174.
64. Aiman J, Brenner PF, MacDonald PC. Androgen and estrogen production in elderly men with gynecomastia and testicular atrophy after mumps orchitis. The Journal of clinical endocrinology and metabolism. 1980;50 (2):380-6. Epub 1980 Feb. 1. doi: 10.1210/jcem-50-2-380. PubMed PMID: 7354122.
65. Guan J, Zhou W, Hafner M, Blake RA, Chalouni C, Chen IP, De Bruyn T, Giltnane JM, Hartman SJ, Heidersbach A, Houtman R, Ingalla E, Kategaya L, Kleinheinz T, Li J, Martin SE, Modrusan Z, Nannini M, Och J, Ubhayakar S, Wang X, Wertz IE, Young A, Yu M, Sampath D, Hager JH, Friedman LS, Daemen A, Metcalfe C. Therapeutic Ligands Antagonize Estrogen Receptor Function by Impairing Its Mobility. Cell. 2019;178(4):949-63 c18. Epub 2019 Jul. 30. doi: 10.1016/j.cell.2019.06.026. PubMed PMID: 31353221.
66. Zhang W, Schmull S, Du M, Liu J, Lu Z, Zhu H, Xue S, Lian F. Estrogen Receptor alpha and beta in Mouse: Adipose-Derived Stem Cell Proliferation, Migration, and Brown Adipogenesis In Vitro. Cell Physiol Biochem. 2016;38(6):2285-99. doi: 10.1159/000445583. PubMed PMID: 27197672.
67. Osborne CK, Wakeling A, Nicholson RI. Fulvestrant: an oestrogen receptor antagonist with a novel mechanism of action. Br J Cancer. 2004;90 Suppl 1: S2-6. doi: 10.1038/sj.bjc.6601629. PubMed PMID: 15094757; PMCID: 2750773.
68. Harrington WR, Sheng S, Barnett DH, Petz LN, Katzenellenbogen JA, Katzenellenbogen BS. Activities of estrogen receptor alpha- and beta-selective ligands at diverse estrogen responsive gene sites mediating transactivation or transrepression. Mol Cell Endocrinol. 2003;206(1-2):13-22. PubMed PMID: 12943986.
69. Al-Khyatt W, Tufarelli C, Khan R, Iftikhar SY. Selective oestrogen receptor antagonists inhibit oesophageal cancer cell proliferation in vitro. BMC Cancer. 2018; 18(1):121. doi: 10.1186/s12885-018-4030-5. PubMed PMID: 29390981; PMCID: 5796348.
70. Fatima LA, Campello RS, Santos RS, Freitas HS, Frank AP, Machado UF, Clegg DJ. Estrogen receptor 1 (ESR1) regulates VEGFA in adipose tissue. Sci Rep. 2017;7(1):16716. doi: 10.1038/s41598-017-16686-7. PubMed PMID: 29196658; PMCID: 5711936.
71. Ohlsson C, Langenskiold M, Smidfelt K, Poutanen M, Ryberg H, Norlen AK, Nordanstig J, Bergstrom G, Tivesten A. Low Progesterone and Low Estradiol Levels Associate With Abdominal Aortic Aneurysms in Men. The Journal of clinical endocrinology and metabolism. 2022;107(4): c 1413-c25. Epub 2021 Dec. 6. doi: 10.1210/clinem/dgab867. PubMed PMID: 34865072; PMCID: PMC8947245.
72. Henderson VW. Progesterone and human cognition. Climacteric. 2018;21(4):333-40. Epub 2018 Jun. 2. doi: 10.1080/13697137.2018.1476484. PubMed PMID: 29852783; PMCID: PMC6309195.
73. Ishikawa H, Ishi K, Serna VA, Kakazu R, Bulun SE, Kurita T. Progesterone is essential for maintenance and growth of uterine leiomyoma. Endocrinology. 2010; 151(6):2433-42. doi: 10.1210/en.2009-1225. PubMed PMID: 20375184; PMCID: 2875812.
74. Miner JN, Tyree C, Hu J, Berger E, Marschke K, Nakane M, Coghlan MJ, Clemm D, Lane B, Rosen J. A nonsteroidal glucocorticoid receptor antagonist. Mol Endocrinol. 2003;17(1):117-27. Epub 2003 Jan. 4. doi: 10.1210/mc.2002-0010. PubMed PMID: 12511611.
75. Shimizu Y, Yarborough CP, Elger W, Chwalisz K, Osawa Y. Inhibition of aromatase activity in human placental microsomes by 13-retro-antiprogestins. Steroids. 1995;60(2):234-8. Epub 1995 Feb. 1. doi: 10.1016/0039-128x(94) 00043-c. PubMed PMID: 7618191.
76. Nieman LK. Selective progesterone receptor modulators and reproductive health. Curr Opin Endocrinol Diabetes Obes. 2022;29(4):406-12. Epub 2022 Jul. 2. doi: 10.1097/MED.0000000000000753. PubMed PMID: 35776850.
77. Lewis JH, Cottu PH, Lehr M, Dick E, Shearer T, Rencher W, Bexon AS, Campone M, Varga A, Italiano A. Onapristone Extended Release: Safety Evaluation from Phase I-II Studies with an Emphasis on Hepatotoxicity. Drug Saf. 2020;43(10):1045-55. Epub 2020 Jul. 1. doi: 10.1007/s40264-020-00964-x. PubMed PMID: 32594454; PMCID: PMC7497701 content of this article. Alice S. Bexon received payment as a medical writer. Todd Shearer is a paid consultant to Context Therapeutics and was compensated for his time performing pharmacokinetic analyses. William Rencher is a paid consultant to Context Therapeutics. Evan Dick and William Rencher are stock owners of Context Therapeutics. Martin Lehr is the CEO and stock owner of Context Therapeutics. Paul H. Cottu, Mario Campone, Andrea Varga, and Antoine Italiano were the principal investigators for the clinical trials and received salary support from BioTrial, the contract research organization that managed the phase I-II trials.
78. Liu S, Yin P, Xu J, Dotts AJ, Kujawa SA, Coon VJ, Zhao H, Dai Y, Bulun SE. Progesterone receptor-DNA methylation crosstalk regulates depletion of uterine leiomyoma stem cells: A potential therapeutic target. Stem Cell Reports. 2021;16(9):2099-106. Epub 2021 Aug. 14. doi: 10.1016/j.stemcr.2021.07.013. PubMed PMID: 34388365; PMCID: PMC8452515.
79. Lec O, Bosland MC, Wang M, Shidfar A, Hosseini O, Xuci X, Patel P, Schipma MJ, Helenowski I, Kim JJ, Clare SE, Khan SA. Selective progesterone receptor blockade prevents BRCA1-associated mouse mammary tumors through modulation of epithelial and stromal genes. Cancer Lett. 2021;520:255-66. Epub 2021 Jul. 31. doi: 10.1016/j.canlet.2021.07.034. PubMed PMID: 34329741.
80. Nair HB, Santhamma B, Dileep KV, Binkley P, Acosta K, Zhang KYJ, Schenken R, Nickisch K. EC313-a tissue selective SPRM reduces the growth and proliferation of uterine fibroids in a human uterine fibroid tissue xenograft model. Sci Rep. 2019;9(1):17279. Epub 2019 Nov. 23. doi: 10.1038/s41598-019-53467-w. PubMed PMID: 31754172; PMCID: PMC6872653 salaried full time employees of Evestra, Inc. R.S., P.B., K.Y.J.Z. and K.V.D. declare no competing interests.

81. Lamb CA, Helguero LA, Giulianelli S, Soldati R, Vanzulli SI, Molinolo A, Lanari C. Antisense oligonucleotides targeting the progesterone receptor inhibit hormone-independent breast cancer growth in mice. Breast cancer research: BCR. 2005;7(6): R1111-21. Epub 2006 Feb. 7. doi: 10.1186/bcr1345. PubMed PMID: 16457691; PMCID: PMC1410760.
82. Vanzulli S, Efeyan A, Benavides F, Helguero LA, Peters G, Shen J, Conti CJ, Lanari C, Molinolo A. p21, p27 and p53 in estrogen and antiprogestin-induced tumor regression of experimental mouse mammary ductal carcinomas. Carcinogenesis. 2002;23(5):749-58. Epub 2002 May 23. doi: 10.1093/carcin/23.5.749. PubMed PMID: 12016147.
83. Lieber RL, Ward SR. Cellular mechanisms of tissue fibrosis. 4. Structural and functional consequences of skeletal muscle fibrosis. Am J Physiol Cell Physiol. 2013;305(3): C241-52. doi: 10.1152/ajpcell.00173.2013. PubMed PMID: 23761627; PMCID: 3742845.
84. Gillies AR, Bushong EA, Deerinck TJ, Ellisman MH, Lieber RL. Three-dimensional reconstruction of skeletal muscle extracellular matrix ultrastructure. Microsc Microanal. 2014;20(6):1835-40. doi: 10.1017/S1431927614013300. PubMed PMID: 25275291; PMCID: 4267978.
85. Gillies AR, Chapman MA, Bushong EA, Deerinck TJ, Ellisman MH, Lieber RL. High resolution three-dimensional reconstruction of fibrotic skeletal muscle extracellular matrix. J Physiol. 2017;595(4):1159-71. doi: 10.1113/JP273376. PubMed PMID: 27859324; PMCID: 5309386.
86. Gillies AR, Lieber RL. Structure and function of the skeletal muscle extracellular matrix. Muscle Nerve. 2011;44(3):318-31. doi: 10.1002/mus.22094. PubMed PMID: 21949456; PMCID: 3177172.
87. Chapman MA, Meza R, Lieber RL. Skeletal muscle fibroblasts in health and disease. Differentiation. 2016; 92(3):108-15. doi: 10.1016/j.diff.2016.05.007. PubMed PMID: 27282924; PMCID: 5079803.
88. Chapman MA, Mukund K, Subramaniam S, Brenner D, Lieber RL. Three distinct cell populations express extracellular matrix proteins and increase in number during skeletal muscle fibrosis. Am J Physiol Cell Physiol. 2017;312(2): C131-C43. doi: 10.1152/ajpcell.00226.2016. PubMed PMID: 27881411; PMCID: 5336596.
89. Grant RA. Estimation of Hydroxyproline by the Autoanalyser. Journal of clinical pathology. 1964;17: 685-6. PubMed PMID: 14227441; PMCID: 480859.
90. Brown SH, Banuelos K, Ward SR, Lieber RL. Architectural and morphological assessment of rat abdominal wall muscles: comparison for use as a human model. J Anat. 2010;217(3):196-202. doi: 10.1111/j.1469-7580.2010.01271.x. PubMed PMID: 20646108; PMCID: 2919595.
91. Brown SH, Ward SR, Cook MS, Lieber RL. Architectural analysis of human abdominal wall muscles: implications for mechanical function. Spine (Phila Pa 1976). 2011;36(5):355-62. doi: 10.1097/BRS.0b013e3181d12ed7. PubMed PMID: 21325932; PMCID: 3017737.
92. Mohammed H, Russell IA, Stark R, Rueda OM, Hickey TE, Tarulli GA, Serandour AA, Birrell SN, Bruna A, Saadi A, Menon S, Hadfield J, Pugh M, Raj GV, Brown GD, D'Santos C, Robinson JL, Silva G, Launchbury R, Perou CM, Stingl J, Caldas C, Tilley WD, Carroll JS. Progesterone receptor modulates ERalpha action in breast cancer. Nature. 2015;523 (7560):313-7. doi: 10.1038/nature 14583. PubMed PMID: 26153859; PMCID: 4650274.
93. Kalluri R. The biology and function of fibroblasts in cancer. Nat Rev Cancer. 2016;16(9):582-98. doi: 10.1038/nrc.2016.73. PubMed PMID: 27550820.
94 Yin P, Roqueiro D, Huang L, Owen JK, Xie A, Navarro A, Monsivais D, Coon JSt, Kim JJ, Dai Y, Bulun SE. Genome-wide progesterone receptor binding: cell type-specific and shared mechanisms in T47D breast cancer cells and primary leiomyoma cells. PloS one. 2012;7 (1): e29021. Epub 2012 Jan. 25. doi: 10.1371/journal-.pone.0029021. PubMed PMID: 22272226; PMCID: 3260146.
95. Dyson MT, Roqueiro D, Monsivais D, Ercan CM, Pavone ME, Brooks DC, Kakinuma T, Ono M, Jafari N, Dai Y, Bulun SE. Genome-wide DNA methylation analysis predicts an epigenetic switch for GATA factor expression in endometriosis. PLOS genetics. 2014;10 (3): c 1004158. doi: 10.1371/journal.pgen.1004158. PubMed PMID: 24603652; PMCID: 3945170.
96. Liu S, Yin P, Xu J, Dotts AJ, Kujawa SA, Coon VJ, Zhao H, Shilatifard A, Dai Y, Bulun SE. Targeting DNA Methylation Depletes Uterine Leiomyoma Stem Cell-enriched Population by Stimulating Their Differentiation. Endocrinology. 2020;161(10). Epub 2020 Aug. 20. doi: 10.1210/endocr/bqaa143. PubMed PMID: 32812024; PMCID: PMC7497820.
97. Goad J, Rudolph J, Zandigohar M, Tac M, Dai Y, Wei JJ, Bulun SE, Chakravarti D, Rajkovic A. Single-cell sequencing reveals novel cellular heterogeneity in uterine leiomyomas. Hum Reprod. 2022;37(10):2334-49. Epub 2022 Aug. 25. doi: 10.1093/humrep/deac 183. PubMed PMID: 36001050; PMCID: PMC9802286.
98. Cell Rander Arc: https://support.10xgenomics.com/single-cell-multiome-atac-gex/software/overview/welcome).
99. Seurat: https://satijalab.org/seurat/.
100. Hao Y, Hao S, Andersen-Nissen E, Mauck WM, 3rd, Zheng S, Butler A, Lec MJ, Wilk AJ, Darby C, Zager M, Hoffman P, Stoeckius M, Papalexi E, Mimitou EP, Jain J, Srivastava A, Stuart T, Fleming LM, Yeung B, Rogers AJ, McElrath JM, Blish CA, Gottardo R, Smibert P, Satija R. Integrated analysis of multimodal single-cell data. Cell. 2021;184(13):3573-87 e29. Epub 2021 Jun. 2. doi: 10.1016/j.cell.2021.04.048. PubMed PMID: 34062119; PMCID: PMC8238499.
101. Yan F, Powell DR, Curtis DJ, Wong NC. From reads to insight: a hitchhiker's guide to ATAC-seq data analysis. Genome Biol. 2020;21(1):22. Epub 2020 Feb. 6. doi: 10.1186/s13059-020-1929-3. PubMed PMID: 32014034; PMCID: PMC6996192.
102. Langmead B, Trapnell C, Pop M, Salzberg SL. Ultrafast and memory-efficient alignment of short DNA sequences to the human genome. Genome Biol. 2009;10(3): R25. Epub 2009 Mar. 6. doi: 10.1186/gb-2009-10-3-r25. PubMed PMID: 19261174; PMCID: PMC2690996.
103. Duttke SH, Chang MW, Heinz S, Benner C. Identification and dynamic quantification of regulatory elements using total RNA. Genome research. 2019;29 (11):1836-46. Epub 2019 Oct. 28. doi: 10.1101/gr.253492.119. PubMed PMID: 31649059; PMCID: PMC6836739.
104. Ross-Innes CS, Stark R, Teschendorff AE, Holmes KA, Ali HR, Dunning MJ, Brown GD, Gojis O, Ellis IO, Green AR, Ali S, Chin SF, Palmieri C, Caldas C, Carroll JS. Differential oestrogen receptor binding is associated with clinical outcome in breast cancer. Nature. 2012;481(7381):389-93. Epub 2012 Jan. 6. doi: 10.1038/nature10730. PubMed PMID: 22217937; PMCID: PMC3272464.

105. Wang S, Sun H, Ma J, Zang C, Wang C, Wang J, Tang Q, Meyer CA, Zhang Y, Liu XS. Target analysis by integration of transcriptome and ChIP-seq data with BETA. Nat Protoc.
2013;8(12):2502-15. Epub 2013 Nov. 23. doi: 10.1038/nprot.2013.150. PubMed PMID: 24263090; PMCID: PMC4135175.

106. Chappell PE, Lydon JP, Conneely OM, O'Malley BW, Levine JE. Endocrine defects in mice carrying a null mutation for the progesterone receptor gene. Endocrinology. 1997;138(10):4147-52. Epub 1997 Oct. 10. doi: 10.1210/endo.138.10.5456. PubMed PMID: 9322923.

107. Welboren WJ, van Driel MA, Janssen-Megens EM, van Heeringen SJ, Sweep FC, Span PN, Stunnenberg HG. ChIP-Seq of ERalpha and RNA polymerase II defines genes differentially responding to ligands. EMBO J. 2009;28(10):1418-28. doi: 10.1038/emboj.2009.88. PubMed PMID: 19339991; PMCID: 2688537.

108. Critchley HOD, Chodankar RR. 90 YEARS OF PROGESTERONE: Selective progesterone receptor modulators in gynaccological therapies. Journal of molecular endocrinology. 2020;65(1): T15-T33. Epub 2020 Jul. 1. doi: 10.1530/JME-19-0238. PubMed PMID: 32599565; PMCID: PMC7354704.

109. Lin Z, Yin P, Reierstad S, O'Halloran M, Coon VJ, Pearson EK, Mutlu GM, Bulun SE. Adenosine Al receptor, a target and regulator of estrogen receptoralpha action, mediates the proliferative effects of estradiol in breast cancer. Oncogene. 2010;29(8):1114-22. Epub 2009 Nov. 26. doi: 10.1038/onc.2009.409. PubMed PMID: 19935720; PMCID: 2829108.

110. Xu J, Liu S, Yin P, Bulun S, Dai Y. MeDEStrand: an improved method to infer genome-wide absolute methylation levels from DNA enrichment data. BMC Bioinformatics.
2018;19(1):540. Epub 2018 Dec. 24. doi: 10.1186/s12859-018-2574-7. PubMed PMID: 30577750; PMCID: PMC6303941.

111. Yilmaz BD, Sison CAM, Yildiz S, Miyazaki K, Coon VJ, Yin P, Bulun SE. Genome-wide estrogen receptor-alpha binding and action in human endometrial stromal cells. F S Sci. 2020;1(1):59-66. Epub 2020 Aug. 1. doi: 10.1016/j.xfss.2020.06.002. PubMed PMID: 35559740.

112. Gao S, Dai Y, Rehman J. A Bayesian inference transcription factor activity model for the analysis of single-cell transcriptomes. Genome research. 2021;31 (7):1296-311. Epub 2021 Jul. 2. doi: 10.1101/gr.265595.120. PubMed PMID: 34193535; PMCID: PMC8256867.

113. Gao S, Rehman J, Dai Y. Assessing comparative importance of DNA sequence and epigenetic modifications on gene expression using a deep convolutional neural network. Comput Struct Biotechnol J. 2022;20: 3814-23. Epub 2022 Jul. 28. doi: 10.1016/j.csbj.2022.07.014. PubMed PMID: 35891778; PMCID: PMC9307602.

114. Zhou J, Gurates B, Yang S, Sebastian S, Bulun SE. Malignant breast epithelial cells stimulate aromatase expression via promoter II in human adipose fibroblasts: an epithelial-stromal interaction in breast tumors mediated by CCAAT/enhancer binding protein beta. Cancer research. 2001;61(5):2328-34. PubMed PMID: 11280806.

115. Deb S, Jianfeng Z, Amin SA, Gonca IA, Bertan YM, Zihong L, Bulun SE. A novel role of sodium butyrate in the regulation of cancer-associated aromatase promoters 1.3 and II by disrupting a transcriptional complex in breast adipose fibroblasts. J Biol Chem. 2006; 281(5):2585-97. PubMed PMID: 16303757.

116. Zhao H, Innes J, Brooks DC, Reierstad S, Yilmaz MB, Lin Z, Bulun SE. A novel promoter controls Cyp19al gene expression in mouse adipose tissue. Reprod Biol Endocrinol. 2009;7:37. Epub 2009 Apr. 28. doi: 10.1186/1477-7827-7-37. PubMed PMID: 19393092; PMCID: 2684739.

117. Chen D, Reierstad S, Fang F, Bulun SE. JunD and JunB integrate prostaglandin E2 activation of breast cancer-associated proximal aromatase promoters. Mol Endocrinol. 2011;25(5):767-75. doi: 10.1210/mc.2010-0368. PubMed PMID: 21393445; PMCID: 3082330.

118. Chen D, Reierstad S, Lin Z, Lu M, Brooks C, Li N, Innes J, Bulun SE. Prostaglandin E(2) induces breast cancer related aromatase promoters via activation of p38 and c-Jun NH(2)-terminal kinase in adipose fibroblasts. Cancer research. 2007;67(18):8914-22. Epub 2007 Sep. 19. doi: 10.1158/0008-5472.CAN-06-4751. PubMed PMID: 17875734.

119. Ono M, Yin P, Navarro A, Moravek MB, Coon JSt, Druschitz SA, Serna VA, Qiang W, Brooks DC, Malpani SS, Ma J, Ercan CM, Mittal N, Monsivais D, Dyson MT, Yemelyanov A, Maruyama T, Chakravarti D, Kim JJ, Kurita T, Gottardi CJ, Bulun SE. Paracrine activation of WNT/beta-catenin pathway in uterine leiomyoma stem cells promotes tumor growth. Proc Natl Acad Sci USA. 2013;110(42):17053-8. doi: 10.1073/pnas.1313650110. PubMed PMID: 24082114; PMCID: 3801037.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating and/or preventing a hernia in a subject in need thereof, the method comprising administering to the subject an effective amount of one or more therapeutic agents comprising one or more progesterone antagonists; wherein the subject is an elderly man; and wherein the subject has undergone surgery for hernia repair or the subject is preparing to undergo surgery for hernia repair and the therapeutic agent is administered to the subject before, during, and/or after the surgery.

2. The method of claim 1, wherein the one or more progesterone antagonists are selected from the group consisting of mifepristone, ulipristal acetate, and onapristone.

3. The method of claim 1, wherein the subject has or is at risk for developing a hernia, wherein the hernia is selected from an inguinal hernia, a femoral hernia, an umbilical hernia, a hiatal hernia, an incisional hernia, and diastasis recti.

4. The method of claim 1, wherein the therapeutic agent is administered locally at a site of a hernia or at a site at risk of developing a hernia.

5. The method of claim 1, wherein the therapeutic agent is administered orally or systemically.

6. The method of claim 1, wherein the therapeutic agent is administered by injection.

7. The method of claim 1, wherein the therapeutic agent is administered topically.

8. The method of claim 1, wherein the subject has undergone surgery for hernia repair or the subject is preparing to undergo surgery for hernia repair and the therapeutic agent is incorporated into an implantable material that is implanted in the subject at the hernia and releases the therapeutic agent.

9. A method for treating and/or preventing a hernia in a subject in need thereof, the method comprising administering to the subject an effective amount of one or more progesterone antagonists, wherein the subject has or is at risk of developing a hernia, wherein the subject is an elderly man; and wherein the subject has undergone surgery for hernia repair or the subject is preparing to undergo surgery for hernia repair and the therapeutic agent is administered to the subject before, during, and/or after the surgery.

10. The method of claim 9, wherein the hernia is selected from an inguinal hernia, a femoral hernia, an umbilical hernia, a hiatal hernia, an incisional hernia, and diastasis recti.

11. The method of claim 9, wherein the one or more progesterone antagonists are selected from the group consisting of mifepristone, ulipristal acetate, and onapristone.

12. The method of claim 9, wherein the one or more progesterone antagonists are administered locally at a site of a hernia or at a site at risk of developing a hernia.

13. The method of claim 9, wherein the one or more progesterone antagonists are administered orally or systemically.

14. The method of claim 9, wherein the subject has undergone surgery for hernia repair or the subject is preparing to undergo surgery for hernia repair and the therapeutic agent is incorporated into an implantable material that is implanted in the subject at the hernia and releases the therapeutic agent.

15. The method of claim 14, wherein the implantable material comprises a mesh material for hernia repair.

16. A method for inhibiting proliferation of fibroblasts, fibrosis, muscle atrophy, or hernia development in lower abdominal muscle of a human subject assigned male at birth, the method comprising administering to the human subject assigned male at birth an effective amount of one or more progesterone antagonists; and wherein the subject has undergone surgery for hernia repair or the subject is preparing to undergo surgery for hernia repair and the therapeutic agent is administered to the subject before, during, and/or after the surgery.

17. The method of claim 16, wherein the human subject assigned male at birth is elderly.

* * * * *